(12) United States Patent
Blank et al.

(10) Patent No.: US 10,907,180 B2
(45) Date of Patent: Feb. 2, 2021

(54) EXTRACELLULAR PRODUCTION OF DESIGNER HYDROXYALKANOYLOXY ALKANOIC ACIDS WITH RECOMBINANT BACTERIA

(71) Applicant: Rheinisch-Westfaelische Technische Hochshule Aachen (RWTH), Aachen (DE)

(72) Inventors: Lars M. Blank, Dortmund (DE); Till Tiso, Cologne (DE); Andrea Germer, Aachen (DE)

(73) Assignee: Rheinisch-Westfaelische Technische Hochshule Aachen (RWTH), Aachen (DE)

( * ) Notice: Subject to any disclaimer, the term of this patent is extended or adjusted under 35 U.S.C. 154(b) by 0 days.

(21) Appl. No.: 15/742,246

(22) PCT Filed: Jul. 6, 2016

(86) PCT No.: PCT/IB2016/054037
§ 371 (c)(1),
(2) Date: Jan. 5, 2018

(87) PCT Pub. No.: WO2017/006252
PCT Pub. Date: Jan. 12, 2017

(65) Prior Publication Data
US 2018/0112241 A1   Apr. 26, 2018

(30) Foreign Application Priority Data
Jul. 8, 2015   (EP) .................................... 15175922

(51) Int. Cl.
*C12N 1/20* (2006.01)
*C12P 7/62* (2006.01)
(Continued)

(52) U.S. Cl.
CPC .............. *C12P 7/6409* (2013.01); *C12N 1/20* (2013.01); *C12N 9/1029* (2013.01);
(Continued)

(58) Field of Classification Search
None
See application file for complete search history.

(56) References Cited

U.S. PATENT DOCUMENTS

| | | | |
|---|---|---|---|
| 10,190,144 B2* | 1/2019 | Solaiman | C07K 14/21 |
| 2014/0330032 A1* | 11/2014 | Lynch | C12P 7/00 554/1 |
| 2015/0030577 A1* | 1/2015 | Asolkar | A01N 37/06 424/93.47 |

FOREIGN PATENT DOCUMENTS

| | | |
|---|---|---|
| DE | 10 2012 201360 A1 | 8/2013 |
| EP | 2 572 172 A1 | 3/2013 |

(Continued)

OTHER PUBLICATIONS

Machine English translation of KR 10-2012-0044192, published May 7, 2012 (Year: 2012).*
(Continued)

*Primary Examiner* — Richard C Ekstrom
(74) *Attorney, Agent, or Firm* — Kagan Binder, PLLC

(57) ABSTRACT

The present invention relates to a host cell comprising an rhlA gene or an ortholog thereof that is capable of producing hydroxyalkanoyloxy alkanoic acid (HAA) and achieving an HAA concentration of more than 1 g L$^{-1}$ when cultured. The invention further relates to methods of producing such a host cell and to the use of said host cell for producing HAA. The present invention also relates to methods of producing HAA using said host cell, HAA compositions produced by these methods, as well as methods of producing fatty acid compositions, fatty alcohol compositions, or hydrocarbon compositions comprising producing HAA using said host cell,
(Continued)

and fatty acid compositions, fatty alcohol compositions, or hydrocarbon compositions produced by said methods.

20 Claims, 13 Drawing Sheets

Specification includes a Sequence Listing.

(51) Int. Cl.
    *C12P 7/64*     (2006.01)
    *C12N 9/10*     (2006.01)
    *C12P 7/42*     (2006.01)

(52) U.S. Cl.
    CPC .............. *C12N 9/1051* (2013.01); *C12P 7/42* (2013.01); *C12P 7/62* (2013.01); *C12P 7/64* (2013.01); *C12Y 204/01* (2013.01)

(56) References Cited

FOREIGN PATENT DOCUMENTS

| EP | 2 786 743 A1 | 10/2014 | |
|---|---|---|---|
| KR | 2012 0044192 A | 5/2012 | |
| WO | 2012/013554 A1 | 2/2012 | |
| WO | WO-2013041670 A1 * | 3/2013 | .............. C12P 19/44 |
| WO | 2013/087674 A1 | 6/2013 | |

OTHER PUBLICATIONS

Zhu, K., and Rock, C.O., (2008) "Rhl a Converts Beta-Hydroxyacyl-Acyl Carrier Protein Intermediates in Fatty Acid Synthesis to the Beta-Hydroxydecanoyl-Beta-Hydroxydecanoate Component of Rhamnolipids in Pseudomonas Aeruginosa," Journal of Bacteriology,190:3147-3154.

Williamson, N.R., et al. (2008) "Integrated Regulation Involving Quorum Sensing, A Two-Component System, a GGDEF/EAL Domain Protein and a Post-Transcriptional Regulator Controls Swarming and Rh1A-Dependent Surfactant Biosynthesis in Serratia", Environmental Microbiology, 10:1202-1217.

Ochsner, U.A., et al., (1994) "Isolation, Characterization, and Expression in *Escherichia coli* of the Pseudomonas Aeruginosa RhlAB Genes Encodcing a Rhamnosyltransferase Involved in Rhamnolipid Biosurfactant Synthesis," Journal of Biological Chemistry, 269:19787-19795.

Cabrera-Valladares, N., et al. (2006) "Monorhamnolipids and 3-(3-Hdroxyalkanoyloxy) Alkanoic Acids (HAAs) Production Using *Escherichia coli* as a Heterologous Host", Applied Microbiology and Biotechnology, 73:187-194.

Tavares, L.F.D., et al., (2013) "Characterization of Rhamnolipids Produced by Wild-Type and Engineered Burkholderia Kururiensis," Applied Microbiology and Biotechnology, 97:1909-1921.

Wittgens A., et al., (2011) "Growth Independent Rhamnolipid Production from Glucose Using the Non-Pathogenic Pseudomonas Putida KT2440," Microbial Cell Factories, 10:80:1-17.

Choi, M.H., et al. (2011) "Metabolic Relationship Between Polyhydroxyalkanoic Acid and Rhamnolipid Synthesis in Pseudomonas Aeruginosa: Comparative 13C NMR Analysis of the Products in Wild-Type and Mutants": Journal of Biotechnology, 151:30-42.

Deziel, E., et al. (2003) "rhIA is Required for the Production of a Novel Biosurfactant Promoting Swarming Motility in Pseudomonas Aeruginosa: 3-(3-hydroxyalkanoyloxy)Alkanoic Acids (HAAs), the Precursors of Rhamnolipids," Microbiology, 149:2005-2013.

Dubeau, D., et al. (2009) "Burkholderia Thailandensis Harbors Two Identical rhl Gene Clusters Responsible for the Biosynthesis of Rhamnolipids," BMC Microbiology, 9:263:1-12.

Henkel, M., et al. (2012) "Rhamnolipids as Biosurfactants from Renewable Resources: Concepts for Next-Generation Rhamnolipid Production," Process Biochemistry, 47:1207-1219.

Abdel-Mawgoud, A.M., et al. (2010) "Rhamnolipids: Diversity of Structures, Microbial Origins and Roles," Applied Microbiology and Biotechnology, 86:1323-1336.

Zhou, Y.J., et al. (2014) "Fatty Acid-Derived Biofuels and Chemicals Production in *Saccharomyces cerevisiae*," Frontiers in Bioengineering and Biotechnology, 2:32:1-32.

* cited by examiner

Figure 8

| Experiment No. | 1 | 2 | 3 |
|---|---|---|---|
| Organism | *P. taiwanensis* VLB120 pSB01 | *P. taiwanensis* VLB120 pSB01 | *P. putida* KT2440 pSB01 |
| Glucose [g/L] | 10 | 40 | 10 |
| Cell Dry Weight [$g_{CDW}$/L] | 5 | 8 | 5,7 |
| Maximal Titer [$g_{HAA}$/ L] | 1,80 | 7,00 | 1,54 |
| Yield [$g_{HAA}$/ $g_{substrate}$] | 0,18 | 0,18 | 0,15 |
| Carbon Yield [$Cmol_{HAA}$/ $Cmol_{substrate}$] | 0,32 | 0,31 | 0,27 |
| % of theoretical maximum | 48% | 46% | 41% |
| Process Time [h] | 22 | 140 | 22 |
| HAA-Production Rate [$mCmol_{HAA}$/(L h)] | 0,24 | 0,15 | 0,20 |
| Space-Time Yield [$mg_{HAA}$/(L h)] | 81,8 | 50,0 | 69,5 |
| Specific HAA-Production Rate [g/($g_{CDW}$ h)] | 0,016 | 0,006 | 0,012 |
| Specific HAA-Production Rate [g/($g_{Subs}$ h)] | 0,008 | 0,001 | 0,007 |
| Data shown in | --- | Figure 3 | Figure 1, Figure 5 |

Figure 13

>gi|15598675|ref|NP_252169.1| rhamnosyltransferase subunit A [Pseudomonas aeruginosa PAO1]
MRRESLLVSVCKGLRVHVERVGQDPGRSTVMLVNGAMATTASFARTCKCLAEHFNVVLFDLP
FAGQSRQHNPQRGLITKDDEVEILLALIERFEVNHLVSASWGGISTLLALSRNPRGIRSSVV
MAFAPGLNQAMLDYVGRAQALIELDDKSAIGHLLNETVGKYLPQRLKASNHQHMASLATGEY
EQARFHIDQVLALNDRGYLACLERIQSHVHFINGSWDEYTTAEDARQFRDYLPHCSFSRVEG
TGHFLDLESKLAAVRVHRALLEHLLKQPEPQRAERAAGFHEMAIGYA

Figure 14

>gi|291616307|ref|YP_003519049.1| RhlA [Pantoea ananatis LMG 20103]
MIYIKKIYFSRVIVGKESDMSHAYSVININKLNVYVELVKCSVPTRNRTILINGALATSSSF
RNWKRFLADKSDVITFDLPFSGKSKPYNEQDCNIVTLDDEVAIIREIISIYKPNIIASASWG
GASTLKLLNNGEDGLEHAIIASYSFEFNDRMRTYVKQANLYSKEKKFVDLAHLMNEEVGAYL
PNKNEILQFQTPHHAGEIEYRQGRFHLEQIANIRNHDYKSIIDNSACQFHFINGDLDIHTPQ
KNIEEICGESDKTCFYQIRDAGHFLDLEGKVSRERTAAAFNTIFNQIGV

Figure 15

>gi|755902277|gb|AJK48831.1| rhamnosyltransferase I subunit A [Burkholderia glumae PG1]
MPIEKQVVPLPNGLQVYVEHHVYDPSFETVILINGALATTASFGQTVRYLGERLNSLCFDLP
YAGQSRQHNPGKFVLTKDDEVDILLHLAERFRPSYLLSVSWGGVASLFALSRGCTSIRRAVV
ASFSPFLNDAMVDYVTRARDHIAAGENLHAAQLLNDTVGRYLPRIMKLYNYRYLTKLPRDEQ
DQVAFHVNQILEMKPEAYLDQFTQIQCGVKFINGELDEYTTPADVRRLGSYVRRAEFETIGK
AGHFLDLEGRQQQENVRAAILGYFCDEARSASSPDGSFDSLSPMPLLS HAA metabolism pathway

SEQUENCE LISTING

<160> NUMBER OF SEQ ID NOS: 16

<210> SEQ ID NO 1
<211> LENGTH: 40
<212> TYPE: DNA
<213> ORGANISM: artificial
<220> FEATURE:
<223> OTHER INFORMATION: SynPro8 promoter

<400> SEQUENCE: 1
agctcttgac aaggtcggaa aattgaagta taatatcagt          40

<210> SEQ ID NO 2
<211> LENGTH: 40
<212> TYPE: DNA
<213> ORGANISM: artificial
<220> FEATURE:
<223> OTHER INFORMATION: synthetic promoter sequence

<400> SEQUENCE: 2
tttccttgac aagcctagtt tcgccattta taatgactcg          40

<210> SEQ ID NO 3
<211> LENGTH: 40
<212> TYPE: DNA
<213> ORGANISM: artificial
<220> FEATURE:
<223> OTHER INFORMATION: synthetic promoter sequence

<400> SEQUENCE: 3
ggtggttgac attggcatta caacgtatta taatttagcg          40

<210> SEQ ID NO 4
<211> LENGTH: 40
<212> TYPE: DNA
<213> ORGANISM: artificial
<220> FEATURE:
<223> OTHER INFORMATION: synthetic promoter sequence

<400> SEQUENCE: 4
tagagttgac acaccttcgg gtgggcctta taatactcgc          40

<210> SEQ ID NO 5
<211> LENGTH: 40
<212> TYPE: DNA
<213> ORGANISM: artificial
<220> FEATURE:
<223> OTHER INFORMATION: synthetic
<220> FEATURE:
<221> NAME/KEY: misc
<222> LOCATION: (1)..(1)
<223> OTHER INFORMATION: d is a, t or g
<220> FEATURE:
<221> NAME/KEY: misc
<222> LOCATION: (2)..(2)
<223> OTHER INFORMATION: d is a, t or g
<220> FEATURE:
<221> NAME/KEY: misc
<222> LOCATION: (3)..(3)
<223> OTHER INFORMATION: b is c, t or g
<220> FEATURE:
<221> NAME/KEY: misc
<222> LOCATION: (4)..(4)
<223> OTHER INFORMATION: n is a, t, c, or g
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc

```
<222> LOCATION: (5)..(5)
<223> OTHER INFORMATION: s is g or c
<220> FEATURE:
<221> NAME/KEY: misc
<222> LOCATION: (12)..(12)
<223> OTHER INFORMATION: h is a, t or c
<220> FEATURE:
<221> NAME/KEY: misc
<222> LOCATION: (13)..(13)
<223> OTHER INFORMATION: d is g, t or a
<220> FEATURE:
<221> NAME/KEY: misc
<222> LOCATION: (14)..(14)
<223> OTHER INFORMATION: s is g or c
<220> FEATURE:
<221> NAME/KEY: misc
<222> LOCATION: (15)..(15)
<223> OTHER INFORMATION: b is t, c or g
<220> FEATURE:
<221> NAME/KEY: misc
<222> LOCATION: (16)..(16)
<223> OTHER INFORMATION: y is c or t
<220> FEATURE:
<221> NAME/KEY: misc
<222> LOCATION: (17)..(17)
<223> OTHER INFORMATION: d is g, a or t
<220> FEATURE:
<221> NAME/KEY: misc
<222> LOCATION: (18)..(18)
<223> OTHER INFORMATION: b is g, t or c
<220> FEATURE:
<221> NAME/KEY: misc
<222> LOCATION: (19)..(19)
<223> OTHER INFORMATION: d is a, t or g
<220> FEATURE:
<221> NAME/KEY: misc
<222> LOCATION: (20)..(20)
<223> OTHER INFORMATION: d is a, t or g
<220> FEATURE:
<221> NAME/KEY: misc
<222> LOCATION: (21)..(21)
<223> OTHER INFORMATION: n is a, t, c or g
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc
<222> LOCATION: (22)..(22)
<223> OTHER INFORMATION: h is a, c or t
<220> FEATURE:
<221> NAME/KEY: misc
<222> LOCATION: (23)..(23)
<223> OTHER INFORMATION: d is t, g or a
<220> FEATURE:
<221> NAME/KEY: misc
<222> LOCATION: (24)..(24)
<223> OTHER INFORMATION: b is t, c or g
<220> FEATURE:
<221> NAME/KEY: misc
<222> LOCATION: (25)..(25)
<223> OTHER INFORMATION: s is g or c
<220> FEATURE:
<221> NAME/KEY: misc
<222> LOCATION: (26)..(26)
<223> OTHER INFORMATION: h is a, t or c
<220> FEATURE:
<221> NAME/KEY: misc
<222> LOCATION: (27)..(27)
<223> OTHER INFORMATION: h is a, t or c
<220> FEATURE:
<221> NAME/KEY: misc
<222> LOCATION: (28)..(28)
<223> OTHER INFORMATION: k is g or t
<220> FEATURE:
<221> NAME/KEY: misc
<222> LOCATION: (35)..(35)
<223> OTHER INFORMATION: d is a, g or t
<220> FEATURE:
```

```
<221> NAME/KEY: misc
<222> LOCATION: (36)..(36)
<223> OTHER INFORMATION: h is t, a or c
<220> FEATURE:
<221> NAME/KEY: misc
<222> LOCATION: (37)..(37)
<223> OTHER INFORMATION: h is t, a or c
<220> FEATURE:
<221> NAME/KEY: misc
<222> LOCATION: (38)..(38)
<223> OTHER INFORMATION: n is a, t, c or g
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc
<222> LOCATION: (39)..(39)
<223> OTHER INFORMATION: s is g or c
<220> FEATURE:
<221> NAME/KEY: misc
<222> LOCATION: (40)..(40)
<223> OTHER INFORMATION: b is t, g or c

<400> SEQUENCE: 5
ddbnsttgac ahdsbydbdd nhdbshhkta taatdhhnsb                              40

<210> SEQ ID NO 6
<211> LENGTH: 295
<212> TYPE: PRT
<213> ORGANISM: Pseudomonas aeruginosa

<400> SEQUENCE: 6
```

| Met | Arg | Arg | Glu | Ser | Leu | Leu | Val | Ser | Val | Cys | Lys | Gly | Leu | Arg | Val |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| His | Val | Glu | Arg | Val | Gly | Gln | Asp | Pro | Gly | Arg | Ser | Thr | Val | Met | Leu |
|     |     |     | 20  |     |     |     |     | 25  |     |     |     |     | 30  |     |     |

| Val | Asn | Gly | Ala | Met | Ala | Thr | Thr | Ala | Ser | Phe | Ala | Arg | Thr | Cys | Lys |
|     |     | 35  |     |     |     |     | 40  |     |     |     |     | 45  |     |     |     |

| Cys | Leu | Ala | Glu | His | Phe | Asn | Val | Val | Leu | Phe | Asp | Leu | Pro | Phe | Ala |
| 50  |     |     |     |     | 55  |     |     |     |     | 60  |     |     |     |     |     |

| Gly | Gln | Ser | Arg | Gln | His | Asn | Pro | Gln | Arg | Gly | Leu | Ile | Thr | Lys | Asp |
| 65  |     |     |     |     | 70  |     |     |     |     | 75  |     |     |     |     | 80  |

| Asp | Glu | Val | Glu | Ile | Leu | Leu | Ala | Leu | Ile | Glu | Arg | Phe | Glu | Val | Asn |
|     |     |     |     | 85  |     |     |     |     | 90  |     |     |     |     | 95  |     |

| His | Leu | Val | Ser | Ala | Ser | Trp | Gly | Gly | Ile | Ser | Thr | Leu | Leu | Ala | Leu |
|     |     |     | 100 |     |     |     |     | 105 |     |     |     |     | 110 |     |     |

| Ser | Arg | Asn | Pro | Arg | Gly | Ile | Arg | Ser | Ser | Val | Val | Met | Ala | Phe | Ala |
|     |     |     | 115 |     |     |     |     | 120 |     |     |     |     | 125 |     |     |

| Pro | Gly | Leu | Asn | Gln | Ala | Met | Leu | Asp | Tyr | Val | Gly | Arg | Ala | Gln | Ala |
|     | 130 |     |     |     |     | 135 |     |     |     |     | 140 |     |     |     |     |

| Leu | Ile | Glu | Leu | Asp | Asp | Lys | Ser | Ala | Ile | Gly | His | Leu | Leu | Asn | Glu |
| 145 |     |     |     |     | 150 |     |     |     |     | 155 |     |     |     |     | 160 |

| Thr | Val | Gly | Lys | Tyr | Leu | Pro | Gln | Arg | Leu | Lys | Ala | Ser | Asn | His | Gln |
|     |     |     |     | 165 |     |     |     |     | 170 |     |     |     |     | 175 |     |

| His | Met | Ala | Ser | Leu | Ala | Thr | Gly | Glu | Tyr | Glu | Gln | Ala | Arg | Phe | His |
|     |     |     | 180 |     |     |     |     | 185 |     |     |     |     | 190 |     |     |

| Ile | Asp | Gln | Val | Leu | Ala | Leu | Asn | Asp | Arg | Gly | Tyr | Leu | Ala | Cys | Leu |
|     |     |     | 195 |     |     |     |     | 200 |     |     |     |     | 205 |     |     |

| Glu | Arg | Ile | Gln | Ser | His | Val | His | Phe | Ile | Asn | Gly | Ser | Trp | Asp | Glu |
|     | 210 |     |     |     |     | 215 |     |     |     |     | 220 |     |     |     |     |

| Tyr | Thr | Thr | Ala | Glu | Asp | Ala | Arg | Gln | Phe | Arg | Asp | Tyr | Leu | Pro | His |

```
                225                 230                 235                 240
        Cys Ser Phe Ser Arg Val Glu Gly Thr Gly His Phe Leu Asp Leu Glu
                        245                 250                 255

Ser Lys Leu Ala Ala Val Arg Val His Arg Ala Leu Leu Glu His Leu
                        260                 265                 270

Leu Lys Gln Pro Glu Pro Gln Arg Ala Glu Arg Ala Ala Gly Phe His
                        275                 280                 285

Glu Met Ala Ile Gly Tyr Ala
                        290                 295

<210> SEQ ID NO 7
<211> LENGTH: 297
<212> TYPE: PRT
<213> ORGANISM: Pantoea ananatis

<400> SEQUENCE: 7

Met Ile Tyr Ile Lys Lys Ile Tyr Phe Ser Arg Val Ile Val Gly Lys
        1               5                   10                  15

Glu Ser Asp Met Ser His Ala Tyr Ser Val Ile Asn Ile Asn Lys Leu
                        20                  25                  30

Asn Val Tyr Val Glu Leu Val Lys Cys Ser Val Pro Thr Arg Asn Arg
                        35                  40                  45

Thr Ile Leu Ile Asn Gly Ala Leu Ala Thr Ser Ser Ser Phe Arg Asn
                        50                  55                  60

Trp Lys Arg Phe Leu Ala Asp Lys Ser Asp Val Ile Thr Phe Asp Leu
        65                  70                  75                  80

Pro Phe Ser Gly Lys Ser Lys Pro Tyr Asn Glu Gln Asp Cys Asn Ile
                        85                  90                  95

Val Thr Leu Asp Asp Glu Val Ala Ile Ile Arg Glu Ile Ile Ser Ile
                        100                 105                 110

Tyr Lys Pro Asn Ile Ile Ala Ser Ala Ser Trp Gly Gly Ala Ser Thr
                        115                 120                 125

Leu Lys Leu Leu Asn Asn Gly Glu Asp Gly Leu Glu His Ala Ile Ile
                        130                 135                 140

Ala Ser Tyr Ser Phe Glu Phe Asn Asp Arg Met Arg Thr Tyr Val Lys
        145                 150                 155                 160

Gln Ala Asn Leu Tyr Ser Lys Glu Lys Lys Phe Val Asp Leu Ala His
                        165                 170                 175

Leu Met Asn Glu Glu Val Gly Ala Tyr Leu Pro Asn Lys Asn Glu Ile
                        180                 185                 190

Leu Gln Phe Gln Thr Pro His His Ala Gly Glu Ile Glu Tyr Arg Gln
                        195                 200                 205

Gly Arg Phe His Leu Glu Gln Ile Ala Asn Ile Arg Asn His Asp Tyr
                        210                 215                 220

Lys Ser Ile Ile Asp Asn Ser Ala Cys Gln Phe His Phe Ile Asn Gly
        225                 230                 235                 240

Asp Leu Asp Ile His Thr Pro Gln Lys Asn Ile Glu Glu Ile Cys Gly
                        245                 250                 255

Glu Ser Asp Lys Thr Cys Phe Tyr Gln Ile Arg Asp Ala Gly His Phe
                        260                 265                 270

Leu Asp Leu Glu Gly Lys Val Ser Arg Glu Arg Thr Ala Ala Ala Phe
                        275                 280                 285

Asn Thr Ile Phe Asn Gln Ile Gly Val
                        290                 295
```

<210> SEQ ID NO 8
<211> LENGTH: 296
<212> TYPE: PRT
<213> ORGANISM: Burkholderia glumae PG1

<400> SEQUENCE: 8

Met Pro Ile Glu Lys Gln Val Val Pro Leu Pro Asn Gly Leu Gln Val
1 5 10 15

Tyr Val Glu His His Val Tyr Asp Pro Ser Phe Glu Thr Val Ile Leu
20 25 30

Ile Asn Gly Ala Leu Ala Thr Thr Ala Ser Phe Gly Gln Thr Val Arg
35 40 45

Tyr Leu Gly Glu Arg Leu Asn Ser Leu Cys Phe Asp Leu Pro Tyr Ala
50 55 60

Gly Gln Ser Arg Gln His Asn Pro Gly Lys Phe Val Leu Thr Lys Asp
65 70 75 80

Asp Glu Val Asp Ile Leu Leu His Leu Ala Glu Arg Phe Arg Pro Ser
85 90 95

Tyr Leu Leu Ser Val Ser Trp Gly Gly Val Ala Ser Leu Phe Ala Leu
100 105 110

Ser Arg Gly Cys Thr Ser Ile Arg Arg Ala Val Val Ala Ser Phe Ser
115 120 125

Pro Phe Leu Asn Asp Ala Met Val Asp Tyr Val Thr Arg Ala Arg Asp
130 135 140

His Ile Ala Ala Gly Glu Asn Leu His Ala Ala Gln Leu Leu Asn Asp
145 150 155 160

Thr Val Gly Arg Tyr Leu Pro Arg Ile Met Lys Leu Tyr Asn Tyr Arg
165 170 175

Tyr Leu Thr Lys Leu Pro Arg Asp Glu Gln Asp Gln Val Ala Phe His
180 185 190

Val Asn Gln Ile Leu Glu Met Lys Pro Glu Ala Tyr Leu Asp Gln Phe
195 200 205

Thr Gln Ile Gln Cys Gly Val Lys Phe Ile Asn Gly Glu Leu Asp Glu
210 215 220

Tyr Thr Thr Pro Ala Asp Val Arg Arg Leu Gly Ser Tyr Val Arg Arg
225 230 235 240

Ala Glu Phe Glu Thr Ile Gly Lys Ala Gly His Phe Leu Asp Leu Glu
245 250 255

Gly Arg Gln Gln Gln Glu Asn Val Arg Ala Ala Ile Leu Gly Tyr Phe
260 265 270

Cys Asp Glu Ala Arg Ser Ala Ser Ser Pro Asp Gly Ser Phe Asp Ser
275 280 285

Leu Ser Pro Met Pro Leu Leu Ser
290 295

<210> SEQ ID NO 9
<211> LENGTH: 20
<212> TYPE: DNA
<213> ORGANISM: artificial
<220> FEATURE:
<223> OTHER INFORMATION: synthetic oligonucleotide

<400> SEQUENCE: 9
atccagggta ccagctcttg 20

<210> SEQ ID NO 10

```
<211> LENGTH: 28
<212> TYPE: DNA
<213> ORGANISM: artificial
<220> FEATURE:
<223> OTHER INFORMATION: synthetic oligonucleotide

<400> SEQUENCE: 10
ctgcatgcct aggcttgtca aggaaagg                                        28

<210> SEQ ID NO 11
<211> LENGTH: 39
<212> TYPE: DNA
<213> ORGANISM: artificial
<220> FEATURE:
<223> OTHER INFORMATION: synthetic oligonucleotide

<400> SEQUENCE: 11
ctttaagaag gagatataca tatgcggcgc gaaagtctg                            39

<210> SEQ ID NO 12
<211> LENGTH: 29
<212> TYPE: DNA
<213> ORGANISM: artificial
<220> FEATURE:
<223> OTHER INFORMATION: synthetic oligonucleotide

<400> SEQUENCE: 12
gacgagtcga ccgcaggtca agggttcag                                       29

<210> SEQ ID NO 13
<211> LENGTH: 46
<212> TYPE: DNA
<213> ORGANISM: artificial
<220> FEATURE:
<223> OTHER INFORMATION: synthetic oligonucleotide

<400> SEQUENCE: 13
gccgcgcggc agccatatga tatacattaa aaaaatttac ttttcg                    46

<210> SEQ ID NO 14
<211> LENGTH: 45
<212> TYPE: DNA
<213> ORGANISM: artificial
<220> FEATURE:
<223> OTHER INFORMATION: synthetic oligonucleotide

<400> SEQUENCE: 14
cggagctcga attcggatcc tcagacacca atctggttaa aaatg                     45

<210> SEQ ID NO 15
<211> LENGTH: 35
<212> TYPE: DNA
<213> ORGANISM: artificial
<220> FEATURE:
<223> OTHER INFORMATION: synthetic oligonucleotide

<400> SEQUENCE: 15
gccgcgcggc agccatatgc ctatcgagaa acagg                                35

<210> SEQ ID NO 16
<211> LENGTH: 37
<212> TYPE: DNA
```

```
<213> ORGANISM: artificial
<220> FEATURE:
<223> OTHER INFORMATION: synthetic oligonucleotide

<400> SEQUENCE: 16
cggagctcga attcggatcc taggacagca gcggcat                              37
```

EXTRACELLULAR PRODUCTION OF DESIGNER HYDROXYALKANOYLOXY ALKANOIC ACIDS WITH RECOMBINANT BACTERIA

CROSS REFERENCE TO RELATED APPLICATIONS

This application claims priority to International Application No. PCT/IB2016/054037, filed on Jul. 6, 2016, entitled EXTRACELLULAR PRODUCTION OF DESIGNER HYDROXYALKANOYLOXY ALKANOIC ACIDS WITH RECOMBINANT BACTERIA, which claims the benefit of European Application No. EP 15175922.2, filed Jul. 8, 2015, the disclosures of which are incorporated herein by reference. Also the entire contents of the ASCII text file entitled "IPM0080US_Sequence_Listing.txt" created on Dec. 21, 2017, having a size of 13 kilobytes is incorporated herein by reference.

FIELD OF THE INVENTION

The present invention relates to a host cell with an rhlA gene under the control of a heterologous promoter that is capable of producing hydroxyalkanoyloxy alkanoic acid (HAA). The invention further relates to methods of producing such a host cell and to the use of said host cell for producing HAA. The present invention also relates to methods of producing hydroxyalkanoyloxy alkanoic acids (HAA) that employs a respective host cell, the use of such a host cell for producing HAA and HAA compositions produced by the host cell. The present invention also provides methods of producing fatty acid compositions, fatty alcohol compositions, or hydrocarbon compositions comprising producing HAA using said host cell, and fatty acid compositions, fatty alcohol compositions, or hydrocarbon compositions produced by said methods.

BACKGROUND OF THE INVENTION

With the goal of diminishing dependency from oil and to turning towards a sustainable chemical industry based on renewable resources, a demand for catalysts, which are able to provide basic chemicals for the chemical industry out of plant resources (e.g. oils or sugars), arises. One important class of said basic chemicals are fatty alcohols. While production of fatty alcohols with higher chain lengths (>C14) out of plant oils is state of the art, the market for short chain fatty alcohols such as C8 or C10 is served by chemical synthesis products from crude oil derivatives. One of the main reasons why short chain fatty alcohols are rarely derived from renewable recourses is that the primarily used oil plants produce oils with longer fatty acids, thus hindering the production of such short chain fatty alcohols. In addition, nearly all oil plants produce a broad product spectrum with the result that a specific production of a narrowly defined fat alcohol composition or even a single fatty alcohol is hampered and is thus connected with high costs.

The annual production of plant oils lies in the range of 140 million tons and market increases are difficult to achieve and will be accompanied by severely negative impact on environment. In contrast, the potential of using sugars is tremendous, as about 790 million tons are easily available and further 800 million tons can be obtained from the timber industry.

One important biosynthetic precursor of fatty alcohols is HAA. HAA can be produced by microbes using sugars as substrate. An HAA molecule consists of a dimer of two hydroxy-fatty acids and thus essentially consists of two hydrocarbon chains. HAA can be synthesized using the enzyme RhlA encoded by the rhlA gene, which catalyzes the production of HAA through linking two hydroxyfatty acids.

HAA can also be used as a precursor for the synthesis of alkanes. Such an alkane composition can be used as fuel, such as aviation fuel. Due to their amphiphilic nature, HAA can also be used as biosurfactant.

The rhlA gene has already been studied in connection with the production of rhamnolipids, which are glycosides with one (mono-rhamnolipid) or two rhamnose-units (di-rhamnolipid) as the glycon portion and one to three 3-hydroxy-fatty acid moieties as the aglycon portion. The rhamnose-moiety and the lipid moiety are linked via an O-glycosidic bond. If a plurality of 3-hydroxy-fatty acid moieties is present, they are linked to each other by an ester bond that involves the 3-hydroxy group(s). The terminal carboxyl group may be a free carboxylic acid group or a methyl ester Rhamnolipids are produced by enzymes encoded by rhlA, rhlB and rhlC. The rhlA and rhlB genes form an operon, encoding 3-hydroxyacyl-ACP O-3-hydroxyacyltransferase and rhamnosyltransferase 1, respectively, while rhlC encodes rhamnosyltransferase 2. RhlC is part of an operon together with a gene (PA1131) of so far unknown function. Rhamnosyltransferase 1A (RhlA) is responsible for the synthesis of the fatty acid dimer moiety of rhamnolipids and free 3-(3-hydroxyalkanoyloxy)alkanoic acids (HAAs), the precursors for rhamnolipid production. Mono-rhamnolipids are then synthesized by Rhamnosyltransferase 1B, which links a rhamnose molecule to a hydroxyalkanoic acid. Rhamnosyltransferase 2 generates di-rhamnolipids by adding a second rhamnose molecule to mono-rhamnolipids. Rhamnolipids have been found to be produced by a number of different bacteria (for an overview see Abdel-Mawgoud, A. M., et al., Appl. Microbiol. Biotechnol (2010) 86, 1323-1336) and potential Rhamnosyltransferase 1 and 2 genes keep being reported.

Currently, no commercial production of HAA is established in the art and only few literature exist that relates to HAA production. Usually, HAA production is reported in connection with synthesis or rhamnolipids, as for example by Dubeau et al. (2009), Cabrera-Valladares et al. (2006) or Lépine et al. (2002). In addition, Williamson et al. (2008) as well as Zhu and Rock (2008) have expressed RhlA in *E. coli* and have reported a low production of HAA. In the latter cases, expressing RhlA merely served the purpose of characterizing said enzyme and a commercial production of HAA has not been envisioned by the authors. Déziel et al (2003) reported on a *P. aeruginosa* strain in which rhlB gene was knocked-out while rhlA gene remained active. A low production of HAA was observed with this strain but again, the purpose of this paper was to study the rhamnolipid synthesis pathway and a commercial production of HAA was not intended. Choi et al (2011) and the corresponding patent application KR/2012/0044192 reports on using a *P. aeruginosa* strain in which rhlB gene was knocked-out for HAA production. A maximum of 700 mg/L has been achieved but only if the fatty acid octanoic was used as carbon source. Compared to the titer described by Déziel et al. (2003), who used sugar as carbon source, the amount of HAA was about three times higher. Consequently, Choi et al. (2011) concluded that fatty acids should be preferred carbon sources. However, 700 mg/L HAA is still a rather low titer for a commercial production.

It is thus an object of the present invention to provide a method of producing HAA and an organism suitable for such a method that when used in HAA production overcomes at least one of the drawbacks of the prior art. This object is solved by the method and and the host cells according to the independent claims.

SUMMARY OF THE INVENTION

The present invention generally relates to a host cell comprising an rhlA gene or an ortholog thereof, being under the control of a heterologous promoter; and wherein said host cell is capable of producing hydroxyalkanoyloxy alkanoic acid (HAA) and achieving an HAA concentration of more than 1 g $L^{-1}$ when cultured.

In some embodiments, the host cell comprises an rhlA gene or an ortholog thereof, being under the control of a heterologous promoter that is as strong or stronger than the promotor having the sequence as set forth in SEQ ID NO: 01 (SynPro8). In some embodiments the host cell is recombinant. In some embodiments, the host cell is a prokaryotic host cell or a yeast host cell. In some embodiments, the host cell is gram-negative.

In some embodiments, the host cell is a *Pseudomonas* sp., a proteobacterium of one of the classes Alphaproteobacteria, Betaproteobacteria, Gammaproteobacteria and Deltaproteobacteria, or an *Acidobacterium* of one of the classes Acidobacteriales and Solibacteres. In some embodiments, the host cell is selected from the group consisting of *Pseudomonas putida, Pseudomonas chlororaphis, Pseudomonas fluorescens, Pseudomonas alcaligenes, Pseudomonas aeruginosa, Pseudomonas cepacia, Pseudomonas clemancea, Pseudomonas collierea, Pseudomonas luteola, Pseudomonas stutzeri, Pseudomonas taiwanensis, Pseudomonas* sp. VLB120, *Pseudomonas teessidea, Escherichia coli, Renibacterium salmoninarum, Cellulomonas cellulans, Tetragenococcus koreensis, Burkholderia glumae, Burkholderia mallei, Burkholderia pseudomallei, Burkholderia plantarii, Burkholderia thailandensis, Acinetobacter calcoaceticus, Enterobacter asburiae, Enterobacter hormaechei, Pantoea stewartii* and *Pantoea ananatis*. In some embodiments, the host cell is non-pathogenic for a human subject.

In some embodiments, the host cell does not comprise an rhlB or an ortholog thereof or an rhlC gene or an ortholog thereof, being under the control of a heterologous promoter. In some embodiments, the host cell is capable of achieving an HAA concentration of more than 1 g $L^{-1}$ in a shaking flask culture. In some embodiments, the host cell is capable of secreting HAA. In some embodiments, the host cell has a knock-out mutation in one or more endogenous sequences encoding for a gene involved in β-oxidation of fatty acids. In some embodiments, the host cell has a knock-out mutation in one or more endogenous sequences encoding for a gene involved in poly(3-hydroxyalkanoates) (PHA) biosynthesis. In some embodiments, a gene encoding for R-specific enoyl-CoA hydratase (such as RhlY or RhlZ, as described by Abdel-Mawgoud et al. 2014) is overexpressed in the host cell.

The present invention also relates to a method of producing an HAA, wherein the method comprises culturing a host cell according to the invention and wherein an HAA concentration of 1 g $L^{-1}$ or more is achieved. In some embodiments, the method comprises recovery or isolation of said HAA.

The present invention also relates to using a host cell of the invention for the production of HAA, wherein 1 g $L^{-1}$ or more HAA is produced. In some embodiments, the mainly produced HAA comprises a fatty acid with a predefined number of carbon atoms, wherein the host cell comprises an rhlA gene that catalyzes the formation of said HAA as a preferred product. In some embodiments, the mainly produced HAA constitutes 30% (w/w) or more of total produced HAA. In some embodiments, a fatty acid with a predefined number of carbon atoms comprised in the HAA produced constitutes 30% (w/w) or more of total fatty acid comprised in the HAA produced.

The present invention also relates to an HAA preparation obtainable by the methods of the invention.

The present invention also relates to a method of producing a host cell of the invention, wherein the host cell is capable of mainly producing HAA comprising a fatty acid with a predefined number of carbon atoms, the method comprising selecting an rhlA gene or ortholog thereof that encodes for a protein that catalyzes the formation of said HAA as a preferred product; and introducing said rhlA gene or ortholog thereof under the control of a heterologous promotor into the cell. The present invention also relates to a host cell obtainable by this.

The present invention also relates to a method of producing a hydroxy fatty acid composition comprising producing an HAA by a method of the invention; and converting the HAA to give a fatty acid composition. The present invention also relates to a fatty acid composition obtainable by this method.

The present invention also relates to a method of producing a fatty alcohol composition comprising producing an HAA by a method of the invention; and converting the HAA to give a fatty alcohol composition. The present invention also relates to a fatty alcohol composition obtainable by this method.

The present invention also relates to a method of producing a hydrocarbon composition comprising producing an HAA by the method of the invention; and converting the HAA to give a hydrocarbon composition. The present invention also relates to a hydrocarbon composition obtainable by this method.

BRIEF DESCRIPTION OF THE DRAWINGS

FIG. 8: Parameters and results from selected HAA production experiments that were carried out with *P. taiwanensis* VLB120 pSB01 and *P. putida* KT2440 pSB01

FIG. 13: Amino acid sequence of RhlA from *Pseudomonas aeruginosa* PAO1 (SEQ ID NO: 06)

FIG. 14: Amino acid sequence of RhlA from *Pantoea ananatis* (SEQ ID NO: 07)

FIG. 15: Amino acid sequence of RhlA from *Burkholderia glumae* (SEQ ID NO: 08)

FIG. 16: Distribution of HAA congeners produced by *E. coli* transformed with different rhlA genes.

BRIEF DESCRIPTION OF THE SEQUENCE LISTING

Figure 1:
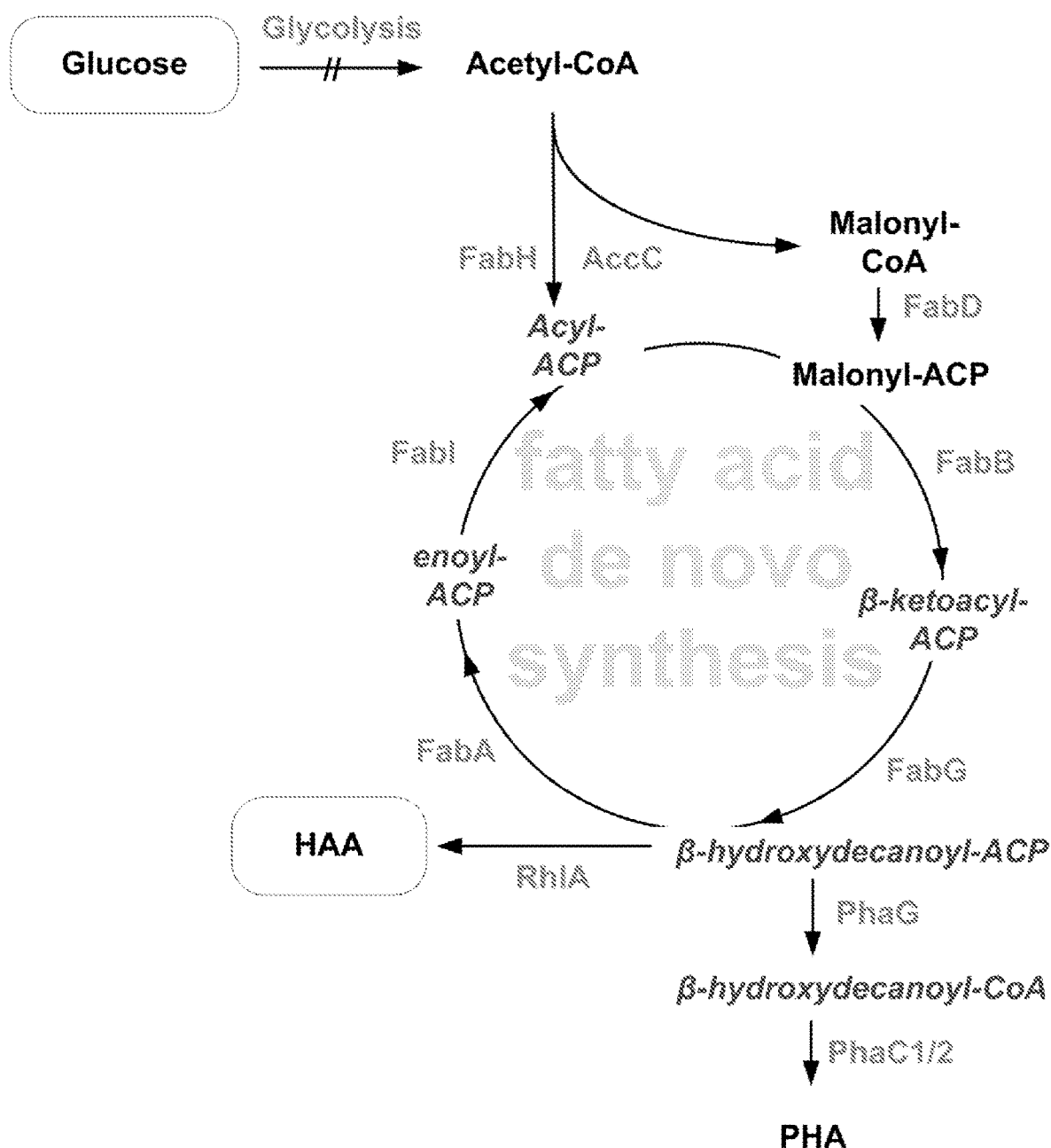
FIG. 1 depicts the HAA synthesis pathway. FabH stands for β-ketoacyl-acyl carrier protein synthase III, ACP stands for acyl carrier protein, AccC stands for acetyl-CoA carboxylase, FabD stands for malonyl-CoA-ACP transacylase, FabBFGZ stands for the enzymes of FabB stands for β-ketoacyl-ACP synthase, FabG stands for β-ketoacyl ACP reductase, FabA stands for β-hydroxyacyl-ACP dehydratase, FabI stands for Enoyl-ACP-reductase, PhaG stands for β-hydroxyacyl-ACP:CoA transacylase, and PhaC1/2 stands for poly(β-hydroxyalkanoate) synthase 1/2.

SEQ ID NO: 01: SynPro 8 promoter sequence (nucleic acid)
SEQ ID NO: 02: Synthetic promoter sequence (nucleic acid)
SEQ ID NO: 03: Synthetic promoter sequence (nucleic acid)
SEQ ID NO: 04: Synthetic promoter sequence (nucleic acid)
SEQ ID NO: 05: Consensus synthetic promoter sequence (nucleic acid)
SEQ ID NO: 06: RhlA from *Pseudomonas aeruginosa* PA01 (amino acid)
SEQ ID NO: 07: RhlA from *Pantoea ananatis* (amino acid)
SEQ ID NO: 08: RhlA from *Burkholderia glumae* (amino acid)
SEQ ID NO: 09: P01 primer (nucleic acid)
SEQ ID NO: 10: P02 primer (nucleic acid)
SEQ ID NO: 11: P03 primer (nucleic acid)
SEQ ID NO: 12: P04 primer (nucleic acid)
SEQ ID NO: 13: P05 primer (nucleic acid)
SEQ ID NO: 14: P06 primer (nucleic acid)
SEQ ID NO: 15: P07 primer (nucleic acid)
SEQ ID NO: 16: P08 primer (nucleic acid)

DETAILED DESCRIPTION OF THE INVENTION

The present invention provides a genetically modified host cell that may be employed for production of hydroxyalkanoyloxy alkanoic acids (HAA) in high titers. This is achieved by expressing rhlA gene that encodes an enzyme which is responsible for the production of HAA under the control of a heterologous promoter which, without being bound by theory, effects preferably such a gene expression level and, thus, increased level of the translation product (protein) of the rhlA gene that the host cell is capable to achieve an HAA concentration of more than 1 g L$^{-1}$ in the culture medium. The rhlA gene encodes the RhlA protein (3-hydroxyacyl-ACP O-3-hydroxyacyltransferase). A host cell according to the invention may thus be a recombinant cell, preferably a bacterial cell. Use of the modified host cell allows production of various HAA.

The present invention provides a host cell, preferably a bacterial host cell. The host cell includes an rhlA gene or an ortholog thereof. The rhlA gene or the ortholog thereof is under the control of a heterologous promoter. The host cell is preferably capable of achieving an HAA concentration of more than 1 g $L^{-1}$, preferably more than 1.1 g $L^{-1}$, preferably more than 1.2 g $L^{-1}$, preferably more than 1.3 g $L^{-1}$, preferably more than 1.4 g $L^{-1}$, preferably more than 1.5 g $L^{-1}$, preferably more than 1.6 g $L^{-1}$, preferably more than 1.7 g $L^{-1}$, preferably more than 1.8 g $L^{-1}$, preferably more than 1.9 g $L^{-1}$, preferably more than 2 g $L^{-1}$, preferably more than 3 g $L^{-1}$, preferably more than 4 g $L^{-1}$, preferably more than 5 g $L^{-1}$, preferably more than 6 g $L^{-1}$, preferably more than 7 g $L^{-1}$, preferably more than 8 g $L^{-1}$, preferably more than 9 g preferably more than 10 g $L^{-1}$, preferably more than 11 g $L^{-1}$, preferably more than 12 g $L^{-1}$, preferably more than 13 g $L^{-1}$, preferably more than 14 g $L^{-1}$, preferably more than 15 g $L^{-1}$, preferably more than 16 g $L^{-1}$, preferably more than 17 g $L^{-1}$, preferably more than 18 g $L^{-1}$, preferably more than 19 g $L^{-1}$, preferably more than 20 g $L^{-1}$ HAA (including all numbers in between) in the culture medium preferably when cultured under suitable conditions.

The prior art did not achieve an HAA concentration in the culture medium of more than 1 g $L^{-1}$ HAA. In particular, Zhu and Rock or Déziel et al. or Choi et al. merely achieved 700 mg $L^{-1}$ or 722 µmol $L^{-1}$ (corresponding to 256 mg $L^{-1}$) or only 169 mg $L^{-1}$ and were not able to suggest a way to increase the HAA titers as was done by the present inventors. Rather, both Déziel et al. as well as Choi et al. teach to use *Pseudomonas aeruginosa* strains, in which rhlB is knocked-out instead of using a host cell which includes an rhlA gene under control of a heterologous promoter. Choi et al. further suggest using octanoic acid instead of sugars as carbon source in order to increase HAA titer. However, the present inventors show that a host cell having an rhlA gene under control of a heterologous promoter is able to successfully solve this problem and achieve HAA concentrations of more than 1 g $L^{-1}$ HAA.

The present inventors have found that uncoupling HAA production, which is mainly governed by the rhlA gene, from its natural regulation and expressing said gene under the control of a heterologous promoter increases HAA production in a host cell. Said heterologous promoter is preferably a strong promoter. This finding is unexpected. However, Choi et al., have not overexpressed rhlA but have knocked-out rhlB. Based on their finding, that using octanoic acid as carbon source increases HAA titers, Choi et al. suggested, that octanoic acid should be used as carbon source. One explanation of this finding may be that the presence of octanoic acid up-regulates expression of rhlA gene in *P. aeruginosa*. However, Choi et al. have not envisioned that expressing rhlA gene under the control of a heterologous promotor will uncouple its expression from its natural regulation. Consequently, according to the present invention, when expressed under control of a heterologous promoter, high HAA titers of 1 g $L^{-1}$ or more can be obtained using a variety of carbon sources, such as for example saccharides.

As indicated above, in the context of the invention a "hydroxyalkanoyloxy alkanoic acid" refers to a dimer of saturated or unsaturated β-hydroxy-carboxylic acid moieties. The first β-hydroxy-carboxylic acid is linked via an ester bond between its 1-carboxy group to the 3-OH group of a second β-hydroxy-carboxylic acid. Thus the carboxylic group of the second carboxylic acid moiety defines the end of the HAA. This carboxylic group of the second β-hydroxy-carboxylic acid may be either a free carboxylic group or it may define an ester with an aliphatic alcohol. It is understood that the β-hydroxy-carboxylic acid moieties are selected independently from each other. Hence, the two β-hydroxy-carboxylic acid moieties may be identical or may be different from each other.

Generally an HAA can be represented by the following formula (I).

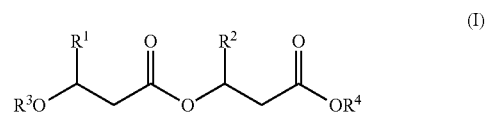

(I)

In this formula, R1 and R2, may be individually selected from a an aliphatic group that has a main chain that has a length from 1 to about 19, such as from 1 to about 17, from 1 to about 15, from 1 to about 13, about 2 to about 13, about 3 to about 13 or about 4 to about 13, including e.g. 2, 3, 4, 5, 6, 7, 8, 9, 10, 11 or 12 carbon atoms. R3 and R4 are independent from each other a hydrogen atom (H) or an aliphatic group that has a main chain of one to about five, such as 2, 3 or 4 carbon atoms.

The term "aliphatic" means, unless otherwise stated, a straight or branched hydrocarbon chain, which may be saturated or mono- or poly-unsaturated and include heteroatoms. The term "heteroatom" as used herein means an atom of any element other than carbon or hydrogen. An unsaturated aliphatic group contains one or more double and/or triple bonds (alkenyl or alkinyl moieties). The branches of the hydrocarbon chain may include linear chains as well as non-aromatic cyclic elements. The hydrocarbon chain, which may, unless otherwise stated, be of any length, and contain any number of branches. Typically, the hydrocarbon (main) chain includes 1 to 5, to 10, to 15 or to 20 carbon atoms. Examples of alkenyl radicals are straight-chain or branched hydrocarbon radicals which contain one or more double bonds. Alkenyl radicals generally contain about two to about twenty carbon atoms and one or more, for instance two, double bonds, such as about two to about ten carbon atoms, and one double bond. Alkynyl radicals normally contain about two to about twenty carbon atoms and one or more, for example two, triple bonds, such as two to ten carbon atoms, and one triple bond. Examples of alkynyl radicals are straight-chain or branched hydrocarbon radicals which contain one or more triple bonds. Examples of alkyl groups are methyl, ethyl, propyl, butyl, pentyl, hexyl, heptyl, octyl, nonyl, decyl, the n isomers of these radicals, isopropyl, isobutyl, isopentyl, sec-butyl, tert-butyl, neopentyl, 3,3-dimethylbutyl. Both the main chain as well as the branches may furthermore contain heteroatoms as for instance N, O, S, Se or Si or a carbon atom may be replaced by one of these heteroatoms. An aliphatic moiety may be substituted or unsubstituted with one or more functional groups. Substituents may be any functional group, as for example, but not limited to, amino, amido, carbonyl, carboxyl, hydroxyl, nitro, thio and sulfonyl.

In typical embodiments, HAA may include only saturated 3-hydroxy-carboxylic acid moieties or may include one or more, e.g. two, unsaturated 3-hydroxy-carboxylic acid moieties. Such an HAA may for instance include a 3-hydroxycarboxylic acid selected from the group consisting of 3-hydroxy-n-hexanoic acid, 3-hydroxy-n-octanoic acid, 3-hydroxy-n-nonanoic acid, 3-hydroxy-n-decanoic acid, 3-hydroxy-n-decenoic acid, 3-hydroxy-n-undecanoic acid, 3-hydroxy-n-dodecanoic acid, 3-hydroxy-n-dodecenoic acid, 3-hydroxy-n-tetradecanoic acid, 3-hydroxy-n-tetradecenoic acid, 3-hydroxy-n-hexadecanoic acid and 3-hydroxy-n-hexadecenoic acid, or a combination of two 3-hydroxycarboxylic acids selected from that group.

In typical embodiments, the HAA according to the invention may be selected from one or more of the following molecules: 3-[(3-hydroxy-n-hexanoyl)oxy]-n-hexanoic acid, 3-[(3-hydroxy-n-hexanoyl)oxy]-n-octanoic acid, 3-[(3-hydroxy-n-hexanoyl)oxy]-n-nonanoic acid, 3-[(3-hydroxy-n-hexanoyl)oxy]-n-decanoic acid, 3-[(3-hydroxy-n-hexanoyl)oxy]-n-decenoic acid, 3-[(3-hydroxy-n-hexanoyl)oxy]-n-undecanoic acid, 3-[(3-hydroxy-n-hexanoyl)oxy]-n-dodecanoic acid, 3-[(3-hydroxy-n-hexanoyl)oxy]-n-dodecenoic acid, 3-[(3-hydroxy-n-hexanoyl)oxy]-n-tetradecanoic acid, 3-[(3-hydroxy-n-hexanoyl)oxy]-n-tetradecenoic acid, 3-[(3-hydroxy-n-hexanoyl)oxy]-n-hexadecanoic acid, 3-[(3-hydroxy-n-hexanoyl)oxy]-n-hexadecenoic acid, 3-[(3-hydroxy-n-octanoyl)oxy]-n-hexanoic acid, 3-[(3-hydroxy-n-octanoyl)oxy]-n-octanoic acid, 3-[(3-hydroxy-n-octanoyl)oxy]-n-nonanoic acid, 3-[(3-hydroxy-n-octanoyl)oxy]-n-decanoic acid, 3-[(3-hydroxy-n-octanoyl)oxy]-n-decenoic acid, 3-[(3-hydroxy-n-octanoyl)oxy]-n-undecanoic acid, 3-[(3-hydroxy-n-octanoyl)oxy]-n-dodecanoic acid, 3-[(3-hydroxy-n-octanoyl)oxy]-n-dodecenoic acid, 3-[(3-hydroxy-n-octanoyl)oxy]-n-tetradecanoic acid, 3-[(3-hydroxy-n-octanoyl)oxy]-n-tetradecenoic acid, 3-[(3-hydroxy-n-octanoyl)oxy]-n-hexadecanoic acid, 3-[(3-hydroxy-n-octanoyl)oxy]-n-hexadecenoic acid, 3-[(3-hydroxy-n-nonanoyl)oxy]-n-hexanoic acid, 3-[(3-hydroxy-n-nonanoyl)oxy]-n-octanoic acid, 3-[(3-hydroxy-n-nonanoyl)oxy]-n-nonanoic acid, 3-[(3-hydroxy-n-nonanoyl)oxy]-n-decanoic acid, 3-[(3-hydroxy-n-nonanoyl)oxy]-n-decenoic acid, 3-[(3-hydroxy-n-nonanoyl)oxy]-n-undecanoic acid, 3-[(3-hydroxy-n-nonanoyl)oxy]-n-dodecanoic acid, 3-[(3-hydroxy-n-nonanoyl)oxy]-n-dodecenoic acid, 3-[(3-hydroxy-n-nonanoyl)oxy]-n-tetradecanoic acid, 3-[(3-hydroxy-n-nonanoyl)oxy]-n-tetradecenoic acid, 3-[(3-hydroxy-n-nonanoyl)oxy]-n-hexadecanoic acid, 3-[(3-hydroxy-n-nonanoyl)oxy]-n-hexadecenoic acid, 3-[(3-hydroxy-n-decanoyl)oxy]-n-hexanoic acid, 3-[(3-hydroxy-n-decanoyl)oxy]-n-octanoic acid, 3-[(3-hydroxy-n-decanoyl)oxy]-n-nonanoic acid, 3-[(3-hydroxy-n-decanoyl)oxy]-n-decanoic acid, 3-[(3-hydroxy-n-decanoyl)oxy]-n-decenoic acid, 3-[(3-hydroxy-n-decanoyl)oxy]-n-undecanoic acid, 3-[(3-hydroxy-n-decanoyl)oxy]-n-dodecanoic acid, 3-[(3-hydroxy-n-decanoyl)oxy]-n-dodecenoic acid, 3-[(3-hydroxy-n-decanoyl)oxy]-n-tetradecanoic acid, 3-[(3-hydroxy-n-decanoyl)oxy]-n-tetradecenoic acid, 3-[(3-hydroxy-n-decanoyl)oxy]-n-hexadecanoic acid, 3-[(3-hydroxy-n-decanoyl)oxy]-n-hexadecenoic acid, 3-[(3-hydroxy-n-decenoyl)oxy]-n-hexanoic acid, 3-[(3-hydroxy-n-decenoyl)oxy]-n-octanoic acid, 3-[(3-hydroxy-n-decenoyl)oxy]-n-nonanoic acid, 3-[(3-hydroxy-n-decenoyl)oxy]-n-decanoic acid, 3-[(3-hydroxy-n-decenoyl)oxy]-n-decenoic acid, 3-[(3-hydroxy-n-decenoyl)oxy]-n-undecanoic acid, 3-[(3-hydroxy-n-decenoyl)oxy]-n-dodecanoic acid, 3-[(3-hydroxy-n-decenoyl)oxy]-n-dodecenoic acid, 3-[(3-hydroxy-n-decenoyl)oxy]-n-tetradecanoic acid, 3-[(3-hydroxy-n-decenoyl)oxy]-n-tetradecenoic acid, 3-[(3-hydroxy-n-decenoyl)oxy]-n-hexadecenoic acid, 3-[(3-hydroxy-n-undecanoyl)oxy]-n-hexanoic acid, 3-[(3-hydroxy-n-undecanoyl)oxy]-n-octanoic acid, 3-[(3-hydroxy-n-undecanoyl)oxy]-n-nonanoic acid, 3-[(3-hydroxy-n-undecanoyl)oxy]-n-decanoic acid, 3-[(3-hydroxy-n-undecanoyl)oxy]-n-decenoic acid, 3-[(3-hydroxy-n-undecanoyl)oxy]-n-undecanoic acid, 3-[(3-hydroxy-n-undecanoyl)oxy]-n-dodecanoic acid, 3-[(3-hydroxy-n-undecanoyl)oxy]-n-dodecenoic acid, 3-[(3-hydroxy-n-undecanoyl)oxy]-n-tetradecanoic acid, 3-[(3-hydroxy-n-undecanoyl)oxy]-n-tetradecenoic acid, 3-[(3-hydroxy-n-undecanoyl)oxy]-n-hexadec anoic acid, 3-[(3-hydroxy-n-undecanoyl)oxy]-n-hexadecenoic acid, 3-[(3-hydroxy-n-dodecanoyl)oxy]-n-hexanoic acid, 3-[(3-hydroxy-n-dodecanoyl)oxy]-n-octanoic acid, 3-[(3-hydroxy-n-dodecanoyl)oxy]-n-nonanoic acid, 3-[(3-hydroxy-n-dodecanoyl)oxy]-n-decanoic acid, 3-[(3-hydroxy-n-dodecanoyl)oxy]-n-decenoic acid, 3-[(3-hydroxy-n-dodecanoyl)oxy]-n-undecanoic acid, 3-[(3-hydroxy-n-dodecanoyl)oxy]-n-dodecanoic acid, 3-[(3-hydroxy-n-dodecanoyl)oxy]-n-dodecenoic acid, 3-[(3-hydroxy-n-dodecanoyl)oxy]-n-tetradec anoic acid, 3-[(3-hydroxy-n-dodecanoyl)oxy]-n-tetradecenoic acid, 3-[(3-hydroxy-n-dodecanoyl)oxy]-n-hexadecanoic acid, 3-[(3-hydroxy-n-dodecanoyl)oxy]-n-hexadecenoic acid, 3-[(3-hydroxy-n-dodecenoyl)oxy]-n-hexanoic acid, 3-[(3-hydroxy-n-dodecenoyl)oxy]-n-octanoic acid, 3-[(3-hydroxy-n-dodecenoyl)oxy]-n-nonanoic acid, 3-[(3-hydroxy-n-dodecenoyl)oxy]-n-decanoic acid, 3-[(3-hydroxy-n-dodecenoyl)oxy]-n-decenoic acid, 3-[(3-hydroxy-n-dodecenoyl)oxy]-n-undecanoic acid, 3-[(3-hydroxy-n-dodecenoyl)oxy]-n-dodecanoic acid, 3-[(3-hydroxy-n-dodecenoyl)oxy]-n-dodecenoic acid, 3-[(3-hydroxy-n-dodecenoyl)oxy]-n-tetradecanoic acid, 3-[(3-hydroxy-n-dodecenoyl)oxy]-n-tetradecenoic acid, 3-[(3-hydroxy-n-dodecenoyl)oxy]-n-hexadecanoic acid, 3-[(3-hydroxy-n-dodecenoyl)oxy]-n-hexadecenoic acid, 3-[(3-hydroxy-n-tetradecanoyl)oxy]-n-hexanoic acid, 3-[(3-hydroxy-n-tetradecanoyl)oxy]-n-octanoic acid, 3-[(3-hydroxy-n-tetradecanoyl)oxy]-n-nonanoic acid, 3-[(3-hydroxy-n-tetradecanoyl)oxy]-n-decanoic acid, 3-[(3-hydroxy-n-tetradecanoyl)oxy]-n-decenoic acid, 3-[(3-hydroxy-n-tetradecanoyl)oxy]-n-undecanoic acid, 3-[(3-hydroxy-n-tetradecanoyl)oxy]-n-dodecanoic acid, 3-[(3-hydroxy-n-tetradecanoyl)oxy]-n-dodecenoic acid, 3-[(3-hydroxy-n-tetradecanoyl)oxy]-n-tetradec anoic acid, 3-[(3-hydroxy-n-tetradecanoyl)oxy]-n-tetradecenoic acid, 3-[(3-hydroxy-n-tetradecanoyl)oxy]-n-hexadecanoic acid, 3-[(3-hydroxy-n-tetradecanoyl)oxy]-n-hexadecenoic acid, 3-[(3-hydroxy-n-tetradecenoyl)oxy]-n-hexanoic acid, 3-[(3-hydroxy-n-tetradecenoyl)oxy]-n-octanoic acid, 3-[(3-hydroxy-n-tetradecenoyl)oxy]-n-nonanoic acid, 3-[(3-hydroxy-n-tetradecenoyl)oxy]-n-decanoic acid, 3-[(3-hydroxy-n-tetradecenoyl)oxy]-n-decenoic acid, 3-[(3-hydroxy-n-tetradecenoyl)oxy]-n-undecanoic acid, 3-[(3-hydroxy-n-tetradecenoyl)oxy]-n-dodecanoic acid, 3-[(3-hydroxy-n-tetradecenoyl)oxy]-n-dodecenoic acid, 3-[(3-hydroxy-n-tetradecenoyl)oxy]-n-tetradecanoic acid, 3-[(3-hydroxy-n-tetradecenoyl)oxy]-n-tetradecenoic acid, 3-[(3-hydroxy-n-tetradecenoyl)oxy]-n-hexadecanoic acid, 3-[(3-hydroxy-n-tetradecenoyl)oxy]-n-hexadecenoic acid, 3-[(3-hydroxy-n-hexadecanoyl)oxy]-n-hexanoic acid, 3-[(3-hydroxy-n-hexadecanoyl)oxy]-n-octanoic acid, 3-[(3-hydroxy-n-hexadecanoyl)oxy]-n-nonanoic acid, 3-[(3-hydroxy-n-hexadecanoyl)oxy]-n-decanoic acid, 3-[(3-hydroxy-n-hexadecanoyl)oxy]-n-decenoic acid, 3-[(3-hydroxy-n-hexadecanoyl)oxy]-n-undecanoic acid, 3-[(3-hydroxy-n- hexadecanoyl)oxy]-n-dodec anoic acid, 3-[(3-hydroxy-n-hexadecanoyl)oxy]-n-dodecenoic acid, 3-[(3-hydroxy-n-hexadecanoyl)oxy]-n-tetradecanoic acid, 3-[(3-hydroxy-n-hexadecanoyl)oxy]-n-tetradecenoic acid, 3-[(3-hydroxy-n-hexadecanoyl)oxy]-n-hexadecanoic acid, 3-[(3-hydroxy-n-hexadecanoyl)oxy]-n-hexadecenoic acid, 3-[(3-hydroxy-n-hexadecenoyl)oxy]-n-hexanoic acid, 3-[(3-hydroxy-n-hexadecenoyl)oxy]-n-octanoic acid, 3-[(3-hydroxy-n-hexadecenoyl)oxy]-n-nonanoic acid, 3-[(3-hydroxy-n-hexadecenoyl)oxy]-n-decanoic acid, 3-[(3-hydroxy-n-hexadecenoyl)oxy]-n-decenoic acid, 3-[(3-hydroxy-n-hexadecenoyl)oxy]-n-undecanoic acid, 3-[(3-hydroxy-n-hexadecenoyl)oxy]-n-dodecanoic acid, 3-[(3-hydroxy-n-hexadecenoyl)oxy]-n-dodecenoic acid, 3-[(3-hydroxy-n-hexadecenoyl)oxy]-n-tetradecanoic acid, 3-[(3-hydroxy-n-hexadecenoyl)oxy]-n-tetradecenoic acid, 3-[(3-hydroxy-n-hexadecenoyl)oxy]-n-hexadecanoic acid, 3-[(3-hydroxy-n-hexadecenoyl)oxy]-n-hexadecenoic acid and any mixture thereof.

An HAA is an amphiphilic compound. The amphiphilic properties of an HAA are due to the presence of both polar and non-polar moieties, i.e. hydroxy- and carboxy groups as well as a hydrocarbon chain that does not carry a functional group, within the same molecule. In this regard an HAA is generally of surfactant nature. Due to their amphiphilic nature, HAA produced by the host cells of the present invention can be used as detergents in washing agents as emulsifiers in the cosmetic and food industry.

The HAA may have a net charge at physiological pH. The term "physiological pH" is known to those in the art to refer to the pH value of blood, which has typically a pH value of about 7.4. In embodiments where the HAA has a free terminal carboxylic acid group the HAA may have a negative net charge of −1 at physiological pH. In embodiments where the HAA has a terminal ester group the HAA may be of neutral net charge and may thus be defined as having no net charge at physiological pH.

HAA produced by the host cell of the present invention may be subject to modifications by enzymes that are capable to modify HAA, such as esterases. In particular, enzymes that are capable to modify HAA are preferably used to modify HAA after they have been synthesized. More particularly, these enzymes can break up ester linkages in order to modify the HAA as is desired.

A host cell of the present invention includes any suitable host cell that is capable of producing HAA. Accordingly, the present invention envisages as a host cell preferably non-pathogenic host cells (non-pathogenic for humans) including a unicellular host cell such as a fungal host cell, for example, a yeast. Preferably, however, the host cell of the present invention is a bacterial host cell including non-pathogenic bacterial host cells such as bacterial host cells capable of producing HAA.

A host cell according to the invention includes an rhlA gene or an ortholog thereof. The rhlA gene or the respective ortholog is under the control of a heterologous promoter. In some embodiments the rhlA gene is an endogenous gene of the host cell. In some embodiments the rhlA gene is a heterologous gene.

The heterologous promoter, which may also be addressed as "exogenous" promoters, to which the rhlA gene is operationally linked may be any desired promoter. The term "promoter" as used herein, refers to a nucleic acid sequence needed for gene sequence expression. Promoter regions vary from organism to organism, but are well known to persons skilled in the art for different organisms. For example, in prokaryotes, the promoter region contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence or the CAAT sequence. "Heterologous" when used in the context of a promoter that drives expression of, for instance, an rhlA gene as described herein means that the promoter is not from the host cell in which it is/will be active, i.e., it is/was not isolated from and/or does naturally occur in said host cell where it is/will be active, e.g., the promoter may be an artificial or synthetic promoter that will be active in a host cell of the invention. Such a promoter is typically neither isolated from the host cell nor does it naturally occur therein. A heterologous promoter can be introduced before the rhlA gene into the genome of a host cell which may naturally harbour these gens or the heterologous promoter may be in front of the rhlA gene(s) which may be inserted as expression cassette/unit into the genome of a host cell. Also, the expression cassettes may be harboured by an extrachromosomal element that is capable of free replication such as a plasmid that is capable of replication, e.g. either as low copy, or medium copy, or high copy plasmid. The term "heterologous" may also refer to the relationship between two or more nucleic acid or protein sequences that are derived from different sources. For example, a promoter is heterologous with respect to a transcribable polynucleotide sequence if such a combination is not normally found in nature. In addition, a particular sequence may be "heterologous" with respect to a host cell in that it encodes a protein or is included in a protein, for example a recombinant protein, that is not normally expressed by the host cell. Such a heterologous protein accordingly generally is or has been inserted into the respective host cell, tissue, or species. Accordingly, a heterologous promoter is not normally coupled in vivo transcriptionally to the coding sequence of the rhlA gene. In the context of the present invention, the term "heterologous" when used in combination with "promoter" can either refer to a promoter that is heterologous to the host organism or to a promoter that is heterologous to the respective transcribable polynucleotide sequence. Preferably, the term as used herein refers to a promoter that is both, heterologous to the host organism and to the respective transcribable polynucleotide sequence.

Two nucleic acid sequences (such as a promoter region sequence and a sequence encoding a RhlA protein) are said to be operably linked if the nature of the linkage between the two DNA sequences does not (1) result in the introduction of a frame-shift mutation, (2) interfere with the ability of the promoter region sequence to direct the transcription of e.g. said gene sequence encoding a acyltransferase, or (3) interfere with the ability of e.g. said gene sequence of a acyltransferase to be transcribed by the promoter region sequence.

Thus, a promoter region would be operably linked to a DNA sequence if the promoter were capable of effecting transcription of that DNA sequence. Thus, to express e.g. an rhlA gene, transcriptional and translational signals recognized by the host are necessary.

In some embodiments the heterologous promoter is a strong promoter. A strong promoter may for example be selected according to the approach disclosed by Dekhtyar et al. (Biotechnol Left (2010) 32, 243-248) or according to the approach disclosed by Eskin et al. (Pacific Symposium on Biocomputing (2003) 8, 29-40). A preferred heterologous promoter is one which confers an strong expression as the synthetic promoter SynPro8, which has the sequence AGCTCTTGACAAGGTCGGAAAATT-GAAGTATAATATCAGT (SEQ ID NO: 01), preferred are also stronger promoters.

A "stronger (higher) expression than the SynPro8 promoter" means that when rhlA gene, in particular those described in Example 6, i.e., the rhlA gene from *P. aeruginosa* PAO1, are driven by a promoter in a host cell, in particular in *P. putida* KT2440 or *P. taiwanensis* VLB120, at least 1 g preferably at least 1.1 g $L^{-1}$, preferably at least 1.2 g $L^{-1}$, preferably at least 1.3 g $L^{-1}$, preferably at least 1.4 g $L^{-1}$, preferably at least 1.5 g $L^{-1}$, preferably at least 1.6 g $L^{-1}$, preferably at least 1.7 g $L^{-1}$, preferably at least 1.8 g $L^{-1}$, preferably at least 1.9 g $L^{-1}$, preferably at least 2 g $L^{-1}$, preferably at least 3 g $L^{-1}$, preferably at least 4 g $L^{-1}$, preferably at least 5 g $L^{-1}$, preferably at least 6 g $L^{-1}$, preferably at least 7 g $L^{-1}$, preferably at least 8 g $L^{-1}$, preferably at least 9 g $L^{-1}$, preferably at least 10 g $L^{-1}$ of one or more HAA (the sum of total HAA, irrespective which HAA) are produced by said host cell under the conditions described in particular in Example 6. Additionally or alternatively, a preferred heterologous promoter confers preferably an expression of an rhlA gene or an ortholog thereof that leads to a maximal theoretical value of HAA production with glucose, glycerol, xylose, or a mixture of glucose and xylose as sole carbon source as described herein. Further particularly preferred promoters are shown in SEQ ID NOs: 01, 02, 03 or 04. A still further particularly preferred promoter sequence is shown in SEQ ID NO: 05 (consensus promoter sequence). Strength of expression can, for example, be determined by the amount/yield of HAA production as described herein and/or by quantitative reverse transcriptase PCR (qRT-PCR) as described in the appended Examples.

Other preferred promoters are synthetic promoters generated by using synthetic degenerated primers as described, for example, in U.S. Pat. No. 7,199,233 and US 2006/0014146. In some embodiments, the promoter strength may be tuned to be appropriately responsive to activation or inactivation. Yet in other embodiments, the promoter strength is tuned to constitutively allow an optimal level of expression of a gene of interest or of a plurality of gene of interest. A preferred example of a synthetic promoter has the following consensus sequence (the sequence is shown from 5' to 3', the last nucleotide at the 3' is immediately before the start codon):

```
                                           (SEQ ID NO: 05)
(A/T/G)(G/T/A)(C/T/G)(T/C/A/G)(C/G)TTGACA(A/T/C)

(G/T/A)(G/C)(T/C/G)(C/T)(G/A/T)(G/T/C)(A/T/G)

(A/T/G)(A/T/C/G)(A/C/T)(T/G/A)(T/C/G)(G/C)(A/T/C)

(A/T/C)(G/T)TATAAT(A/G/T)(T/A/C)(C/A/T)(A/T/G/C)

(G/C)(T/G/C).
```

Other particularly promoter sequences have the following sequences: TTTCCTTGACAAGCCTAGTTTCGCCATT-TATAATGACTCG (SEQ ID NO: 02), GGTGGTTGACAT-TGGCATTACAACGTATTATAATTTAGCG (SEQ ID NO: 03) or TAGAGTTGACACACCTTCGGGTGGGCCT-TATAATACTCGC (SEQ ID NO: 04). All sequences are shown from 5' to 3', the last nucleotide at the 3' is immediately before the start codon).

The heterologous promoter may also be equipped with a regulatory sequence/element that makes the promoter inducible and/or repressible. The promotor may be a non-viral promotor or a non-T7 promoter or a non-T5 promoter, for instance a prokaryotic or synthetic promoter. The promoter may be inducible or may be non-inducible or constitutive.

A host cell according to the invention may preferably not comprise an rhlB gene or an ortholog thereof under control of a heterologous promoter or may preferably not comprise an rhlB gene or an ortholog thereof. Similarly, according to the invention, the host cell may preferably not comprise an rhlC gene or an ortholog thereof under control of a heterologous promoter or may preferably not comprise an rhlC gene or an ortholog thereof.

An ortholog of rhlA encodes a protein having 3-hydroxyacyl-ACP O-3-hydroxyacyltransferase activity, an ortholog of rhlB a protein having rhamnosyltransferase I activity and an ortholog of rhlC gene encodes a protein having rhamnosyltransferase II activity. These activities are well known in the art and are explained in WO 2012/013554 on pages 4 and 5. Similarly, an otholog of RhlA, RhlB or RhlC has 3-hydroxyacyl-ACP O-3-hydroxyacyltransferase activity, rhamnosyltransferase I activity, and rhamnosyltransferase II activity, respectively.

A wide variety of transcriptional and translational regulatory sequences may be employed, depending upon the nature of the host, as long as a desired titer of HAA is obtained. The transcriptional and translational regulatory signals may be derived from viral sources, such as adenovirus, bovine papilloma virus, cytomegalovirus or simian virus, where the regulatory signals are associated with a particular gene sequence which has a high level of expression. Alternatively, promoters from mammalian expression products, such as actin, collagen and myosin may be employed. Transcriptional initiation regulatory signals may be selected which allow for repression or activation, so that expression of the gene sequences can be modulated. Of interest may in some embodiments also be regulatory signals which are temperature-sensitive so that by varying the temperature, expression can be repressed or initiated, or are subject to chemical (such as metabolite) regulation.

A nucleic acid molecule encoding an rhlA gene or an ortholog thereof and an operably linked promoter may be introduced into a recipient (e.g. prokaryotic) host cell either as a nonreplicating DNA or RNA molecule, which may be a linear molecule or a closed covalent circular molecule. Since such molecules are incapable of autonomous replication, the expression of the gene may occur through the transient expression of the introduced sequence. Alternatively, permanent expression may occur through the integration of the introduced DNA sequence into the host chromosome.

A vector may be employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of mRNA. These elements may include splice signals, as well as transcription promoters, enhancers, and termination signals.

The introduced nucleic acid molecule can be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. In some embodiments of the present invention, the *E. coli* BL21(DE3) transformed with a pET28 (Novagen) comprising rhlA gene from *P. aeruginosa* that is described in Zhu and Rock (2008) is excluded from the host cells of the invention. In some embodiments of the present invention, the *E. coli* BL21(DE3) transformed with a with a pBluescript II KS$^+$ comprising the rhlA from *P. aeruginosa* that is described in Zhu and Rock (2008) is excluded from the host cells of the present invention. In some embodiments, the *E. coli* ER2566 transformed with a pQE-80L plasmid (QIAGEN) comprising rhlA gene from *Serratia* 39006 (also named pNRW93) that is described in Williamson et al. (2008) is excluded from the host cells of the invention. In some embodiments, the *Erwinia carotovora* ssp. *Atroseptica* SCRI1043 transformed with a pQE-80L plasmid (QIAGEN) comprising rhlA gene from *Serratia* 39006 that is described in Williamson et al. (2008) is excluded from the host cells of the invention. In some embodiments, the *E. coli* DH5α transformed with a pTrc99A plasmid comprising rhlA gene from *P. aeruginosa* (also named pUO92) that is described in Ochsner et al. (1994) is excluded from the host cells of the present invention. In some embodiments, the *E. coli* XL1-Blue transformed with a pTrc99A plasmid comprising rhlA gene from *P. aeruginosa* (also named pUO92) that is described in Ochsner et al. (1994) is excluded from the host cells of the present invention. In some embodiments, host cells comprising a rhlA gene under control of a heterologous promotor that are described in Zhu and Rock (2008) or Williamson et al. (2008) or Ochsner et al. (1994) are excluded from the host cells of the invention. In some embodiments, host cells comprising a vector selected from the group consisting of: the pET28 (Novagen) comprising rhlA gene from *P. aeruginosa* that is described by Zhu and Rock (2008); the pBluescript II KS$^+$ comprising rhlA gene from *P. aeruginosa* that is described by Zhu and Rock (2008); the pQE-80L plasmid (QIAGEN) comprising rhlA gene from *Serratia* 39006 that is described by Williamson et al. (2008), the pTrc99A plasmid comprising rhlA gene from *P. aeruginosa* that is described in Ochsner et al. (1994), and the pUCP19 pasmid comprising rhlA gene from *P. aeruginosa* that is described in Ochsner et al. (1994) are excluded from the host cells of the invention.

An illustrative example of a prokaryotic vector is a plasmid, such as a plasmid capable of replication in *E. coli* (such as, for example, pBR322, ColEl, pSC101, pACYC 184, VX). *Bacillus* plasmids include pC194, pC221, pT127, and the like. Suitable *Streptomyces* plasmids include p1J101 (Kendall et al., J. Bacteriol. (1987) 169, 4177-4183), and *streptomyces* bacteriophages such as C31. *Pseudomonas* plasmids are for instance reviewed by John et al. (Rev. Infect. Dis. 8:693-704, 1986).

Once the vector or nucleic acid molecule that contains the construct(s) has been prepared for expression, the DNA construct(s) may be introduced into the host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene(s) results in the production of a 3-hydroxyacyl-ACP O-3-hydroxyacyltransferase of the invention, or fragments thereof. This can take place in the transformed cells as such, or following the induction of protein expression.

The terms "expression" and "expressed", as used herein, are used in their broadest meaning, to signify that a sequence included in a nucleic acid molecule and encoding a peptide/protein is converted into its peptide/protein product. Thus, where the nucleic acid is DNA, expression refers to the transcription of a sequence of the DNA into RNA and the translation of the RNA into protein. Where the nucleic acid is RNA, expression may include the replication of this RNA into further RNA copies and/or the reverse transcription of the RNA into DNA and optionally the transcription of this DNA into further RNA molecule(s). In any case expression of RNA includes the translation of any of the RNA species provided/produced into protein. Hence, expression is performed by translation and includes one or more processes selected from the group consisting of transcription, reverse transcription and replication. Expression of the protein or peptide may generally also be carried out using an in vitro expression system. Such an expression system may include a cell extract, typically from bacteria, rabbit reticulocytes or wheat germ. Many suitable systems are commercially available. A nucleic acid molecule, such as DNA, is said to be "capable of expressing" a peptide/protein if it contains nucleotide sequences which contain transcriptional and translational regulatory information and such sequences are operably linked to nucleotide sequences which encode the polypeptide. A suitable embodiment for expression purposes is the use of a vector, in particular an expression vector. Thus, the present invention also provides a host cell transformed/transfected with an expression vector.

An expression vector, which may include one or more regulatory sequences and be capable of directing the expression of nucleic acids to which it is operably linked. An operable linkage is a linkage in which a coding nucleotide sequence of interest is linked to one or more regulatory sequence(s) such that expression of the nucleotide sequence sought to be expressed can be allowed. Thus, a regulatory sequence operably linked to a coding sequence is capable of effecting the expression of the coding sequence, for instance in an in vitro transcription/translation system or in a cell when the vector is introduced into the cell. A respective regulatory sequence need not be contiguous with the coding sequence, as long as it functions to direct the expression thereof. Thus, for example, intervening untranslated yet transcribed sequences may be present between a promoter sequence and the coding sequence and the promoter sequence can still be considered "operably linked" to the coding sequence.

The term "regulatory sequence" includes controllable transcriptional promoters, operators, enhancers, silencers, transcriptional terminators, 5' and 3' untranslated regions which interact with host cellular proteins to carry out transcription and translation and other elements that may control gene expression including initiation and termination codons. The regulatory sequences can be native (homologous), or can be foreign (heterologous) to the cell and/or the nucleotide sequence that is used. The precise nature of the regulatory sequences needed for gene sequence expression may vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence or CAAT sequence. These regulatory sequences are generally individually selected for a certain embodiment, for example for a certain cell to be used. The skilled artisan will be aware that proper expression in a prokaryotic cell also requires the presence of a ribosome-binding site upstream of the gene sequence-encoding sequence.

The term "transfecting" defines a number of methods to insert a nucleic acid vector or other nucleic acid molecules into a cellular organism. These methods involve a variety of techniques, such as treating the cells with high concentrations of salt, an electric field, detergent, or DMSO to render the outer membrane or wall of the cells permeable to nucleic acid molecules of interest or use of various viral transduction strategies.

The term "rhlA gene" includes variants. The term "variant" or "altered" in reference to a nucleic acid or polypeptide refers to polymorphisms, i.e. the exchange, deletion, or insertion of one or more nucleotides or amino acids, respectively, compared to the predominant form of the respective nucleic acid or polypeptide. In the context of the present invention, a variant in some embodiments refers to a contiguous sequence of at least about 50, such as about 100, about 200, or about 300 amino acids set forth in the amino acid sequence of a protein named herein, or the corresponding full-length amino acid sequence, with the proviso that said alteration is included in the respective amino acid sequence. In case the mutation leads to a premature stop codon in the nucleotide sequence encoding the protein, the sequence may even be shorter than the corresponding wild type protein. As a rough guidance, 3-hydroxyacyl-ACP O-3-hydroxyacyltransferase typically has an amino acid sequence with a length of about 200 to about 400, such as about 250 to about 350 amino acids. The 3-hydroxyacyl-ACP O-3-hydroxyacyltransferase polypeptide can be encoded by a full-length nucleic acid sequence, i.e. the complete coding sequence of the respective gene, or any portion of the full-length nucleic acid sequence, as long as the alteration of the polypeptide is retained.

Without being bound by theory, it is speculated that placing an rhlA gene under the control of a heterologous promoter overcomes a major barrier in terms of high expression of HAA during fermentation. The endogenous promoters of the rhlA gene of a bacterial cell are subject to control of expression activity by signaling pathways. The inventors have found that the use of heterologous promoters avoids this signaling regulation. For *P. aeruginosa* the pathways controlling expression of rhamnolipids has been well characterized (for an overview see e.g. Daniels, R., FEMS Microbiology Reviews (2004) 28, 261-289). The expression of all three genes involved in rhamnolipid synthesis, i.e. the rhlA gene, the rhlB gene and the rhlC gene, is transcriptionally regulated by two hierarchical "quorum sensing" systems. Quorum sensing is a general term characterising a specific type of regulation of bacterial gene expression that operates under conditions of high cell density of the bacterial population. It can be taken to represent a form of communication between cells belonging to the same or different species, genera, and even families. This "social" behaviour is widespread among bacteria of various taxonomic groups and promotes the survival of bacteria under alternating environmental conditions. Signaling in quorum sensing is initiated by the action of low-molecular weight regulators, readily diffusible through the cytoplasmic membrane, and receptor proteins, which interact with these regulators.

The amino acid sequence of an RhlA variant is substantially similar to a known RhlA sequence such as a sequence of the RhlA from *Pseudomonas aeruginosa* PAO1 (SEQ ID NO: 06), with SwissProt accession no. Q51559 (30 Nov. 2010, version 60). A sequence that is substantially similar to RhlA will in some embodiments have at at least 30%, preferably at least 35%, preferably at least 40%, preferably at least 45%, preferably at least 50%, preferably at least 55%, preferably at least 60%, preferably at least 65%, preferably at least 70%, have preferably at least 75%, preferably at least 80%, have preferably at least 85%, preferably at least 90% identity, preferably at least 95%, preferably at least 97%, preferably at least 98%, preferably at least 99%, preferably at least 99.5% identity to the sequence of a known RhlA, with the proviso that the altered position or sequence is retained.

The amino acid sequence of an RhlA variant is substantially similar to a known RhlA sequence such as a sequence of the RhlA from *Pantoea ananatis* (SEQ ID NO: 07). A sequence that is substantially similar to RhlA will in some embodiments have at least 30%, preferably at least 35%, preferably at least 40%, preferably at least 45%, preferably at least 50%, preferably at least 55%, preferably at least 60%, preferably at least 65%, preferably at least 70%, have preferably at least 75%, preferably at least 80%, have preferably at least 85%, preferably at least 90% identity, preferably at least 95%, preferably at least 97%, preferably at least 98%, preferably at least 99%, preferably at least 99.5% identity to the sequence of a known RhlA, with the proviso that the altered position or sequence is retained.

The amino acid sequence of an RhlA variant is substantially similar to a known RhlA sequence such as a sequence of the RhlA from *Burkholderia glumae* PG1 (SEQ ID NO: 08). A sequence that is substantially similar a RhlA will in some embodiments have at least 30%, preferably at least 35%, preferably at least 40%, preferably at least 45%, preferably at least 50%, preferably at least 55%, preferably at least 60%, preferably at least 65%, preferably at least 70%, have preferably at least 75%, preferably at least 80%, have preferably at least 85%, preferably at least 90% identity, preferably at least 95%, preferably at least 97%, preferably at least 98%, preferably at least 99%, preferably at least 99.5% identity to the sequence of a known RhlA, with the proviso that the altered position or sequence is retained. Although all three RhlA from *Pseudomonas aeruginosa* PA01, *Pantoea ananatis*, and *Burkholderia glumae* are preferred, the RhlA from *Pseudomonas aeruginosa* PA01 is even more preferred.

By "identity" is meant a property of sequences that measures their similarity or relationship. Identity is measured by dividing the number of identical residues by the total number of residues and gaps and multiplying the product by 100. Preferably, identity is determined over the entire length of the sequences being compared. "Gaps" are spaces in an alignment that are the result of additions or deletions of amino acids. Thus, two copies of exactly the same sequence have 100% identity, but sequences that are less highly conserved, and have deletions, additions, or replacements, may have a lower degree of identity. Those skilled in the art will recognize that several computer programs are available for determining sequence identity using standard parameters, for example Blast (Altschul, et al. (1997) Nucleic Acids Res. 25:3389-3402), Blast2 (Altschul, et al. (1990) J. Mol. Biol. 215:403-410), and Smith- Waterman (Smith, et al. (1981) J. Mol. Biol. 147:195-197). The term "mutated" or "mutant" in reference to a nucleic acid or a polypeptide refers to the exchange, deletion, or insertion of one or more nucleotides or amino acids, respectively, compared to the naturally occurring nucleic acid or polypeptide. The term "altered" or "variant" in reference to a nucleic acid or polypeptide refers to polymorphisms, i.e. the exchange, deletion, or insertion of one or more nucleotides or amino acids, respectively, compared to the predominant form of the respective nucleic acid or polypeptide.

The term "position" when used in accordance with the disclosure means the position of either an amino acid within an amino acid sequence depicted herein or the position of a nucleotide within a nucleic acid sequence depicted herein. The term "corresponding" as used herein also includes that a position is not only determined by the number of the preceding nucleotides/amino acids, but is rather to be viewed in the context of the circumjacent portion of the sequence. Accordingly, the position of a given amino acid in accordance with the disclosure which may be substituted may vary due to deletion or addition of amino acids elsewhere in a (mutant or wild-type) sequence. In this regard it is also noted that data base entries on a nucleic acid sequence of a RhlA may vary in their coverage of non-translated regions, thereby identifying different nucleic acid positions, even though the length of the coding region is unchanged/the same. Similarly, the position of a given nucleotide in accordance with the present disclosure which may be substituted may vary due to deletions or additional nucleotides elsewhere in a non-translated region of a sequence, including the promoter and/or any other regulatory sequences or gene (including exons and introns).

Thus, when a position is referred to as a "corresponding position" in accordance with the disclosure it is understood that nucleotides/amino acids may differ in terms of the specified numeral but may still have similar neighbouring nucleotides/amino acids. Such nucleotides/amino acids which may be exchanged, deleted or added are also included in the term "corresponding position".

Specifically, in order to determine whether an amino acid residue of the amino acid sequence of a RhlA different from a known strain corresponds to a certain position in the amino acid sequence of the known strain, a skilled artisan can use means and methods well-known in the art, e.g., alignments, either manually or by using computer programs such as BLAST2.0, which stands for Basic Local Alignment Search Tool or ClustalW or any other suitable program which is suitable to generate sequence alignments. Accordingly, a known wild-type RhlA protein may serve as "subject sequence" or "reference sequence", while the amino acid sequence of a RhlA different from said wild-type RhlA described herein can serve as "query sequence". The terms "reference sequence" and "wild type sequence" are used interchangeably herein.

In general, the term "fragment", as used herein with respect to an rhlA gene or an RhlA protein according to the disclosure, relates to shortened nucleic acid or amino acid sequences that correspond to a certain rhlA gene or RhlA protein but lack a portion thereof. For example, a fragment may be a shortened nucleic acid sequence that retains the capability of being expressed to a RhlA fragment, or an RhlA fragment can be an amino acid sequence that retains 3-hydroxyacyl-ACP O-3-hydroxyacyltransferase activity.

A host cell according to the invention may include an ortholog of the rhlA gene. An ortholog, or orthologous gene, is a gene with a sequence that has a portion with similarity to a portion of the sequence of a known gene, but found in a different species than the known gene. An ortholog and the known gene originated by vertical descent from a single gene of a common ancestor. As used herein an ortholog encodes a protein that has a portion of at least about that has at least about 30%, preferably at least about 35%, preferably at least about 40%, preferably at least about 45%, preferably at least about 50%, preferably as at least about 55%, preferably at least about 60%, preferably at least about 65%, preferably at least about 70%, preferably at least about 75% preferably at least about 80%, preferably at least about 85%, preferably at least about 90%, preferably at least about 95%, preferably at least about 98%, preferably at least about 99% sequence identity to a known protein. The respective portion of the ortholog and the respective portion of the known protein to which it is similar may be a continuous sequence or be fragmented into 1 to about 3, including 2, individual regions within the sequence of the respective protein. These 1 to about 3 regions are arranged in the same order in the amino acid sequence of the ortholog and the amino acid sequence of the known protein. Such a portion of an ortholog has an amino acid sequence that has at least about 30%, preferably at least about 35%, preferably at least about 40%, preferably at least about 45%, preferably at least about 50%, preferably as at least about 55%, preferably at least about 60%, preferably at least about 65%, preferably at least about 70%, preferably at least about 75% preferably at least about 80%, preferably at least about 85%, preferably at least about 90%, preferably at least about 95%, preferably at least about 98%, preferably at least about 99% sequence identity to the amino acid sequence of the known protein encoded by an rhlA gene.

The protein encoded by an ortholog of the rhlA gene may be identified in a database as a Rhamnosyltransferase. An ortholog of a 3-hydroxyacyl-ACP O-3-hydroxyacyltransferase encoded by an ortholog of a rhlA gene may also be identified as an alpha/beta hydrolase fold protein in a database. An ortholog of a rhamnosyltransferase encoded by an ortholog of a rhlB gene may in a database also be identified as a glycosyl transferase. An ortholog of a rhamnosyltransferase encoded by an ortholog of a rhlC gene may in a database also be be identified as a rhamnosyltransferase chain C An ortholog of the rhlA gene, the rhlB gene or the rhlC gene may also be indicated as being of unkown function in a database. Accordingly, a lack of classification as a rhamnosyltransferase in a database does not exclude a protein with a portion of similar sequence to a known rhamnosyltransferase from being an ortholog.

A heterologous rhlA gene or a heterologous ortholog of an rhlA gene may be selected from any desired species. As a few examples, an rhlA gene, or an ortholog thereof, may be from a bacterium of one of the clases Alphaproteobacteria, Betaproteobacteria, and Gammaproteobacteria. A rhlA gene, or an ortholog thereof, may for example be from a *Pseudomonas* sp., *Burkholderia* sp., *Enterobacter* sp., *Pantoea* sp., *Dickeya* sp., or *Pantoea* sp. It may for example be from a strain of *Renibacterium salmoninarum, Cellulomonas cellulans, Tetragenococcus koreensis* or *Acinetobacter calcoaceticus*. In some embodiments the rhlA gene is from one of *Burkholderia glumae, Burkholderia mallei, Burkholderia pseudomallei, Burkholderia plantarii, Burkholderia gladioli, Burkholderia ubonensis, Burkholderia ambifaria, Burkholderia cenocepacia, Burkholderia caryophylli, Dickeya zeae, Pseudomonas aeruginosa, Pseudomonas fluorescens, Pseudomonas putida, Pseudomonas oleovorans, Pseudomonas chlororaphis, Pantoea stewartii, Pseudomonas mendocina, Pseudomonas nitroreducens, Pseudomonas entomophila, Pseudomonas brassicacearum,*

Pseudomonas stutzeri, Pseudomonas fluorescens, Pseudomonas oleovorans, Pantoea ananatis, Serratia odorifera, Halothiobacillus neapolitanus, Enterobacter asburiae and Enterobacter hormaechei. Other rhlaA/RhlA sequences are disclosed in WO 2012/013554 as enzymes "E1", "E1a", "E1b", "E1c", "E1d" or "E1e".

Any rhlA gene may be included in the bacterial host cell according to the invention. Examples include, but are not limited to, a gene encoding the rhlA protein of *Pantoea ananatis*, strain LMG 20103, with SwissProt accession no. D4GK92 (Version 6 of 11 Jan. 2011), of *Pantoea ananatis* AJ13355, with SwissProt accession no. F2EY06 (Version 1 of 31 May 2011), *Pseudomonas aeruginosa*, with SwissProt accession no. Q51559 (30 Nov. 2010, version 60), of *Burkholderia thailandensis*, strain E264/ATCC 700388/DSM 13276/CIP 106301, SwissProt accession no. Q2T424 (version 25 of 30 Nov. 2010), of *Burkholderia pseudomallei*, strain 1106a, SwissProt accession no. A3P349 (version 19 of 11 Jan. 2011), of *Burkholderia pseudomallei*, strain 1710a, SwissProt accession no. C6U4Y4 (version 5 of 11 Jan. 2011), of *Burkholderia pseudomallei*, strain 1710b, SwissProt accession no. Q3JGQ8 (version 30 of 11 Jan. 2011), of *Burkholderia pseudomallei* 1106b, SwissProt accession no. C5ZMA0 (Version 4 of 11 Jan. 2011), of *Burkholderia pseudomallei*, strain 668, SwissProt accession no. A3NHI8 (version 20 of 11 Jan. 2011), *Burkholderia pseudomallei* 406e, SwissProt accession no. A8EAW6 (version 5 of 11 Jan. 2011), of *Burkholderia mallei*, SwissProt accession no. Q62CH3 (Version 32 of 11 Jan. 2011), of *Burkholderia mallei*, strain SAVP1, SwissProt accession no. A1UVS0 (version 18 of 11 Jan. 2011), of *Burkholderia mallei*, strain NCTC 10247, SwissProt accession no. A3MEC2, (version 19 of 11 Jan. 2011), of *Burkholderia mallei* JHU, SwissProt accession no. A5XJN3 (Version 7 of 11 Jan. 2011), of *Burkholderia glumae*, strain BGR1, SwissProt accession no. C5AMF7 (version 9 of 30 November 30), of *Burkholderia gladioli* BSR3, SwissProt accession no. F2LKI9 (version 1 of 31 May 2011), of *Burkholderia ambifaria*, strain MC40-6, SwissProt accession no. B1Z031 (version 13 of 30 Nov. 2010) of *Dickeya dadantii*, strain 3937, SwissProt accession no. E0SMTS (version 5 of 5 Apr. 2011), of *Pseudomonas fluorescens*, strain SBW25, SwissProt accession no. C3K3D6 (version 10 of 11 Jan. 2011), of *Pseudomonas* sp. DHT2, SwissProt accession no. A1YW88 (Version 5 of 19 Jan. 2010) and of *Pseudomonas aeruginosa*, strain PA7, SwissProt accession no. A6V1U6 (version 19 of 30 Nov. 2010), to name a few. As four examples of a respective rhlA gene may serve the gene of EMBL-Bank accession no. CP000744.1 of *Pseudomonas aeruginosa* PA7, the gene of NCBI Gene ID 4888867 of *Burkholderia pseudomallei* strain 668, the gene of NCBI GeneID 8894591 of the *Pantoea ananatis* LMG 20103 chromosome (NCBI reference sequence NC_013956.2), the gene of NCBI GeneID:9733431 of the *Dickeya dadantii* 3937 chromosome (NCBI reference sequence NC_014500.1).

Further proteins have been identified that are likely to define RhlA. A gene encoding such a protein can likewise be employed as long as it results in the formation of a functional 3-hydroxyacyl-ACP O-3-hydroxyacyltransferase subunit. Based on sequence similarity on the protein level, examples of genes encoding probable rhamnosyltransferase 1A subunits include, but are not limited to, a gene encoding the protein of *Pseudomonas putida*, strain W619, SwissProt accession no. B1J418 (version 14 of 30 Nov. 2010), the protein of *Pseudomonas mendocina*, strain ymp, SwissProt accession no. A4XS03 (version 20 of 31 May 2011), the protein of *Pseudomonas* sp. TJI-51, SwissProt accession no. F0E3C8 (version 2 of 31 May 2011), the protein of *Pseudomonas* sp. DHT2, SwissProt accession no. A1YVV88 (version 5 of 19 Jan. 2010), the protein of *Pseudomonas syringae* pv. *Phaseolicola*, strain 1448A/Race 6, SwissProt accession no. Q48HB4 (Version 29 of 11 Jan. 2011), the protein of *Pseudomonas savastanoi* pv. *savastanoi* NCPPB 3335, SwissProt accession no. D71414 (version 2 of 5 Apr. 2011), the protein of *Pseudomonas* sp. USM 4-55, SwissProt accession no. B7SJG2 (version 4 of 10 Aug. 2010), the protein of *Pseudomonas nitroreducens*, SwissProt accession no. Q93LI7 (version 18 of 5 Oct. 2010), the protein of *Pseudomonas entomophila*, strain $L^{-18}$, SwissProt accession no. Q1I5S9 (version 27 of 11 Jan. 2011), the protein of *Pseudomonas brassicacearum* subsp. *brassicacearum* NFM421, SwissProt accession no. F2KE24 (version 1 of 31 May 2011), the protein of *Pseudomonas stutzeri* (*Pseudomonas* perfectomarina), SwissProt accession no. Q8KSD5 (version 1 of 5 Oct. 2010), the protein of *Pseudomonas fluorescens*, SwissProt accession no. B1PWE2 (version 6 of 5 Oct. 2010), the protein of *Pseudomonas oleovorans*, SwissProt accession no. Q9KJH8 (version 33 of 31 May 2011), the protein of *Pseudomonas* sp. USM 4-55, SwissProt accession no. B7SJG2 (version 4 of 10 Aug. 2010), the protein of *Pseudomonas pseudoalcaligenes*, SwissProt accession no. Q93MS5 (version 25 of 5 Oct. 2010), the protein of *Burkholderia ambifaria*, strain MC40-6, SwissProt accession no. B1Z031 (version 1 of 30 Nov. 2010), the protein of *Burkholderia ambifaria*, strain ATCC BAA-244/AMMD, SwissProt accession no. Q0B714 (version 22 of 11 Jan. 2011), the protein of *Burkholderia ambifaria* MEX-5, SwissProt accession no. B1T5A9 (version 5 of 10 Aug. 2010), the protein of *Burkholderia ambifaria* IOP40-10 with SwissProt accession no. B1FHM8 (version 6 of 5 Oct. 2010), the protein of *Burkholderia* sp. TJI49, SwissProt accession no. F0GF54 (Version 2 of 31 May 2011), the protein of *Burkholderia cenocepacia*, strain AU 1054, SwissProt accession no. Q1BQD9 (Version 21 of 30 Nov. 2010), the protein of *Burkholderia cenocepacia*, strain MCO-3, SwissProt accession no. B1K7I0 (30 Nov. 2010), the protein of *Burkholderia cepacia*, strain J2315/LMG 16656, SwissProt accession no. B4EHI9 (version 13 of 11 Jan. 2011), the protein of *Burkholderia* sp. strain 383 (*Burkholderia cepacia* strain ATCC 17760/NCIB 9086/R18194 (version 26 of 30 November), the protein of *Burkholderia caryophylli*, SwissProt accession no. Q93LI6 (Oct. 5, 2010. Version 20), the protein of *Burkholderia ubonensis* Bu, NCBI accession no. ZP_02376540.1 (as of 9 Dec. 2010), the protein of *Brevundimonas* sp. BAL3, SwissProt accession no. B4WER6 (version 6 of 10 Aug. 2010), the protein of *Acidovorax ebreus*, strain TPSY, SwissProt accession no. B9MA04 (version 12 of 30 Nov. 2010), the protein of *Acidovorax* sp. strain JS42, SwissProt accession no. A1W249 (version 26 of 30 Nov. 2010), the protein of *Dickeya dadantii*, strain Ech703, SwissProt accession no. C6C8B4 (version 8 of 30 Nov. 2010), the protein of *Dickeya dadantii*, strain Ech586, SwissProt accession no. D2C1P1 (version 7 of 30 Nov. 2010), the protein of *Dickeya dadantii*, strain 3937 (*Erwinia chrysanthemi*, strain 3937), SwissProt accession no. E0SMTS (Version 5 of 5 Apr. 2011), the protein of *Dickeya zeae*, strain Ech1591, SwissProt accession no. C6CKC2 (version 8 of 30 Nov. 2010), the protein of *Serratia odorifera* DSM 4582, SwissProt accession no. D4E5A8 (version 4 of 5 Apr. 2011), the protein of *Nocardia farcinica* with SwissProt accession no. Q5YPG5 (version 35 of 30 Nov. 2010), the protein of *Anaeromyxobacter dehalogenans*, strain 2CP-C, with SwissProt accession no. Q2IK44 (version 33 of 30 Nov. 2010), the protein of *Anaeromyxobacter dehalogenans*, strain 2CP-1/ATCC BAA-258, with SwissProt accession no. B8J5U1 (version 11 of 30 Nov. 2010), the protein of *Amycolatopsis mediterranei*, strain U-32, with SwissProt accession no. D8I794 (version 4 of 11 Jan. 2011) and the protein of *Halothiobacillus neapolitanus*, strain ATCC 23641/c2 (*Thiobacillus neapolitanus*), SwissProt accession no. D0KWX9 (version 6 of 30 Nov. 2010).

Host cells which may be used in the expression systems of the present invention are not strictly limited, provided that they are suitable for use in the expression of rhlA. The host cell is preferably non-pathogenic for humans. The non-pathogenic host cell is preferably a prokaryotic host cell or a yeast host cell, preferably a bacterial host cell. Where both a homologous rhlA gene are to be placed under the control of a heterologous promoter, a bacterial host may be selected that has a respective endogenous rhlA gene. A suitable host having an endogenous rhlA gene and may for example be selected from a bacterial isolate that has been found to produce rhamnolipids, for example of *Acinetobacter calcoaceticus*, *Renibacterium salmoninarum*, *Cellulomonas cellulans*, *Nocardioides* sp., *Tetragenococcus koreensis*, *B. glumae*, *B. pseudomallei*, *B. plantarii*, *B. thailandensis*, *Myxococcus* sp., *Acinetobacter calcoaceticus*, *Enterobacter asburiae*, *Enterobacter hormaechei*, *Pantoea stewartii*, *Pseudomonas alcaligenes*, *Pseudomonas aeruginosa*, *Pseudomonas cepacia*, *Pseudomonas* sp. EP-3, *Pseudomonas chlororaphis*, *Pseudomonas clemancea*, *P. collierea*, *P. fluorescens*, *P. putida*, *P. luteola*, *P. stutzeri* or *P. teessidea* or *Serratia* sp. ATCC 39006 (Abdel-Mawgoud, et al., 2010; Williamson, N. R., et al., Environmental Microbiology (2008) 10, 5, 1202-1217).

The bacterial host cell may in some embodiments be of a phylum selected from Proteobacteria, Planctomycetes, Actinobacteria and Firmicutes. The host cell may for example be a *Pseudomonas* sp. proteobacterium of one of the classes Alphaproteobacteria, Betaproteobacteria, Gammaproteobacteria and Deltaproteobacteria. As a further example, the host cell may be an *Acidobacterium* of one of the classes Acidobacteriales and Solibacteres. The host cell may for instance be one of an *Acinetobacter* sp., *Enterobacter* sp., *Pantoea* sp., *Pseudomonas* sp, *Burkholderia* sp., *Myxococcus* sp., *Nocardioides* sp., *Pseudoxanthomonas* sp., *Methylobacterium* sp. and *Acidobacterium* sp. In some embodiments the bacterial host cell is gram-negative. The bacterial host cell may be *Pseudomonas putida*, *Pseudomonas chlororaphis*, *Pseudomonas fluorescens*, *Pseudomonas alcaligenes*, *Pseudomonas aeruginosa*, *Pseudomonas cepacia*, *Pseudomonas clemancea*, *Pseudomonas collierea*, *Pseudomonas luteola*, *Pseudomonas stutzeri*, *Pseudomonas taiwanensis*, *Pseudomonas* sp. VLB120, *Pseudomonas teessidea*, *Escherichia coli*, *Renibacterium salmoninarum*, *Cellulomonas cellulans*, *Tetragenococcus koreensis*, *Burkholderia glumae*, *Burkholderia mallei*, *Burkholderia pseudomallei*, *Burkholderia plantarii*, *Burkholderia thailandensis*, *Acinetobacter calcoaceticus*, *Enterobacter asburiae*, *Enterobacter hormaechei*, *Pantoea stewartii* and *Pantoea ananatis*.

In the state of the art, Déziel et al. as well as Choi et al. suggest the utilization of *P. aeruginosa*, a facultative human pathogen, for the production of HAA. In contrast thereto, the inventors of the present invention have recognized that with regard to biological safety and considering industrial production of HAA, non-pathogenic (at least for humans) bacterial host cells are to be preferred in the present invention.

A host cell according to the invention may preferably not comprise an rhlB gene or an ortholog thereof under control of a heterologous promoter or may preferably not comprise an rhlB gene or an ortholog thereof. Examples for rhlB genes include, but are not limited to, a gene encoding the RhlB protein of *Pseudomonas aeruginosa*, with SwissProt accession no. D2EDM4 (version 5 of 8 Mar. 2011), of *Pseudomonas aeruginosa*, strain UCBPP-PA14, with SwissProt accession no. Q02QW7 (version 27 of 8 Mar. 2011), of *Pseudomonas aeruginosa*, strain PA7, with SwissProt accession no. A6V1U7 (Version 23 of 8 Mar. 2011), of *Pseudomonas* sp. BSFD5, with SwissProt accession no. D9IV58 (Version 4 of 8 Mar. 2011), of *Pseudomonas aeruginosa* 2192 with SwissProt accession no. A3LDS3 (Version 17 of 8 Mar. 2011), of *Burkholderia mallei*, strain SAVP1, with SwissProt accession no. A1UVR8 (version 20 of 8 Mar. 2011), of *Burkholderia mallei* ATCC 10399, SwissProt accession no. A9K2TO (version 14 of 8 Mar. 2011), of *Burkholderia mallei* JHU, SwissProt accession no. A5XJN5 (version 14 of 8 Mar. 2011), of *Burkholderia mallei* PRL-20, SwissProt accession no. C5NA24 (version 5 of 8 Mar. 2011), of *Burkholderia pseudomallei*, strain 1106a, SwissProt accession no. A3P351 (Version 21 of 8 Mar. 2011), of *Burkholderia pseudomallei*, strain 1106b, SwissProt accession no. C5ZMA2 (Version 6 of 8 Mar. 2011), of *Burkholderia thailandensis*, strain E264/ATCC 700388/DSM 13276/CIP 106301, SwissProt accession no. Q2T425 (Version 32 of 8 Mar. 2011), of *Dickeya dadantii*, strain 3937 (*Erwinia chrysanthemi*, strain 3937), SwissProt accession no. E0SJM9 (Version 6 of 5 Apr. 2011), of *Pantoea ananatis* AJ13355, SwissProt accession no. F2EY05 (Version 1 of 13 May 2011), of *Pantoea ananatis*, strain LMG 20103, SwissProt accession no. D4GK91 (Version 7 of 8 Mar. 2011), of *Blastopirellula marina* DSM 3645, SwissProt accession no. A4A1V5 (Version 13 of 8 Mar. 2011) and of *Acidobacterium* sp. MPSACTX8, SwissProt accession no. D6UX52 (Version 3 of 11 Jan. 2011).

As a few examples of a respective rhlB gene may serve the *Pantoea ananatis* LMG 20103gene of EMCBI Gene ID 8894590 (as of 12 May 2011), the *Pseudomonas aeruginosa* PAO1 gene of EMCBI Gene ID 878954 (as of 10 Mar. 2011), the *Burkholderia pseudomallei* 1106a gene of EMCBI Gene ID 4905917 (as of 14 Jan. 2011), the *Burkholderia mallei*, strain SAVP1, gene of EMCBI Gene ID 4678088 (as of 12 Mar. 2010), the *Burkholderia mallei*, strain ATCC 23344, gene of EMCBI Gene ID 3086474 (as of 22 Mar. 2011), the *Burkholderia mallei*, strain ATCC 23344, gene of EMCBI Gene ID 3087541 (as of 22 Mar. 2011)

Similar to the 3-hydroxyacyl-ACP O-3-hydroxyacyltransferase protein, further proteins have been identified that are likely to define rhamnosyltransferase 1 protein. On the basis of sequence similarity on the protein level, examples of genes encoding probable rhamnosyltransferase 1 protein include, but are not limited to, a gene encoding the protein of *Burkholderia pseudomallei* with SwissProt accession no. Q63KL0 (Version 35 of 8 Mar. 2011), the protein of *Burkholderia pseudomallei* 305, SwissProt accession no. A4LRW4 (Version 13 of 11 Jan. 2011), the protein of *Burkholderia cenocepacia*, strain HI2424, SwissProt accession no. AOB2F2 (Version 24 of 8 Mar. 2011), the protein of *Burkholderia cenocepacia*, strain MCO-3, SwissProt accession no. B1K712 (Version 13 of 8 Mar. 2011), the protein of *Burkholderia cepacia*, strain J2315/LMG 16656 (*Burkholderia cenocepacia*, strain J2315), SwissProt accession no. B4EHI7 (Version 13 of 8 Mar. 2011), the protein of

*Burkholderia cenocepacia*, strain AU 1054, SwissProt accession no. Q1BQD7 (Version 31 of 8 Mar. 2011), the protein of *Burkholderia ambifaria*, strain ATCC BAA-244/ AMMD, (*Burkholderia cepacia*, strain AMMD), SwissProt accession no. Q0B716 (Version 28 of 8 Mar. 2011), the protein of *Burkholderia glumae*, strain BGR1, SwissProt accession no. C5AMF8 (Version 10 of 8 Mar. 2011), the protein of *Burkholderia gladioli* BSR3, SwissProt accession no. F2LT33 (Version 1 of 31 May 2011), the protein of *Burkholderia* sp. TJI49, SwissProt accession no. F0GF56 (Version 2 of 31 May 2011), the protein of *Burkholderia multivorans* CGD2M with SwissProt accession no. B9C4N0 (Version 6 of 8 May 2011), the protein of *Dickeya dadantii*, strain Ech586, SwissProt accession no. D2BRY4 (Version 8 of 8 Mar. 2011), the protein of *Dickeya dadantii*, strain Ech703, SwissProt accession no. C6C959 (Version 9 of 8 Mar. 2011), the protein of *Dickeya zeae*, strain Ech1591, SwissProt accession no. C6CEW6 (Version 9 of 8 Mar. 2011), the protein of *Polaromonas* sp. strain JS666/ATCC BAA-500, SwissProt accession no. Q121J6 (Version 32 of 8 Mar. 2011), the protein of *Methylobacterium extorquens*, strain PA1, SwissProt accession no. A9W4M1 (Version 19 of 8 Mar. 2011), the protein of *Methylocystis* sp. ATCC 49242, SwissProt accession no. E8KZV1 (Version 2 of 31 May 2011), the protein of *Methylobacterium chlorometh- anicum*, strain CM4/NCIMB 13688, SwissProt accession no. B7L372 (Version 12 of 8 Mar. 2011), the protein of *Acidobacterium* sp. MPSACTX8, SwissProt accession no. D6UZE1 (Version 4 of 8 Mar. 2011), the protein of *Acidobacterium capsulatum*, strain ATCC 51196/DSM 11244/ JCM 7670, SwissProt accession no. C1F8F6 (Version 11 of 8 Mar. 2011), the protein of *Solibacter usitatus*, strain Ellin6076, SwissProt accession no. Q023U1 (Version 25 of 8 Mar. 2011) and the protein of *Maritimibacter alkaliphilus* HTCC2654, SwissProt accession no. A3VBK0 (Version 15 of 8 Mar. 2011).

A host cell according to the invention may also preferably not comprise an rhlC gene or an ortholog thereof under control of a heterologous promoter or may preferably not comprise an rhlC gene or an ortholog thereof. A rhlC gene, or an ortholog thereof, may be from a bacterium of one of the classes Alphaproteobacteria, Betaproteobacteria, Gammaproteobacteria, Acidobacteriales, and Planctomycetacia. A rhlC gene, or an ortholog thereof, may for example be from one of *Pseudomonas aeruginosa, Ralstonia solanacearum, Burkholderia glumae, Burkholderia pseudomallei, Burkholderia mallei, Burkholderia thailandensis, Burkholderia gladioli, Burkholderia cenocepacia, Burkholderia ambifaria, Burkholderia phytofirmans, Burkholderia phymatum, Burkholderia multivorans, Lautropia mirabilis, Variovorax paradoxus, Methylobacterium populi, Methylobacterium chloromethanicum, Methylobacterium extorquens, Methylotenera mobilis* and *Planctomyces maxis*.

The selection of the rhlA gene, or the ortholog thereof, may affect the structure of the HAA produced by the host cell. Andrä et al. (Biol. Chem. (2006) 387, 301-310) and Hörmann et al. (Eur. J. Lipid Sci. Technol. (2010) 112, 674-680) have for example reported that *B. plantarii*, strains DSM 6535 and DSM 9509 produce a dirhamnolipid with two saturated 3-hydroxy-n-tetradecanoic acid fatty acid chains Consequently, the RhlA protein isolated from said stains will produce HAA comprising two saturated 3-hydroxy-n-tetradecanoic acid fatty acid chains. In contrast thereto, RhlA from *P. aeruginosa* produces an HAA with two saturated 3-hydroxy-n-decanoic acid fatty acid chains. An overview of the different structures of rhamnolipds that can be expected to be formed, and, consequently, which HAA will be formed by the respective RhlA, can be found in Abdel-Mawgoud et al. (2010).

If not otherwise indicated, the term "fatty acid" as used herein refers to carboxylic acids having a long, unbranched, aliphatic hydrocarbon chain which is either saturated or unsaturated. Most naturally occurring fatty acids have a chain of a number of carbon atoms, suitably from 4 to 28. Unsaturated fatty acids have one or more double bonds between carbon atoms of the hydrocarbon backbone. Fatty acids bearing more than one double bond are often referred to as polyunsaturated fatty acids. "Fatty acids" of the invention may also refer to fatty acids that are substituted with one or more hydroxy group(s), preferably not more than 3, preferably not more than 2, preferably not more than 1 hydroxy group. Such hydroxy-substituted fatty acids may also be referred to as "hydroxy fatty acids".

As RhlA often favor 3-hydroxy fatty acids with certain defined numbers of carbon atoms as substrates, the HAA produced mainly comprise 3-hydroxy fatty acid moieties with a certain number of carbon atoms, corresponding to the preferred substrate of the respective RhlA. In this context the term "mainly" means, that the 3-hydroxy fatty acid moieties comprised in the HAA produced comprise more than about 30%, preferably more than about 35%, preferably more than about 40%, preferably more than about 45%, preferably more than about 50%, preferably more than about 55%, preferably more than about 60%, preferably more than about 65%, preferably more than about 70%, preferably more than about 75%, preferably more than about 80%, preferably more than about 85%, preferably more than about 90% 3-hydroxy fatty acid moieties having the respective amount of carbon atoms. Such a respective amount is dependent on the RhlA protein and may be about 6 to about 20, preferably about 6 to about 18, preferably about 6 to about 16, preferably about 6, 8, 9, 10, 11, 12, 14, or 16. For example, RhlA from *P. aeruginosa* produces HAA mainly comprising 3-hydroxy fatty acid moieties having 10 carbon atoms, whereas RhlA from *B. plantarii*, strains DSM 6535 and DSM 9509 produce HAA mainly comprising 3-hydroxy fatty acid moieties having 14 carbon atoms.

Consequently, depending on the rhlA gene introduced to the host cell, the HAA produced by the host cell may comprise more than about 30%, preferably more than about 35%, preferably more than about 40%, preferably more than about 45%, preferably more than about 50%, preferably more than about 55%, preferably more than about 60%, preferably more than about 65%, preferably more than about 70%, preferably more than about 75%, preferably more than about 80%, preferably more than about 85%, preferably more than about 90% 3-hydroxy fatty acid moieties selected from the group consisting of 3-hydroxy-n-hexanoic acid, 3-hydroxy-n-octanoic acid, 3-hydroxy-n-nonanoic acid, 3-hydroxy-n-decanoic acid, 3-hydroxy-n-decenoic acid, 3-hydroxy-n-undecanoic acid, 3-hydroxy-n-dodecanoic acid, 3-hydroxy-n-dodecenoic acid, 3-hydroxy-n-tetradecanoic acid, 3-hydroxy-n-tetradecenoic acid, 3-hydroxy-n-hexadecanoic acid and 3-hydroxy-n-hexadecenoic acid.

The titer of 1 g $L^{-1}$ HAA achievable with the host cell of the invention may be achieved by cultivation of the host cell in any suitable cultivation method including such as shaking flask cultures as exemplary illustrated in the Examples section. Typically a carbon source is either added once at the beginning of the culture or preferably repeatedly added to the shaking flask culture. In industrial application, the host cells are typically cultured in bioreactors, such as stirred tank reactors, which may be aerated during cultivation and which may include equipment for pH and/or $pO_2$ measurement, monitoring, and/or control, and where a carbon source may be fed with a defined feeding rate. Such a cultivation may be a batch cultivation, a fed-batch cultivation, where a carbon source is constantly or continuously or intermittently fed, or in a continuous process. It is envisioned by the invention that the cultivation may be in a scale of 1 L or more, preferably 10 L or more, 100 L or more, 1000 L or more, or 10000 L or more. The skilled artisan is familiar with cultivation methods for host cells and is able to choose a suitable method for the host cells described herein. With regard to the carbon source, it is clear to the skilled artisan that carbon sources should be selected that can be metabolized by the host cell of the invention. Such a carbon source may be selected from the group consisting of saccharides, such as glucose or xylose, carbon acids, such as non-fatty acid carbon acids or their corresponding salts such as acetate or butyrate or amino acids, alcohols, such as ethanol or butanol or glycerol or mixtures thereof. It is envisioned by the invention that the host cell may also be able to metabolize fatty acids. However, for industrial application, a carbon source that can be dissolved in an aqueous medium or mix with an aqueous medium may be preferred as such a carbon source would be easier available to the host cells. It is further envisioned that the host cell may be able to secrete HAA. Thus, recovery or isolation of HAA is facilitated as it would not be necessary to disrupt the cells.

In the context of the invention, 1 g $L^{-1}$ HAA may be understood as the concentration of HAA that can be measured in the culture medium at a certain time of the cultivation. However, the meaning of 1 g $L^{-1}$ HAA may also be regarded as the amount of HAA in grams produced during the cultivation divided by the average volume of the culture. The latter understanding of 1 g $L^{-1}$ HAA is particularly relevant if HAA is removed during cultivation, such as recovered in situ or isolated in situ during cultivation. The term "average volume of the culture" as used herein refers to average volume of the culture over time during the cultivation. Typically, in batch and continuous cultivation, the volume of a culture will not change markedly. However, in fed-batch processes that are often applied in industrial scale, a feed, typically comprising a carbon source, is fed to the culture so that the culture volume may increase significantly. Also other factors known to the skilled artisan can influence the culture volume. However, the skilled artisan with her/his expertise is able calculate an average culture volume over time.

The host cell of the present invention has (or is capable of achieving) preferably a carbon yield Cmol HAA/Cmol substrate ($Cmol_{HAA}/Cmol_{substrate}$, with "C" meaning carbon) of more than 0.15, preferably more than 0.16, preferably more than 0.17, preferably more than 0.18, preferably more than 0.19, preferably more than 0.20, preferably more than 0.21, preferably more than 0.22, preferably more than 0.23, preferably more than 0.24, preferably more than 0.25, preferably more than 0.26, preferably more than 0.27, preferably more than 0.28, preferably more than 0.29, preferably more than 0.30. Substrates can be a suitable carbon source described herein with glucose being preferred. The host cell of the present invention that is capable of achieving a carbon yield of more than 0.15 Cmol HAA/Cmol substrate achieves the carbon yield, since the rhlA is expressed under the control of a heterologous promoter that confers strong (high) expression of said gene(s). It is no undue burden for the skilled person to put such a promoter into practice, since strong promoters are known or can be easily synthesized and screened for strong (high) expression. For example, it can be tested as to whether a promoter confers a stronger expression than the SynPro8 promoter as described elsewhere herein. If so, such a promoter is encompassed by the present invention.

The calculation of the carbon yield coefficient Cmol HAA/Cmol substrate is preferably done as described in Stephanopoulos, Aristidou and Nielsen in Metabolic engineering: principles and methodologies (San Diego: Acad. Press, 1998), Chapter 4 and/or Chapter 8. Other sources for the calculation and application of the carbon yield coefficient are, for example, Koch et al. (1991), J. Bacteriol 173(13):4214-4219 or Heyd et al. (2008), Anal Bioanal Chem 391:1579-1590. To ensure comparability of the results, the unit Cmol is preferably chosen, since it normalizes the HAA production rate to the amount of carbon atoms present in the carbon substrate.

It is contemplated by the invention that some host cells have the ability to metabolize HAA or fatty acids and that this ability is not desired for a strain producing HAA. Without wishing to be bound by any theory, HAA metabolization may involve cleavage of HAA to fatty acids and degradation of fatty acids by β-oxidation. In order to prevent HAA metabolization, it is envisioned by the invention that the host cell can be genetically modified in a way that its capability for β-oxidation exist only in a much lower extent than a corresponding native, wild type host cell, including being absent. The host cell may for example include a mutation in the gene of an enzyme that catalyses a reaction involved in β-oxidation, or a mutation in a regulatory sequence to which the respective gene is operably linked. The respective mutation may in some embodiments give rise to the formation of a respective enzyme that has a reduced activity when compared to a corresponding wild type enzyme. In some embodiments a capability of the host cell according to the invention for β-oxidation is reduced in comparison to a wild type cell, including entirely absent. In some embodiments the host cell according to the invention is incapable of β-oxidation. The β-oxidation pathway of the host cell may for example be curtailed, including inactive. The host cell may for example have one or more genes involved in the β-oxidation pathway, such as such as FadA (3-ketoacyl-CoA thiolase, EC 2.3.1.16), FadB (trans-enoyl-CoA hydratase, EC 4.2.1.17 or S-3-hydroxyacyl-CoA dehydrogenase, EC 1.1.1.35), FadE (acyl-CoA dehydrogenase, EC 1.3.99.-), that is/are disrupted (cf. FIG. 1). The cell may for instance have a knock-out mutation in an endogenous gene of an enzyme that catalyses a reaction involved in β-oxidation. Such a gene involved in β-oxidation may be a gene that encodes an enzyme which is directly part of the β-oxidation cycle, such as FadA (3-ketoacyl-CoA thiolase, EC 2.3.1.16), FadB (trans-enoyl-CoA hydratase, EC 4.2.1.17 or S-3-hydroxyacyl-CoA dehydrogenase, EC 1.1.1.35), FadE (acyl-CoA dehydrogenase, EC 1.3.99.-), or can be a gene that makes a fatty acid accessible to β-oxidation, for instance by activating fatty acids, such as FadD (Acyl-Coenzyme A synthetase, EC 6.2.1.3). The invention also envisions other methods known to the skilled artisan by which a reduced activity of the respective enzymes can be achieved. The modified host cell described herein may be incapable of metabolizing fatty acids.

As an example of a fadD gene, where the host cell is *Pseudomonas putida*, the respective fadD may be the gene encoding the protein of SwissProt accession no. Q88EB7 (version 70 of the entry last modified on 27 May 2015). As a further example, where the host cell is *Escherichia coli*, the respective fadD may be the gene encoding the protein of SwissProt accession no.C7AJK4 (version 13 of the entry last modified on 29 Oct. 2014). As a further example, where the host cell is *Pseudomonas aeruginosa*, the respective fadD may be the gene encoding the protein of SwissProt accession no. Q9HYU4 (version 78 of the entry last modified on 27 May 2015).

Also contemplated is that some host cells may form PHA. As PHA synthesis needs the same 3-hydroxy fatty acid precursors as HAA synthesis, it is desired that the capability of PHA formation is absent in a host cell of the invention. Hence, in some embodiments the host cell according to the invention is able to produce PHA only to a much lower extent than a corresponding native, wild type host cell. The host cell may for example include a mutation in the gene of an enzyme that catalyzes the formation of PHA, or a mutation in a regulatory sequence to which the respective gene is operably linked. Such a gene may encode a polyhydroxyalkanoic acid synthase (EC 2.3.1.-) or a acyl-coenzyme A synthetase (EC 6.2.1.1) The respective mutation may in some embodiments give rise to the formation of a respective enzyme that has a reduced activity when compared to a corresponding wild type enzyme. In some embodiments a capability of the host cell according to the invention to produce PHA is reduced in comparison to a wild type cell, including entirely absent. In some embodiments the host cell according to the invention is incapable of synthesizing PHA. The PHA biosynthetic pathway of the host cell may for example be curtailed, including inactive. The host cell may for example have one or more genes in the PHA synthesis pathway that is/are disrupted. The cell may for instance have a knock-out mutation in a respective endogenous gene. Again, the means of achieving a reduced activity of the respective enzyme is not limited to introducing a knock-out mutation to in the respective gene and the invention envisions that any suitable method known to the skilled artisan can be used to reduce the activity of the desired enzyme.

Also envisioned by the invention is that an overexpression of a gene encoding for an enoyl-CoA hydratase/isomerase, such as RhlY or RhlZ as described by Abdel-Mawgoud et al. (2014), may increase HAA titer. "Overexpression" as applied to a gene, refers to the overproduction of the mRNA transcribed from the gene or the protein product encoded by the gene, at a level that is 2.5 times higher, preferably 5 times higher, more preferably 10 times higher than the expression level detected in a control sample. Genetically engineered cells are referred to herein as "metabolically engineered" cells when the genetic engineering is directed to disruption or alteration of a metabolic pathway so as to cause a change in the metabolism of carbon. An enzyme is "overexpressed" in a metabolically engineered cell when the enzyme is expressed in the metabolically engineered cell at a level higher than the level at which it is expressed in a comparable wildtype cell. In cells that do not endogenously express a particular enzyme, any level of expression of that enzyme in the cell is deemed an "overexpression" of that enzyme for purposes of the present invention. Means for achieving overexpression include introducing the respective gene to the host cell under control of a heterologous promoter which have been discussed herein extensively for rhlA gene. The means suitable to achieve overexpression of rhlA may apply mutatis mutandis to overexpression of rhlY or rhlZ as described by Abdel-Mawgoud et al. 2014.

An rhlY or rhlZ gene may be selected from any desired species. As a few examples, an rhlY or rhlZ gene may be from a bacterium of one of the classes Alphaproteobacteria, Betaproteobacteria, and Gammaproteobacteria. A rhlY or rhlZ gene may for example be from a *Pseudomonas* sp. It may for example be from a strain of *Pseudomonas aeruginosa, Pseudomonas nitroreducens, Pseudomonas mendocina, Pseudomonas oleovorans, Pseudomonas knackmussii, Pseudomonas alcaligenes, Pseudomonas thermotolerans,*

Any rhlY or rhlZ gene may be included in the host cell according to the invention. Examples include, but are not limited to, a gene encoding the RhlY or RhlZ protein of *Pseudomonas aeruginosa* as described by Abdel-Mawgoud et al. (2014).

A host cell as described herein may be used in a method of producing one or more HAA. The host cell is cultured under conditions that allow HAA production. In a method according to the invention a host cell is cultured under conditions that allow HAA production. Suitable conditions are within the routine knowledge of the skilled artisan. The formation of HAA can further be easily analysed and/or monitored since HAA are generally being secreted by a host cell. Accordingly, standard techniques of cell culture broth analysis, including chromatographic techniques such as HPLC, can be applied in this regard. Suitable conditions for culturing the host cell typically include culturing the same in an aqueous medium that is suitable for sustaining cell viability and cell growth. Illustrative examples of a suitable cell culture medium, for example for culturing a bacterial host such as a *Pseudomonas* sp. host or a *Burkholderia* sp. host, include, but are not limited to, Luria-Bertani (LB) complex medium, Inkas-medium, phosphate-limited protease peptone-glucose-ammonium salt medium (PPGAS), Minimal medium E (MME), nitrogen-limited minimal medium or mineral salt medium. Suitable cell culture media may further include salts, vitamins, buffers, energy sources, amino acids and other substances.

The term "cultivation of cells" or "culturing of cells" or "fermenting the cells" in medium in the context of the host cells of the present invention generally refers to the seeding of the cells into a culture vessel, to the growing of the cells in medium until a sufficient cell density is established and/or to the maintenance of the cells in medium, respectively. Culturing can be done in any container suitable for culturing cells. Within the methods, a carbon source may be added to the culture. Adding carbon sources to the culture may mean that the host cell is "fed" with the carbon source. The addition of carbon source can happen once, for instance at the beginning of the cultivation, or may happen repeatedly during at least a period of time of the cultivation or continuously for at least a period of time of the cultivation. A variety of carbon source may be used such as saccharides, alcohols, carbon acids, alkanes, (see e.g. Christova, N., et al., Zeitschrift flir Naturforschung (2004) 59c, 70-74), or fatty acid such as caprylic acid (also termed octanoate) or mixtures thereof. The host cell will typically be exposed to a fermentation process. The host cell may for instance be in the logarithmic growth phase or in the stationary phase or in between both phases.

Preferred carbon sources may be selected from the group consisting of saccharides, such as glucose or xylose, carbon acids, such as non-fatty acid carbon acids or their corresponding salts such as acetate or butyrate or amino acids, alcohols, such as ethanol or butanol or glycerol or mixtures thereof. However, a carbon source that can be dissolved in an aqueous medium or mix with an aqueous medium may be preferred as such a carbon source would be easier available to the host cells. Preferred carbon sources may also be mixtures comprising preferred carbon sources described herein. Mixtures of carbon sources may also be biomass hydrolysates such as hydrolysates of plan material for example of whole corn stover (*Zea mays*), as for example reviewed by Elander et al. 2009. For obtaining biomass hydrolysate, the respective feedstock may be pretreated, e.g. by lime pretreatment (Kim and Holtzapple 2005), Ammonia recycled percolation pretreatment (Kim and Lee 2005), hot water flowthrough pretreatment (Liu and Wyman 2005), dilute sulfuric acid pretreatment (Lloyd and Wyman 2005), controlled pH hot water pretreatment (Mosier et al. 2005b), or ammonia fiber expansion pretreatment (Teymouri et al. 2005). The method of obtaining biomass hydrolysate may also comprise an enzymatic hydrolysis step using for example cellulose. The resulting biomass hydrolysate may comprise sugars such as glucose or xylose. Such biomass hydrolysates employed as a carbon source in the methods described herein have the advantage that they may be cheaper than other carbon sources.

The invention envisages that in preferred embodiments, the HAA produced by the cell may be secreted by the cell or may be extracellular. The HAA that are synthesized by the cell may pass the cell membrane(s) either by diffusion or passive transport or by active transport. The HAA, which are then outside the cell can be easily recovered or isolated in the methods of the invention. This recovery or isolation can be conducted without disrupting the cell, which may be time or energy consuming. The recovery or isolation can be conducted in a sequential step, for example after fermentation, or can be conducted parallel to fermentation, for example by in recovering or isolating HAA in situ. For example, HAA may be isolated or recovered using a method as described in WO 2013/087674. Of course, many more methods for isolating HAA from a fermentation broth are known to the person skilled in the art and are all envisioned by the present invention. Further, the method may include enriching, isolating and/or purifying the HAA(s). The term "enriched" means that the HAA(s) constitute a significantly higher fraction of the HAA present in the solution of interest than in the solution from which it was taken. Enrichment may for instance include membrane filtration, for example for clarification, buffer exchange or concentration purposes. It may also include filtration or dialysis, which may for instance be directed at the removal of molecules below a certain molecular weight or extraction using a suitable solvent.

It is further envisioned by the invention that the cells of the invention are capable of producing and thus may be used for producing HAA or a HAA composition wherein the HAA concentration is 1 g L$^{-1}$ or more, for example 1 g L$^{-1}$ or more, preferably 1.1 g L$^{-1}$ or more, preferably 1.2 g L$^{-1}$ or more, preferably 1.3 g L$^{-1}$ or more, preferably 1.4 g L$^{-1}$ or more, preferably 1.5 g L$^{-1}$ or more, preferably 1.6 g L$^{-1}$ or more, preferably 1.7 g L$^{-1}$ or more, preferably 1.8 g L$^{-1}$ or more, preferably 1.9 g L$^{-1}$ or more, preferably 2 g L$^{-1}$ or more, preferably 3 g L$^{-1}$ or more, preferably 4 g L$^{-1}$ or more, preferably 5 g L$^{-1}$ or more, preferably 6 g L$^{-1}$ or more, preferably 7 g L$^{-1}$ or more, preferably 8 g L$^{-1}$ or more, preferably 9 g L$^{-1}$ or more, preferably 10 g L$^{-1}$ or more. This can be achieved by employing the cells of the invention and cultivating the cells under suitable conditions and by providing a suitable carbon source. In some embodiments, a ratio of at least 1 gramm HAA per 1 gramm biomass (cell dry weight) (1 $g_{HAA}$ $g_{CDW}$) may be achieved. This can for example be done by employing a cell of the invention and cultivating the cell under condition where a carbon source, such as a saccharide carbon source, such as glucose, is fed during the fermentation/cultivation of the cells, either intermittently or continuously. In methods for achieving a high HAA to biomass ratio, the cells may be in their stationary stage while still producing HAA (production phase). This means that the cells do not relevantly grow or do not grow during the production phase, which means that the fed carbon may be mainly used for HAA production instead of biomass generation. It is also envisioned by the invention that cells described herein may be employed in methods, where a carbon yield of more than 0.15 $Cmol_{HAA}/Cmol_{substrate}$ is achieved.

It is also envisioned by the invention that the host cells of the invention may be used in methods, where the HAA produced mainly comprise 3-hydroxy fatty acid moieties with a certain number of carbon atoms, corresponding to the preferred substrate of the respective RhlA. In this context the term "mainly" means, that the 3-hydroxy fatty acid moieties comprised in the HAA produced comprise more than about 30%, preferably more than about 35%, preferably more than about 40%, preferably more than about 45%, preferably more than about 50%, preferably more than about 55%, preferably more than about 60%, preferably more than about 65%, preferably more than about 70%, preferably more than about 75%, preferably more than about 80%, preferably more than about 85%, preferably more than about 90% 3-hydroxy fatty acid moieties having a respectively defined amount of carbon atoms. Such a respective amount is dependent on the RhlA protein and may be about 6 to about 20, preferably about 6 to about 18, preferably about 6 to about 16, preferably about 6, 8, 9, 10, 11, 12, 14, or 16, preferably 10, or preferably 14. Consequently, depending on the rhlA gene introduced to the host cell, the HAA produced by the method may comprise more than about 30%, preferably more than about 35%, preferably more than about 40%, preferably more than about 45%, preferably more than about 50%, preferably more than about 55%, preferably more than about 60%, preferably more than about 65%, preferably more than about 70%, preferably more than about 75%, preferably more than about 80%, preferably more than about 85%, preferably more than about 90% 3-hydroxy fatty acid moieties selected from the group consisting of 3-hydroxy-n-hexanoic acid, 3-hydroxy-n-octanoic acid, 3-hydroxy-n-nonanoic acid, 3-hydroxy-n-decanoic acid, 3-hydroxy-n-decenoic acid, 3-hydroxy-n-undecanoic acid, 3-hydroxy-n-dodecanoic acid, 3-hydroxy-n-dodecenoic acid, 3-hydroxy-n-tetradecanoic acid, 3-hydroxy-n-tetradecenoic acid, 3-hydroxy-n-hexadecanoic acid and 3-hydroxy-n-hexadecenoic acid. In preferred embodiments, the more than about 30%, 35%, 40%, 45%, 50%, 55%, 60%, 65%, or 70% of the HAA produced (also referred to as the "mainly produced HAA") is an HAA with a defined combination of two hydroxyfatty acids as defined above. The two hydroxyfatty acids may be individually selected from the hydroxyfatty acids defined herein. In preferred embodiments, the mainly produced HAA comprise a 3-hydroxy fatty acid moiety which is 3-hydroxy-n-decanoic acid which is connected via an ester bond to another β-hydrocyfatty acid moiety which is 3-hydroxy-n-decanoic acid (C10-C10). In other preferred embodiments, the mainly produced HAA comprise a 3-hydroxy fatty acid moiety which is 3-hydroxy-n-tetradecanoic acid which is connected via an ester bond to another 3-hydroxyfatty acid moiety which is 3-hydroxy-n-tetradecanoic acid (C14-C14) or a 3-hydroxy fatty acid moiety which is 3-hydroxy-n-tetradecanoic acid which is connected via an ester bond to a 3-hydroxyfatty acid moiety which is 3-hydroxy-n-tetradecenoic acid (C14-C14:1). Also envisioned by the invention are HAA or HAA compositions that can be obtained by the methods described herein.

The present invention also envisions a method of producing a host cell, wherein the host cell is capable of mainly producing HAA comprising fatty acids with a predefined number of carbon atoms. For this purpose, an rhlA gene encoding for an RhlA protein that has the desired substrate- and product specificity is selected. Such a desired substrate specificity is described herein and may be for example that the HAA produced mainly by the RhlA comprise 3-hydroxy fatty acid moieties with a certain number of carbon atoms, corresponding to the preferred substrate of the respective RhlA. The method of producing the host cell further comprises introducing the selected rhlA gene or ortholog thereof into the cell under the control of a heterologous promotor. Wherein the promotor is preferably one as defined herein. The invention also contemplates the host cell obtained by this method.

Further envisioned by the present invention are methods of producing a fatty acid or a fatty acid composition comprising steps of producing HAA by the methods described herein and converting the HAA to give a fatty acid composition. Such a conversion may be for example conducted by enzymatic catalyzed de-esterification using an esterase. It can also be conducted by chemical means, for instance by acid catalyzed hydrolysis of esters or alkaline de-esterification. Similar to the HAA preparations that can be obtained by the methods described herein, the fatty acid composition may also comprise more than about 30%, preferably more than about 35%, preferably more than about 40%, preferably more than about 55%, preferably more than about 50%, preferably more than about 55%, preferably more than about 60%, preferably more than about 65%, preferably more than about 70%, preferably more than about 75%, preferably more than about 80%, preferably more than about 85%, preferably more than about 90% 3-hydroxy fatty acids having a respectively defined amount of carbon atoms. Such a respective amount is dependent on the RhlA protein and may be about 6 to about 20, preferably about 6 to about 18, preferably about 6 to about 16, preferably about 6, 8, 9, 10, 11, 12, 14, or 16, preferably 10, or preferably 14. Consequently, depending on the rhlA gene introduced to the host cell, the fatty acids produced by the method may comprise more than about 30%, preferably more than about 35%, preferably more than about 40%, preferably more than about 55%, preferably more than about 50%, preferably more than about 55%, preferably more than about 60%, preferably more than about 65%, preferably more than about 70%, preferably more than about 75%, preferably more than about 80%, preferably more than about 85%, preferably more than about 90% 3-hydroxy fatty acids selected from the group consisting of 3-hydroxy-n-hexanoic acid, 3-hydroxy-n-octanoic acid, 3-hydroxy-n-nonanoic acid, 3-hydroxy-n-decanoic acid, 3-hydroxy-n-decenoic acid, 3-hydroxy-n-undecanoic acid, 3-hydroxy-n-dodecanoic acid, 3-hydroxy-n-dodecenoic acid, 3-hydroxy-n-tetradecanoic acid, 3-hydroxy-n-tetradecenoic acid, 3-hydroxy-n-hexadecanoic acid and 3-hydroxy-n-hexadecenoic acid out of total fatty acids. In preferred embodiments, the mainly produced fatty acid is 3-hydroxy-n-decanoic acid or 3-hydroxy-n-tetradecanoic acid. It is also envisioned that the fatty acid concentration in the fatty acid composition is 1 g $L^{-1}$ or more, preferably 1.1 g $L^{-1}$ or more, preferably 1.2 g $L^{-1}$ or more, preferably 1.3 g $L^{-1}$ or more, preferably 1.4 g $L^{-1}$ or more, preferably 1.5 g $L^{-1}$ or more, preferably 1.6 g $L^{-1}$ or more, preferably 1.7 g $L^{-1}$ or more, preferably 1.8 g $L^{-1}$ or more, preferably 1.9 g $L^{-1}$ or more, preferably 2 g $L^{-1}$ or more, preferably 3 g $L^{-1}$ or more, preferably 4 g $L^{-1}$ or more, preferably 5 g $L^{-1}$ or more, preferably 6 g or more, preferably 7 g $L^{-1}$ or more, preferably 8 g $L^{-1}$ or more, preferably 9 g $L^{-1}$ or more, preferably 10 g $L^{-1}$ or more. Also envisioned by the present invention are fatty acid compositions obtained by the method described herein.

The present invention also relates to methods of producing a fatty alcohol or a fatty alcohol composition comprising steps of producing HAA by the methods described herein, converting the HAA to fatty alcohols. The term "fatty alcohols" as used herein relates to organic molecules having one or more hydroxyl groups (—OH), each bound to a saturated carbon atom. Here, the step of converting HAA to fatty alcohols may conducted directly in one step or may comprise steps of hydrolyzing the HAA to give a fatty acid composition, and reducing the fatty acids to give a fatty alcohol or fatty alcohol composition. As an illustrative example for a reduction of fatty acids to fatty alcohols, fatty acids may be reduced enzymatically using a suitable aldehyde dehydrogenase (e.g. an enzyme with the enzyme classification number EC 1.2.1.X, wherein "X" stands for a non-defined number) and further reducing the aldehyde using a suitable alcohol dehydrogenase (e.g. an enzyme with the enzyme classification number EC 1.1.1.X, wherein "X" stands for a non-defined number). Another illustrative example may be the chemical reduction of HAA or fatty acids to give fatty alcohols using tetrahydridoaluminate(III) (lithium aluminium hydride, LiAlH4). It does also not depart from the general concept of the invention, if HAA is converted to fatty alcohol following alternative routes. Similar to the fatty acid preparations that are described herein, the fatty alcohol composition obtained with the methods described herein may comprise more than about 30%, preferably more than about 35%, preferably more than about 40%, preferably more than about 45%, preferably more than about 50%, preferably more than about 55%, preferably more than about 60%, preferably more than about 65%, preferably more than about 70%, preferably more than about 75%, preferably more than about 80%, preferably more than about 85%, preferably more than about 90% fatty alcohols having a respectively defined amount of carbon atoms. Such a respective amount is dependent on the RhlA protein and may be about 6 to about 20, preferably about 6 to about 18, preferably about 6 to about 16, preferably about 6, 8, 9, 10, 11, 12, 14, or 16, preferably 10, or preferably 14. Consequently, depending on the rhlA gene introduced to the host cell, the fatty alcohols produced by the method may preferably comprise more than about 30%, preferably more than about 35%, preferably more than about 40%, preferably more than about 45%, preferably more than about 50%, preferably more than about 55%, preferably more than about 60%, preferably more than about 65%, preferably more than about 70%, preferably more than about 75%, preferably more than about 80%, preferably more than about 85%, preferably more than about 90% fatty alcohols selected from the group consisting of n-hexanol, n-heptanol n-octanol, n-nonanol, n-decanol, n-undecanol, n-dodecanol, n-tridecanol, n-tetradecanol, n-pentadecanol, n-hexadecanol out of total fatty alcohols. It is also envisioned that the fatty alcohol concentration in the fatty alcohol composition is 1 g $L^{-1}$ or more, preferably 1.1 g $L^{-1}$ or more, preferably 1.2 g $L^{-1}$ or more, preferably 1.3 g $L^{-1}$ or more, preferably 1.4 g $L^{-1}$ or more, preferably 1.5 g $L^{-1}$ or more, preferably 1.6 g $L^{-1}$ or more, preferably 1.7 g $L^{-1}$ or more, preferably 1.8 g $L^{-1}$ or more, preferably 1.9 g $L^{-1}$ or more, preferably 2 g $L^{-1}$ or more, preferably 3 g $L^{-1}$ or more, preferably 4 g $L^{-1}$ or more, preferably 5 g $L^{-1}$ or more, preferably 6 g $L^{-1}$ or more, preferably 7 g $L^{-1}$ or more, preferably 8 g $L^{-1}$ or more, preferably 9 g $L^{-1}$ or more, preferably 10 g $L^{-1}$ or more. Also envisioned by the present invention are fatty alcohol compositions obtained by the method described herein. Such a fatty acid composition has the advantage that it consists predominantly of fatty alcohols having a predefined number of carbon atoms. Such a composition may for example be used as fuels, plasticizers, surfactants, lubricants or solvents.

The present invention also relates to methods of producing a hydrocarbon or a hydrocarbon composition comprising steps of producing HAA by the methods described herein, and converting the HAA to hydrocarbons. The term "hydrocarbon" as used herein relates to molecules consisting entirely of hydrogen and carbon, preferably linear molecules, preferably non-branched molecules, preferably alkenes, alkanes or dienes, preferably having 6 to 20 carbon atoms. Here, the step of converting HAA to fatty alcohols may comprise steps of converting the HAA to give a fatty alcohol or fatty alcohol composition, and converting fatty alcohols to give an hydrocarbon or hydrocarbon composition. As an illustrative example, fatty alcohols may be dehydrated (e.g. by elimination) to give an alkene. The alkene may subsequently be hydrogenated to give an alkane. It does also not depart from the inventive concept if HAA are directly reduced to hydrocarbons. Similar to the fatty acid preparations that are described herein, the hydrocarbon composition obtained with the methods described herein may comprise more than about 30%, preferably more than about 35%, preferably more than about 40%, preferably more than about 45%, preferably more than about 50%, preferably more than about 55%, preferably more than about 60%, preferably more than about 65%, preferably more than about 70%, preferably more than about 75%, preferably more than about 80%, preferably more than about 85% or preferably more than about 90% fatty alcohols having a respectively defined amount of carbon atoms. Such a respective amount is dependent on the RhlA protein and may be about 6 to about 20, preferably about 6 to about 18, preferably about 6 to about 16, preferably about 6, 7, 8, 9, 10, 11, 12, 13, 14, 15 or 16, preferably 10, or preferably 14. Consequently, depending on the rhlA gene introduced to the host cell, the fatty alcohols produced by the method may preferably comprise more than about 30%, preferably more than about 35%, preferably more than about 40%, preferably more than about 45%, preferably more than about 50%, preferably more than about 55%, preferably more than about 60%, preferably more than about 65%, preferably more than about 70%, preferably more than about 75%, preferably more than about 80%, preferably more than about 85%, preferably more than about 90% hydrocarbons selected from the group consisting of 1-hexene, 1-heptene, 1-octene, 1-nonene, 1-decene, 1-undecene, 1-dodecene, 1-tetradecene, 1-pentadecene, 1-hexadecene, n-hexane, n-heptane, n-octane, n-nonane, n-decane, n-undecane, n-dodecane, n-tridecane, n-tetradecane, n-pentadecane, and n-hexadecan out of total hydrocarbons. It is also envisioned that the hydrocarbon concentration in the hydrocarbon composition is 1 g L$^{-1}$ or more, preferably 1.1 g L$^{-1}$ or more, preferably 1.2 g L$^{-1}$ or more, preferably 1.3 g L$^{-1}$ or more, preferably 1.4 g L$^{-1}$ or more, preferably 1.5 g L$^{-1}$ or more, preferably 1.6 g L$^{-1}$ or more, preferably 1.7 g L$^{-1}$ or more, preferably 1.8 g L$^{-1}$ or more, preferably 1.9 g L$^{-1}$ or more, preferably 2 g L$^{-1}$ or more, preferably 3 g L$^{-1}$ or more, preferably 4 g L$^{-1}$ or more, preferably 5 g L$^{-1}$ or more, preferably 6 g L$^{-1}$ or more, preferably 7 g L$^{-1}$ or more, preferably 8 g L$^{-1}$ or more, preferably 9 g L$^{-1}$ or more, preferably 10 g L$^{-1}$ or more. Also envisioned by the present invention are hydrocarbon compositions obtained by the method described herein. Such a hydrocarbon composition has the advantage that it consists predominantly of hydrocarbons having a predefined number of carbon atoms.

The present invention also relates to a recombinant nucleic acid molecule, including a vector, that includes 5' to 3', a promoter effective to initiate transcription in a host cell and the sequence of an rhlA gene. Such a nucleic acid molecule includes a transcriptional region functional in a bacterial host cell and a transcriptional termination region functional in a bacterial host cell. The above-described molecules may be isolated and/or purified nucleic acid, e.g. DNA molecules.

ITEMS OF THE INVENTION

The invention is further characterized by following items

Item 1. A host cell comprising an rhlA gene or an ortholog thereof, being under the control of a heterologous promoter; and wherein said host cell is capable of producing hydroxyalkanoyloxy alkanoic acid (HAA) and achieving an HAA concentration of more than 1 g L$^{-1}$ when cultured.

Item 2. The host cell of item 1, wherein the promoter is as strong or stronger than the promotor having the sequence as set forth in SEQ ID NO: 01 (SynPro8).

Item 3. The host cell of items 1 or 2, wherein the promoter is a non-viral promoter.

Item 4. The host cell of any of items 1-3, wherein the promoter is a prokaryotic or synthetic promoter.

Item 5. The host cell of any of items 1-4, wherein the promoter is a constitutive promoter.

Item 6. The host cell of any of items 1-5, wherein the host cell is recombinant.

Item 7. The host cell of any one of items 1-6, being a prokaryotic host cell or a yeast host cell.

Item 8. The host cell of any one of items 1-7, wherein the prokaryotic host cell is a bacterial host cell.

Item 9. The host cell of any one of items 1-8, wherein the host cell is of a phylum selected from Proteobacteria, Planctomycetes, Actinobacteria and Firmicutes.

Item 10. The host cell of any one of items 1-9, the cell being gram-negative.

Item 11. The host cell of any one of items 1-10, wherein the host cell is a) a *Pseudomonas* sp., proteobacterium of one of the classes Alphaproteobacteria, Betaproteobacteria, Gammaproteobacteria and Deltaproteobacteria; or b) an *Acidobacterium* of one of the classes Acidobacteriales and Solibacteres.

Item 12. The host cell of any one of items 1-11, wherein the host cell is one of a *Acinetobacter* sp., *Enterobacter* sp., *Pantoea* sp., *Pseudomonas* sp, *Burkholderia* sp., *Myxococcus* sp., *Nocardioides* sp., *Pseudoxanthomonas* sp., *Methylobacterium* sp. and *Acidobacterium* sp.

Item 13. The host cell of any one of items 1-12, wherein the host cell is selected from the group consisting of *Pseudomonas putida*, *Pseudomonas chlororaphis*, *Pseudomonas fluorescens*, *Pseudomonas alcaligenes*, *Pseudomonas aeruginosa*, *Pseudomonas cepacia*, *Pseudomonas clemancea*, *Pseudomonas collierea*, *Pseudomonas luteola*, *Pseudomonas stutzeri*, *Pseudomonas taiwanensis*, *Pseudomonas* sp. VLB120, *Pseudomonas teessidea*, *Escherichia coli*, *Renibacterium salmoninarum*, *Cellulomonas cellulans*, *Tetragenococcus koreensis*, *Burkholderia glumae*, *Burkholderia mallei*, *Burkholderia pseudomallei*, *Burkholderia plantarii*, *Burkholderia thailandensis*, *Acinetobacter calcoaceticus*, *Enterobacter asburiae*, *Enterobacter hormaechei*, *Pantoea stewartii* and *Pantoea ananatis*.

Item 14. The host cell of any one of items 1-13, wherein the host cell is non-pathogenic for a human subject.

Item 15. The host cell of any of items 1-14 not comprising an rhlB gene or an ortholog thereof, being under the control of a heterologous promoter.

Item 16. The host cell of any of items 1-15 not comprising an rhlB gene or an ortholog thereof.

Item 17. The host cell of any of items 1-16 not comprising an rhlC gene or an ortholog thereof, being under the control of a heterologous promoter.

Item 18. The host cell of any of items 1-17 not comprising an rhlC gene or an ortholog thereof.

Item 19. The host cell of any one of items 1-18, wherein the rhlA gene or the ortholog thereof, is heterologous to the host cell.

Item 20. The host cell of any one of items 1-19, wherein the rhlA gene, or the ortholog thereof, is from a *Pseudomonas* sp., *Burkholderia* sp., *Enterobacter* sp., *Pantoea* sp., *Dickeya* sp., *Renibacterium salmoninarum*, *Cellulomonas cellulans*, *Tetragenococcus koreensis* or *Acinetobacter calcoaceticus*.

Item 21. The host cell of any one of items 1-20, wherein the rhlA gene is from one of *Burkholderia glumae*, *Burkholderia mallei*, *Burkholderia pseudomallei*, *Burkholderia plantarii*, *Burkholderia gladioli*, *Dickeya zeae*, *Pseudomonas aeruginosa*, *Pseudomonas fluorescens*, *Pseudomonas putida*, *Pseudomonas oleovorans*, *Pseudomonas chlororaphis*, *Pantoea stewartii*, *Pantoea ananatis*, *Enterobacter asburiae* and *Enterobacter hormaechei*.

Item 22. The host cell of any one of items 1-21, wherein the HAA comprises a fatty acid having a main chain comprising about six to about 16 carbon atoms.

Item 23. The host cell of any one of items 1-22, wherein the fatty acid is one of 3-hydroxy-n-hexanoic acid, 3-hydroxy-n-octanoic acid, 3-hydroxy-n-nonanoic acid, 3-hydroxy-n-decanoic acid, 3-hydroxy-n-decenoic acid, 3-hydroxy-n-undecanoic acid, 3-hydroxy-n-dodecanoic acid, 3-hydroxy-n-dodecenoic acid, 3-hydroxy-n-tetradecanoic acid, 3-hydroxy-n-tetradecenoic acid, 3-hydroxy-n-hexadecanoic acid and 3-hydroxy-n-hexadecenoic acid.

Item 24. The host cell of any one of items 1-23, wherein said host cell is capable of achieving an HAA concentration of more than 1 g $L^{-1}$ in a shaking flask culture.

Item 25. The host cell of item 24, wherein a carbon source is added repeatedly to the shaking flask culture.

Item 26. The host cell of any of items 1-25, wherein the cell is capable of metabolizing a carbon source selected from the group consisting of saccharides, carbon acids and alcohols.

Item 27. The host cell of any of items 1-26, wherein the cell is capable of secreting HAA.

Item 28. The host cell of any of items 1-27 being capable of achieving a ratio of HAA to biomass of 1 $g_{HAA} g_{biomass}^{-1}$ or more.

Item 29. The host cell of any of items 1-28 having a knock-out mutation in one or more endogenous sequences encoding for a gene involved in β-oxidation of fatty acids.

Item 30. The host cell of item 29, wherein the gene encodes for acyl-CoA synthetase (FadD, EC 6.2.1.3).

Item 31. The host cell of any of items 1-30 having a knock-out mutation in one or more endogenous sequences encoding for a gene involved in PHA biosynthesis.

Item 32. The host cell of item 29 or 31, wherein the gene encodes for acyl-CoA synthethase (Acs1, EC 6.2.1.1).

Item 33. The host cell of any of items 1-32, wherein a gene encoding for R-specific enoyl-CoA hydratase, such as rhlY or rhlZ as described in Abdel-Mawgoud et al. 2014 is overexpressed.

Item 34. The host cell of any of items 1-33, wherein the host cell is incapable of metabolizing fatty acids.

Item 35. A method of producing an HAA, the method comprising culturing a host cell according to any one of items 1-34 under conditions allowing HAA production, wherein an HAA concentration of 1 g $L^{-1}$ or more is achieved.

Item 36. The method of item 35, wherein said host cell is fed with a carbon source.

Item 37. The method of item 36, wherein a carbon source is repeatedly added or continuously added for at least a part of the culturing period.

Item 38. The method of item 36 or 37, wherein the carbon source is not a fatty acid.

Item 39. The method of any of items 36-38, wherein the carbon source comprises a) saccharides such as glucose, or xylose; or b) non-fatty acid carbon acids or their corresponding salts such as acetate or butyrate or amino acids; or c) alcohols such as ethanol or butanol or glycerol; or d) mixtures thereof.

Item 40. The method of any one of items 36-38, wherein the carbon source comprises biomass hydrolysate.

Item 41. The method of any of items 35-40, wherein HAA is secreted by the cell.

Item 42. The method of any of items 35-41 being wherein a ratio of HAA to biomass of 1 $g_{HAA} g_{biomass}^{-1}$ or more is achieved.

Item 43. The method of any of items 35-42, wherein the cell is a bacterial cell.

Item 44. The method of any of items 35-43, wherein the cell is non-pathogenic.

Item 45. The method of any of items 35-44, wherein the host cell has a knock-out mutation in one or more endogenous sequences encoding for a gene involved in β-oxidation of fatty acids.

Item 46. The method of item 45, wherein the gene encodes for acyl-CoA synthetase (FadD, 6.2.1.3).

Item 47. The method of any of items 35-46, wherein the host cell has a knock-out mutation in one or more endogenous sequences encoding for a gene involved in PHA biosynthesis.

Item 48. The method of item 45 or 47, wherein the gene encodes for acyl-CoA synthetase (Acs1, 6.2.1.1).

Item 49. The method of any of items 35-48, wherein a gene encoding for R-specific enoyl-CoA hydratase or an ortholog thereof is overexpressed in the host cell.

Item 50. The method of any of items 35-49, wherein the host cell is incapable of metabolizing fatty acids.

Item 51. The method of any of items 35-50 comprising recovering said HAA.

Item 52. The method of item 51, wherein said HAA is recovered from culture supernatant.

Item 53. The method of any of items 35-52 comprising isolation of said HAA.

Item 54. Use of a host cell of any of items 1-34 for the production of HAA, wherein 1 g $L^{-1}$ or more HAA is produced.

Item 55. The use of item 54, wherein a) the mainly produced HAA comprises a fatty acid with a predefined number of carbon atoms; and b) the cell comprises an rhlA gene that catalyzes the formation of said HAA as a preferred product.

Item 56. The use of item 55, wherein the predefined number of carbon atoms is 6, 8, 9, 10, 11, 12, 14, or 16.

Item 57. The use of item 56, wherein the predefined number of carbon atoms is 10.

Item 58. The use of item 57, wherein the mainly produced HAA comprises a predefined fatty acid selected from the group consisting of 3-hydroxy-n-hexanoic acid, 3-hydroxy-n-octanoic acid, 3-hydroxy-n-nonanoic acid, 3-hydroxy-n-decanoic acid, 3-hydroxy-n-undecanoic acid, 3-hydroxy-n-dodecanoic acid, 3-hydroxy-n-tetradecanoic acid, and 3-hydroxy-n-hexadecanoic acid.

Item 59. The use of item 57 or 58, wherein the mainly produced HAA constitutes 30% (w/w) or more of total produced HAA.

Item 60. The use of any one of items 57-59, wherein a fatty acid with a predefined number of carbon atoms comprised in the HAA produced constitutes 30% (w/w) or more of total fatty acid comprised in the HAA produced.

Item 61. The use of item 60 wherein the predefined number of carbon atoms is 6, 8, 9, 10, 11, 12, 14, or 16.

Item 62. The use of item 61, wherein the predefined number of carbon atoms is 10.

Item 63. The use of any one of items 57-59, wherein a predefined fatty acid selected from the group consisting of 3-hydroxy-n-hexanoic acid, 3-hydroxy-n-octanoic acid, 3-hydroxy-n-nonanoic acid, 3-hydroxy-n-decanoic acid, 3-hydroxy-n-undecanoic acid, 3-hydroxy-n-dodecanoic acid, 3-hydroxy-n-tetradecanoic acid, and 3-hydroxy-n-hexadecanoic acid comprised in the HAA produced constitutes 50% (w/w) or more of total fatty acid comprised in the HAA produced.

Item 64. A method of producing a host cell according to any of items 1-34, wherein the host cell is capable of mainly producing HAA comprising a fatty acid with a predefined number of carbon atoms, the method comprising a) selecting an rhlA gene or ortholog thereof that encodes for a protein that catalyzes the formation of said HAA as a preferred product; and b) introducing said rhlA gene or ortholog thereof under the control of a heterologous promotor into the cell.

Item 65. The method of 64, not comprising introducing an rhlB gene or an ortholog thereof or an rhlC gene or an ortholog thereof into the host cell.

Item 66. A host cell obtainable by the method of item 64 or 65.

Item 67. An HAA preparation obtainable by the method of any one of items 35-53.

Item 68 The HAA preparation of item 67, wherein said preparation comprises HAA having more than 30% (w/w) fatty acids with a predefined number of carbon atoms of total fatty acids comprised in HAA, wherein the predefined number is 6, 8, 9, 10, 11, 12, 14, or 16.

Item 69. The HAA preparation of item 67, said preparation comprising HAA having more than 50% (w/w) fatty acids of one fatty acid selected from the group consisting of 3-hydroxy-n-hexanoic acid, 3-hydroxy-n-octanoic acid, 3-hydroxy-n-nonanoic acid, 3-hydroxy-n-decanoic acid, 3-hydroxy-n-undecanoic acid, 3-hydroxy-n-dodecanoic acid, 3-hydroxy-n-tetradecanoic acid, and 3-hydroxy-n-hexadecanoic acid of total fatty acids comprised in HAA.

Item 70. A method of producing a fatty acid composition comprising a) producing an HAA by the method of any one of items 35-53; and b) converting the HAA to give a fatty acid composition.

Item 71. The method of item 70, wherein the fatty acid composition comprises more than 30% fatty acids with a predefined number of carbon atoms, wherein the predefined number is 6, 8, 9, 10, 11, 12, 14, or 16.

Item 72. The method of item 70, wherein the fatty acid composition comprises more than 30% (w/w) fatty acids of one fatty acid selected from the group consisting of 3-hydroxy-n-hexanoic acid, 3-hydroxy-n-octanoic acid, 3-hydroxy-n-nonanoic acid, 3-hydroxy-n-decanoic acid, 3-hydroxy-n-undecanoic acid, 3-hydroxy-n-dodecanoic acid, 3-hydroxy-n-tetradecanoic acid, and 3-hydroxy-n-hexadecanoic acid of total fatty acids.

Item 73. A fatty acid composition obtainable by the method of any one of items 70-72.

Item 74. A method of producing a fatty alcohol composition comprising a) producing an HAA by the method of any one of items 35-53; and b) converting the HAA to give a fatty alcohol composition.

Item 75. The method of item 74 wherein step b) comprises b1) hydrolyzing the HAA to give a fatty acid composition; and b2) reducing the fatty acid composition to give a fatty alcohol composition.

Item 76. The method of item 74, wherein the fatty alcohol composition comprises more than 30% fatty alcohols (w/w) with a predefined number of carbon atoms of total fatty alcohols, wherein the predefined number is 6, 7, 8, 9, 10, 11, 12, 13, 14, 15, or 16.

Item 77. The method of item 74, wherein the fatty alcohol composition comprises more than 50% (w/w) fatty alcohols of one fatty alcohol selected from the group consisting of n-hexanol, n,-heptanol, n-octanol, n-nonanol, n-decanol, n-undecanol, n-dodecanol, n-dridecanol, n-tetradecanol, n-pentadecanol, n-hexadecanol of total fatty alcohols.

Item 78. A fatty alcohol composition obtainable by the method of any one of items 74-77.

Item 79. A method of producing a hydrocarbon composition comprising a) producing an HAA by the method of any one of items 35-53; and b) converting the HAA to give a hydrocarbon composition.

Item 80. The method of item 79, wherein step b comprises b1) hydrolyzing the HAA to give a fatty acid composition; and b2) converting the fatty acids to give a hydrocarbon composition.

Item 81. The method of item 79, wherein the hydrocarbon composition comprises more than 50% hydrocarbons (w/w) with a predefined number of carbon atoms of total alkanes, wherein the predefined number is 6, 7, 8, 9, 10, 11, 12, 14, 15, or 16.

Item 82. The method of item 79, wherein the hydrocarbon composition comprises more than 30% (w/w) alkanes of one alkane selected from the group consisting of 1-hexene, 1-heptene, 1-octene, 1-nonene, 1-decene, 1-undecene, 1-dodecene, 1-tetradecene, 1-pentadecene, 1-hexadecene, n-hexane, n-heptane, n-octane, n-nonane, n-decane, n-undecane, n-dodecan, n-tridecane, n-tetradecane, n-pentadecane and n-hexadecan of total hydrocarbons.

Item 83. A hydrocarbon composition obtainable by the method of any one of items 79-82.

EXAMPLES

Example 1: Bacterial Strains, Culture Conditions and Plasmids

The used bacteria strains *Pseudomonas putida* KT2440 (Nelson et al., Environ Microbiol (2002) 4, 799-808), *Pseudomonas taiwanensis* VLB120 (Köhler et al., J Biotechnol (2013) 168, 729-730) (formerly known as *Pseudomonas* species strain VLB120 (Panke et al., Appl Environ Microbiol (1998) 64, 2032-2043)), *Pantoea ananatis* LMG 20103 (de Maayer et al., J Bacteriol (2010) 192, 2936-2937) (purchased from BCCM/LMG Bacteria Collection), *Escherichia coli* DH5α (Hanahan, 1983), and *E. coli* C43(DE3) (Miroux & Walker, J Mol Biol (1996) 260, 289-298; Wagner et al., Proc Natl Acad Sci USA (2008) 105, 14371-14376) were routinely cultivated in LB-media (10 g/L tryptone, 5 g/L yeast extract, 10 g/L NaCl) at 37° C. for *E. coli* and 30° C. for *Pseudomonas* and *Pantoea* respectively. Cells containing the derivatives of vectors pSEVA241 (Silva-Rocha et al., Nucleic Acids Res (2013) 41, D666-D675) and pVLT31 (de Lorenzo et al., Gene (1993) 123, 17-24) were selected by adding kanamycin with a concentration of 50 µg/ml for recombinant *E. coli* and *Pseudomonas* and 20 µg/ml of tetracycline respectively. Transformants with derivatives of the vectors pVLT33 (de Lorenzo et al., Gene (1993) 123, 17-24) and pET28a (Novagen, Merck KGaA, Darmstadt, Germany) were selected using 50 µg/ml kanamycin.

Example 2: Construction of Expression Plasmids

Figure 9:
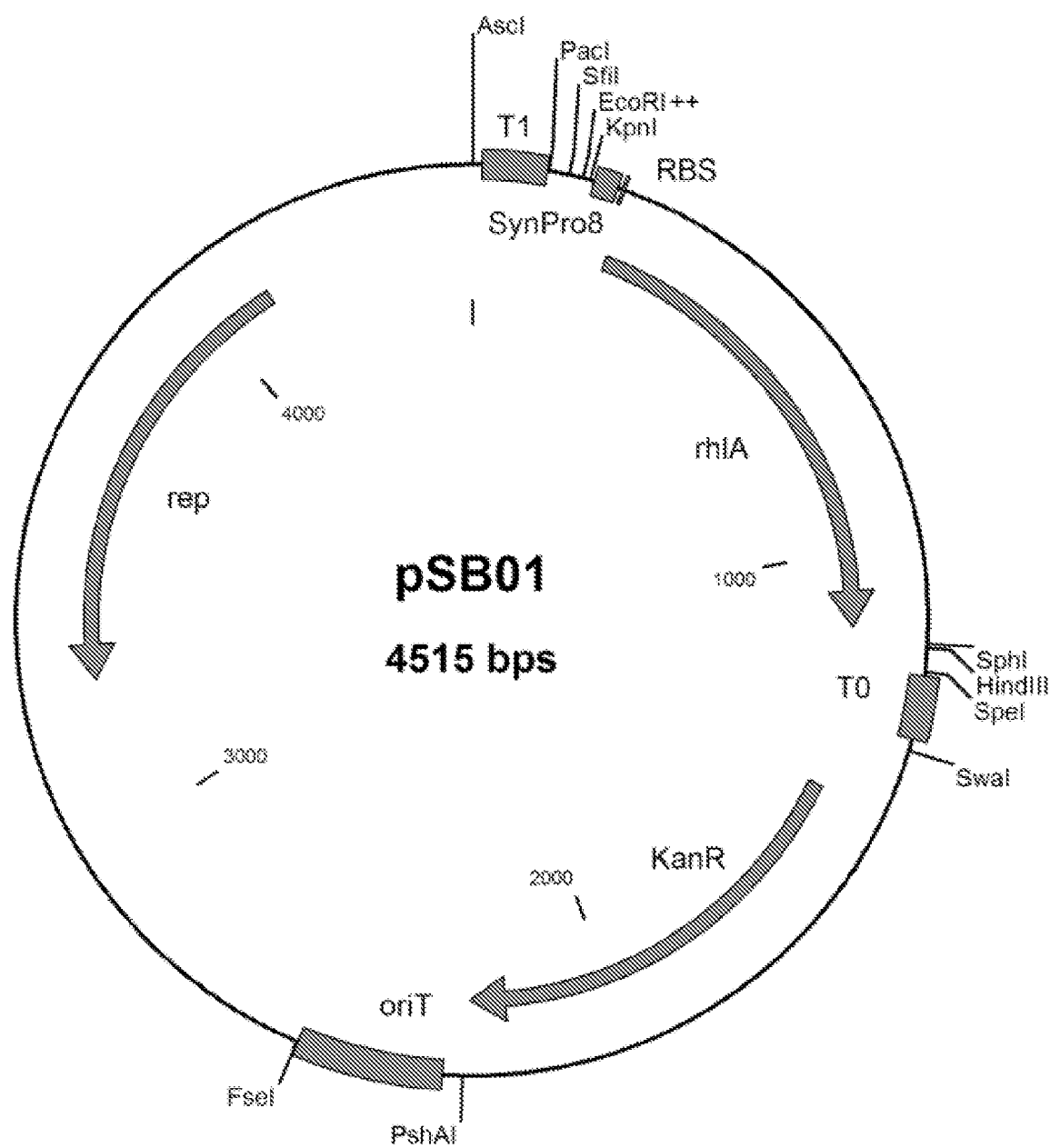
FIG. 9: HAA production vector pSB01. Plasmid pSB01, carrying the rhlA gene from *P. aeruginosa* PAO1 for HAA production. Only important restriction sites are shown. This vector contains a kanamycin resistance gene (kanR) a replication domain (rep) and an ori of replication (oriT). Upstream of the rhlA gene is a constitutive promoter (SynPro8) and a ribosomal binding site (RBS).

Vector pSB01 (FIG. 9) was constructed for HAA production. It was created using pSEVA241 as backbone carrying the kanamycin resistance gene and pRO1600/ColE1 ori. Using PCR with primers P01 and P02 rhlA originating from *P. aeruginosa* PA01 was amplified from a prior created plasmid (for rhamnolipid synthesis) and put under the control of a synthetic promoter called SynPro8. An engineered ribosomal binding site (AGGGGG) (Rühl, Laboratory of Chemical Biotechnology (2012) PhD) was also included in the sequence. Using Kpnl and Sphl the vector as well as the PCR product were cut and the linear fragments were ligated. The ligated vector was then transformed into *E. coli* DH5α. For HAA production the vector was subsequently transformed into *P. putida* KT2440 and *P. taiwanensis* VLB120.

Figure 10:
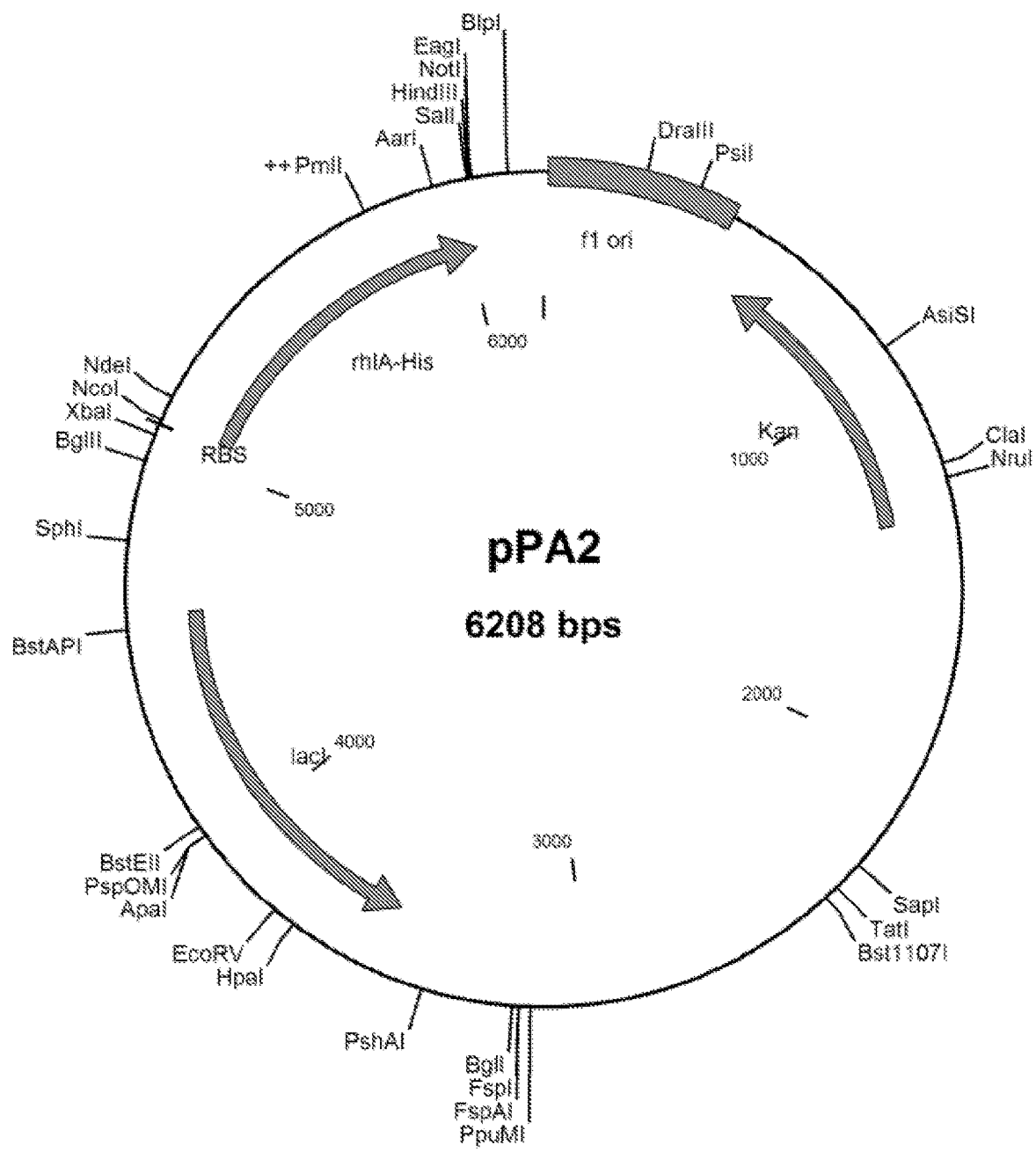
FIG. 10: Plasmid map of pPA2. Plasmid pPA2 carries the rhlA gene from *P. aeruginosa* PAO1 for expression of His-tagged RhlA and HAA production. The expression is dependent on IPTG induction of the T7 promoter located upstream of rhlA. The vector carries furthermore a lacI gene, a kanamycin resistance (kan) a pBBR322 origin and an f1 origin.

The rhlA gene from *P. aeruginosa* PAO1 was amplified from a previous constructed rhamnolipid production plasmid with Primers (Eurofins MWG Operon, Ebersberg, Germany) P03 and P04. The PCR product was digested with NdeI/SalI and ligated into pET28a digested with the same restriction endonucleases, resulting in plasmid pPA2 (FIG. 10). Plasmids pANA2-1 containing the rhlA gene from *Pantoea ananatis* LMG20103 and pBUG2 containing rhlA from *B. glumae* PG1 were created using primers P05 and P06 for pANA2-1 and P07 and P08 for pBUG2, respectively. For the amplification of rhlA of *B. glumae* PG1 pVLT33 BuG-rhlA was kindly provided by Andreas Wittgens (Wittgens, (2013) PhD). Purified PCR products and NdeI/BamHI digested pET28a were used for subsequent Gibson assay with the Gibson Assembly cloning Kit (NEB, Ipswich, Mass., USA) following the suppliers instructions.

TABLE 1

Used primers.

| Name | Sequence | Direction | Product |
|------|----------|-----------|---------|
| P01 | ATCCAGGGTACCAGCTCTTG (SEQ ID NO: 09) | fwd | pSB01 |
| P02 | CTGCATGCCTAGGCTTGTCAAGGAAA GG (SEQ ID NO: 10) | rev | pSB01 |
| P03 | CTTTAAGAAGGAGATATACATATGCG GCGCGAAAGTCTG (SEQ ID NO: 11) | fwd | pPA2 |
| P04 | GACGAGTCGACCGCAGGTCAAGGGTT CAG (SEQ ID NO: 12) | rev | pPA2 |

TABLE 1-continued

Used primers.

| Name | Sequence | Direction | Product |
|------|----------|-----------|---------|
| P05 | GCCGCGCGGCAGCCATATGATATACA TTAAAAAAATTTACTTTTCG (SEQ ID NO: 13) | fwd | pANA2-1 |
| P06 | CGGAGCTCGAATTCGGATCCTCAGAC ACCAATCTGGTTAAAAATG (SEQ ID NO: 14) | rev | pANA2-1 |
| P07 | GCCGCGCGGCAGCCATATGCCTATCG AGAAACAGG (SEQ ID NO: 15) | fwd | pBUG2 |
| P08 | CGGAGCTCGAATTCGGATCCTAGGAC AGCAGCGGCAT (SEQ ID NO: 16) | rev | pBUG2 |

Example 3: Production of HAAs

For HAA production with recombinant pseudomonads, LB-medium complemented with 10 g/L glucose and the respective antibiotic (50 µg/mL kanamycin) was used. The bacteria were cultivated in 500 mL shaking flasks without baffles, filled with growth medium to 10% of their nominal volume. The experiments were executed in a Multitron shaker (Infors AG, Bottmingen, Switzerland). Cultivation conditions were a temperature of 30° C., a shaking frequency of 250 rpm with a shaking diameter of 25 mm, and a humidity of 80%.

For the fed-batch experiment 2000 mL Fernbach flasks were used. The shaking conditions were changed to 50 mm throw at 200 rpm. The flasks were filled with 500 mL culture.

For HAA production with *E. coli*, plasmids pPA2, pANA2-1, and pBUG were transformed into *E. coli* C43 (DE3). For HAA production, a 100 mL shaking flask with 10 mL of LB containing 50 µg/mL kanamycin (for plasmid maintenance) was inoculated from a glycerol stock and grown over night at 37° C. 50 mL of the same medium in a 500 mL culture flask without baffles were inoculated with cells at $OD_{600}$ 0.1 and grown at 37° C. with orbital shaking at 200 rpm until $OD_{600}$ was between 0.5 and 0.8. Only then expression of rhlA was induced by addition of 0.5 mM IPTG and temperature was lowered to 30° C. 2 hours after induction, the cultures were supplied with 2 g/L glucose for the first time. Depending on HAA production further glucose pulses were performed. This approach was chosen to undergo an inhibition of the pET expression system to the timepoint the cells were induced by IPTG and to offer enough carbon for product formation.

Example 4: Analytics

The HAA concentration was characterized by reversed phase high performance liquid chromatography (RP-HPLC). As main column the model NUCLEODUR C18 Gravity (Macherey—Nagel GmbH & Co. KG, Diken, Germany) was used (dimensions: 150×4.6 mm; particle size: 3 µm). The HPLC system Ultimate 3000 (Dionex Corporation, Sunnyvale, USA) was connected to the Corona-charged aerosol detection (CAD) detector (Dionex Corporation, Sunnyvale, USA). The flow rate was set to 1 mL/min and the column oven temperature was set at 40° C. 5 µl of the sample were injected. Acetonitrile and millipore water supplied with 0.2% (v/v) formic acid were used as eluent. The acetonitrile concentration was linearly increased from 70% to 100% between 1 min and 9 min and it was linearly decreased from 100% to 70% between min 11 and min 12. One measurement was terminated after 15 min. The rhamnolipid concentration of *P. putida* cultures was measured after 3 days of cultivation. 1 mL of the suspension was centrifuged for 5 min at 13.400 rpm. 500 µL of the supernatant were subsequently mixed with 500 µL of acetonitrile and centrifuged for 5 min at 13.400 rpm. To measure the samples, 150 µL of the supernatant was filtered and pipetted into HPLC—vials and measured.

Example 5: Carbon Source Analytics

For substrate quantification (glucose, glycerol, acetate, ethanol, and xylose) an ion exchange chromatography was applied. We used the System Gold HPLC system composed of the pump LC-126, the autosampler LC-508, the UV detector LC-166, (all Beckmann Coulter, Krefeld, Germany), the Jetstream 2 Plus column oven (Knauer, Berlin, Germany), and the refractive index detector LCD 201 (Gynkotek, Munich, Germany). The applied column was the Organic Acid Resin (Chromatographie Service GmbH, Langerwehe, Germany) with a length of 30 cm and a diameter of 8 mm. The running buffer was 5 mM sulfuric acid, which was pumped isocratically with a flow rate of 0.8 mL/min at a temperature of 50° C. 5 µL of the sample were injected.

Example 6: Efficient Whole-Cell Biocatalysis of HAAs

Figure 7:
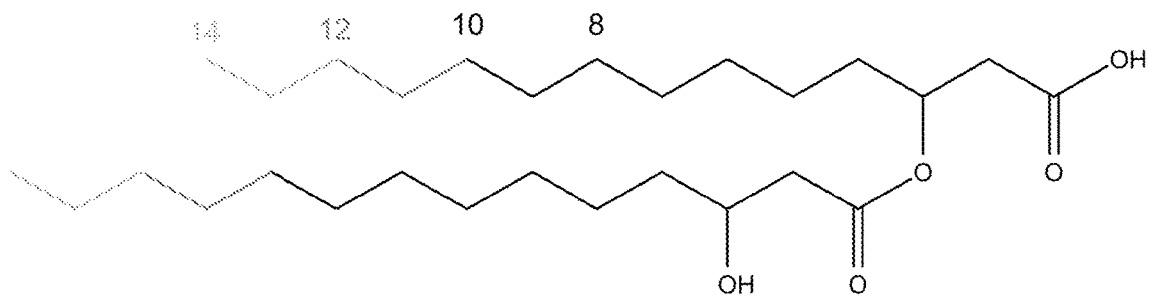
FIG. 7 illustratively depicts the structure of HAAs. The exemplary structure illustratively indicates that the carbon chains of the fatty acid moieties may have a length of 8, 10, 12, or 14 carbon atoms.

The HAA producing strain was created by only introducing the first enzyme in rhamnolipid synthesis, RhlA to the host cells. RhlA fuses two activated hydroxy-fatty acids to yield an HAA molecule (FIG. 7). The difference between HAAs and rhamnolipids is that HAAs does not contain a rhamnose unit and thus is not a rhamnolipid. Due to its carboxyl groups, it nevertheless also features an amphiphilic structure, which renders the HAA a surfactant too.

Figure 2:
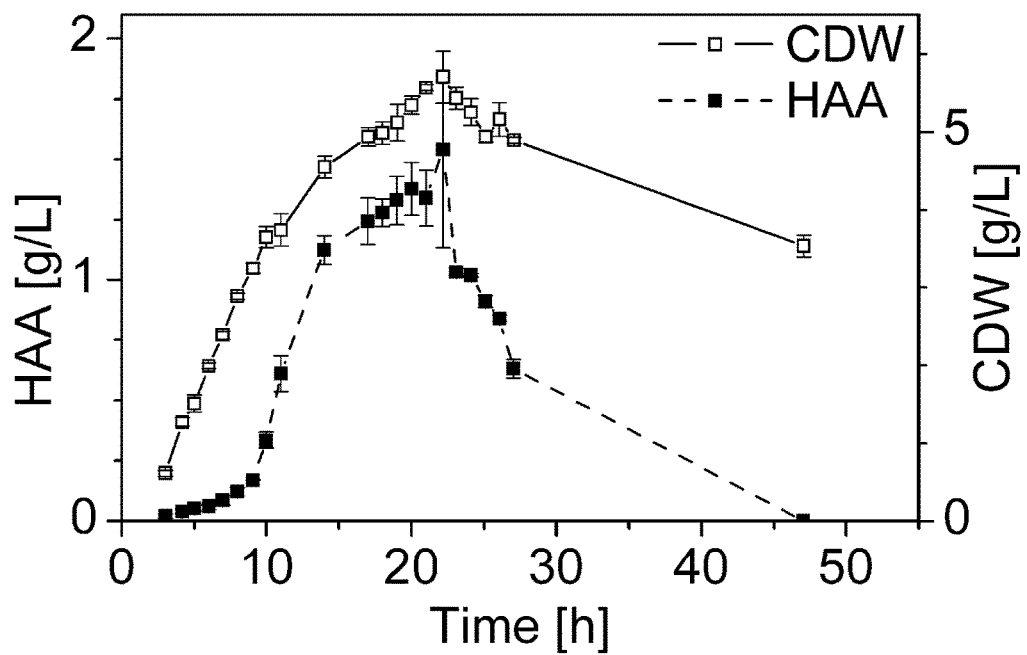
FIG. 2: HAA production with recombinant *P. putida* KT2440 pSB01. The courses of glucose degradation and HAA generation are shown over the fermentation time. The time course of cell dry weight (CDW) and HAA concentrations in an HAA production experiment carried out with *P. putida* KT2440 pSB01 are shown. Black filled squares: HAA titer [g/L], empty squares: CDW [g/L]. The error bars represent the mean deviation with a total number of two replicates. This experiment is described in Example 6.

For HAA production, the vector pSB01 was transformed into *P. putida* KT2440 and *P. taiwanensis* VLB120. After 22 hours of cultivating *P. putida* KT2440, an HAA titer of 1.5 g/L was reached with a cell density of around 6 g/L. This results in a carbon yield of 0.27 $Cmol_{HAA}/Cmol_{Glc}$ which is 41% of the theoretical yield. Unfortunately and opposing to rhamnolipids, HAAs are taken up by the cell after the carbon source has been depleted (FIG. 2) (glucose data not shown). In the native producers, HAAs only serve as precursors for rhamnolipid synthesis. For that reason it makes sense that uptake mechanisms for HAAs exist. After another 25 hours at the latest, the HAA concentration has dropped to zero.

Figure 5:
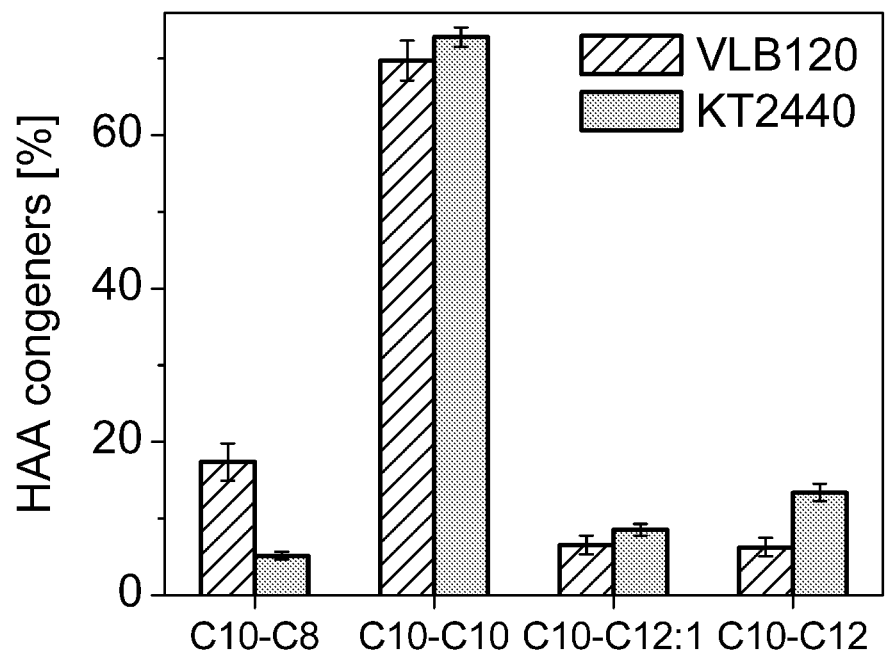
FIG. 5: The ratio of the four HAA congeners produced by *P. putida* KT2440 and *P. taiwanensis* VLB120 transformed with vector pSB01 measured in Example 6. The portions of HAA congeners synthesized by *P. taiwanensis* VLB120 pSB01 (hatched bars) and *P. putida* KT2440 pSB01 (grey bars) are shown. The error bars represent the mean deviation and are based on the values of ten time points from two biological replicates. Both strains recombinantly expressed the same RhlA protein from *P. aeruginosa* PAO1. As can be seen from the Figure, the congeners profile mostly depends on the expressed RhlA enzyme rather than on the host cell.
Figure 6:
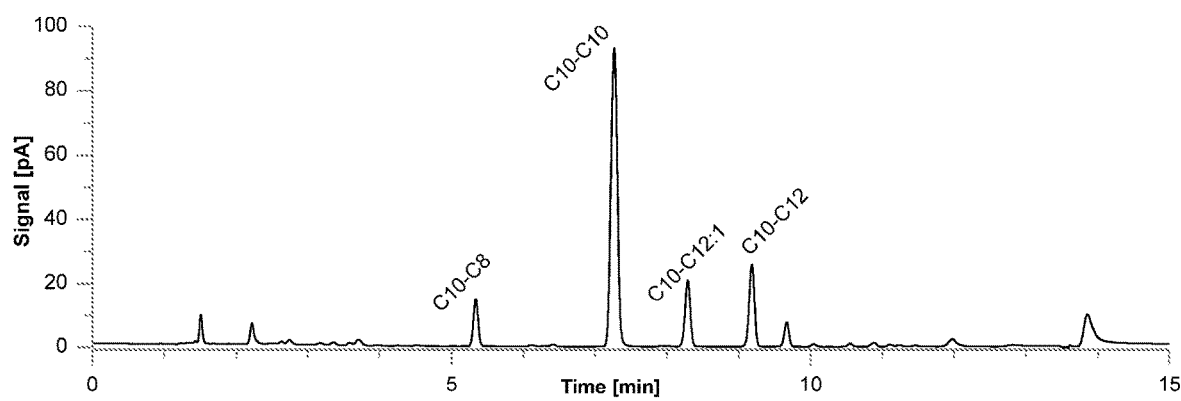
FIG. 6 illustratively depicts a chromatogram of a HPLC measurement of a sample containing the four congeners shown in FIG. 5.

The distribution of the four HAA congeners produced by *P. putida* is similar to the ratios seen in recombinant rhamnolipid synthesis. 73% of the total HAAs consist of the C10-C10 congener. This is an HAA molecule with two hydroxy-fatty acids with each ten carbon atoms. While 9% are composed of the $C_{10}$-$C_{12:1}$ congener the third biggest fraction is the $C_{10}$-$C_{12}$ congener (13%). The smallest fraction with only 5% is the congener $C_{10}$-$C_8$ (FIG. 5).

*P. taiwanensis* VLB120 pSB01, a different member of the same genus transformed with the same vector, showed a slightly increased HAA level (1.8 g/L). The HAA mixture produced by *P. taiwanensis* VLB120 pSB01 deviates slightly from the above described mixture. The main congener with two $C_{10}$ hydroxy-fatty acids is still the main compound with 70%. Nevertheless, the distribution of the other three congeners slightly differs from the known pattern. While the two congeners containing a C12 chain still feature similar ratios, with 7 and 6% respectively, the share of the $C_{10}$-$C_8$ is significantly higher (17%). In total, when regarding the total distribution, the HAA distributions of *P. putida* KT2440 pSB01 and *P. taiwanensis* VLB120 pSB01 are very similar due to the same RhlA (FIG. 5).

Example 7: Carbon Source

In a first assessment of different carbon sources for rhamnolipid production, an HAA producing *P. taiwanensis* VLB120 was cultivated in Delft minimal medium complemented either with glucose (10 g/L), glycerol (10 g/L), acetate (6 g/L), ethanol (7 g/L), or xylose (12 g/L).

Figure 4:
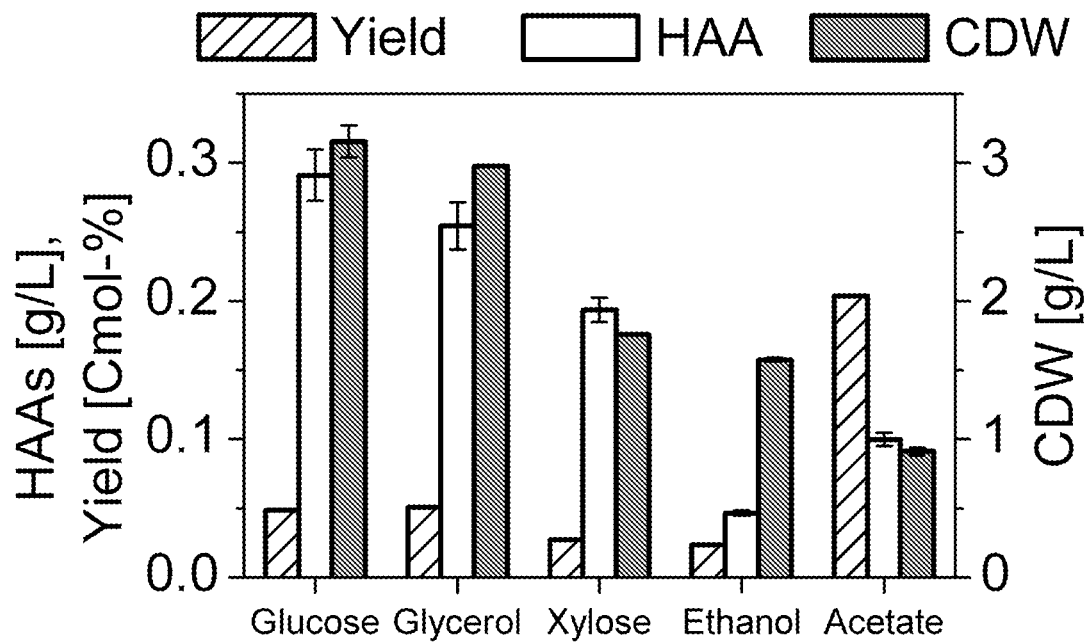
FIG. 4: HAA concentrations, carbon yields and CDW concentrations in HAA production experiments using different carbon sources carried out with *P. taiwanensis* VLB120 pSB01. Hatched bars: carbon yield [Cmol$_{HAA}$/Cmol$_{Subs}$], empty bars: maximum HAA titer [g/L], grey bars: CDW [g/L]. These experiments are described in Example 7.

*P. taiwanensis* VLB120 is capable of growing on all applied carbon sources (FIG. 4) and can produce HAAs. The best substrate for both growth and HAA production is glucose. Unfortunately, if glucose is the sole carbon source, the yield significantly drops, compared to cultivations with LB medium supplemented with glucose. Here it is beneath 0.05 $Cmol_{HAA}/Cmol_{Glc}$, while in the other cultivation it lies above 0.4 $Cmol_{HAA}/Cmol_{Glc}$. Glycerol shows similar results. Also, growth on xylose is possible for *P. taiwanensis* VLB120. However, HAA productivity and growth on xylose are significantly decreased. Growth on $C_2$-substrates is also possible but even slower. Associated therewith are probably the low HAA titers. Ethanol facilitates by far the lowest HAA concentration. Interestingly, the carbon yield is not significantly decreased. Acetate on the other hand features a very high carbon yield. With 0.2 $Cmol_{HAA}/Cmol_{Ace}$ it is ten times higher as the ethanol carbon yield.

Example 8: Fed-Batch

To further intensify the fermentation, a fed-batch approach was carried out. *P. taiwanensis* VLB120 was transformed with pSB01 for HAA production and cultivated in LB medium supplemented with 10 g/L glucose. Contrary to rhamnolipids, HAAs can be degraded by *Pseudomonas*, which provokes a big challenge in HAA production as the time point of harvesting is crucial. For that reason in previous experiments it was determined, that glucose should be fed when the glucose concentration drops beneath 1 g/L to impede HAA degradation.

Figure 3:
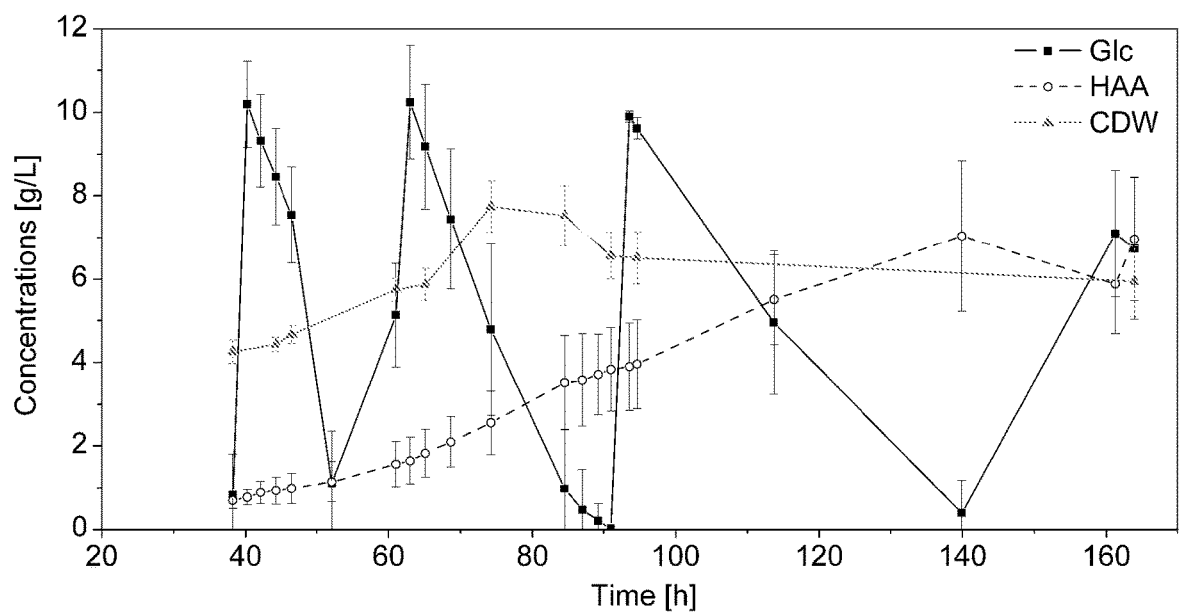
FIG. 3: Time course of cell dry weight (CDW), glucose and HAA concentrations in an HAA production experiment carried out with *P. taiwanensis* VLB120 pSB01 in a fed-batch mode. Black squares: glucose concentration [g/L], empty circles: HAA titer [g/L], grey triangles: CDW [g/L]. This experiment is described in Example 8.

The experiment was performed for almost a week and 10 g/L of glucose was fed four times. HAA titers increased steadily during the whole experiment (FIG. 3), while optical density increased slowly after the exponential growth phase. This increase could be due to PHA formation instead of growth. Consistently, the glucose uptake rate decreased after the cells ceased to grow. The results indicate that non-growing cells are able to sustain HAA production. Notably, an HAA titer of 7 g/L was reached.

The important parameters of recombinant HAA production using our constructed recombinant strains can be seen in Table 1. For all engineered strains, independent from the fermentation mode, the carbon yield ranges around 0.3 $Cmol_{HAA}/Cmol_{Glc}$. This corresponds to almost 50% of the theoretical maximal possible yield. This is an important value, as it influences the substrate usage and thus the direct production costs. This is especially valid, as in the fed batch experiment the carbon yield does not decrease. The glucose is thus converted into the product of choice with the same efficiency disregarding the state of the cell. The next step would thus be reduction of growth, to channel even more of the substrate in the direction of the HAAs.

TABLE 1

Fermentation characteristics of the three engineered recombinant surfactant producers.

| Organism | Glucose [g/L] | Cell Dry Weight [$g_{CDW}$/L] | Maximal Titer [$g_{HAA}$/L] | Yield [$g_{HAA}$/ $g_{substrate}$] | Carbon Yield[1] [$Cmol_{HAA}$/ $Cmol_{substrate}$] | Process Time [h] | Specific HAA-Production Rate[2] [g/($g_{CDW}$ h)] |
|---|---|---|---|---|---|---|---|
| P. taiwanensis VLB120 pSB01 | 10 | 5 | 1.80 | 0.18 | 0.32 (48%) | 22 | 0.016 |
| P. taiwanensis VLB120 pSB01 | 40 | 8 | 7.00 | 0.18 | 0.31 (46%) | 140 | 0.006 |
| P. putida KT2440 pSB01 | 10 | 5.7 | 1.54 | 0.15 | 0.27 (41%) | 22 | 0.012 |

[1] For the calculation of yields during production on complex media, HAAs were assumed to be synthesized from the used carbon source, while media compounds were utilized for cell growth. The numbers in parenthesis show the percentage of the maximal possible theoretical yield reached.
[2] The specific HAA production rate was calculated as average over the whole fermentation time.

Example 9: Production of Different HAA Species

Figure 11:
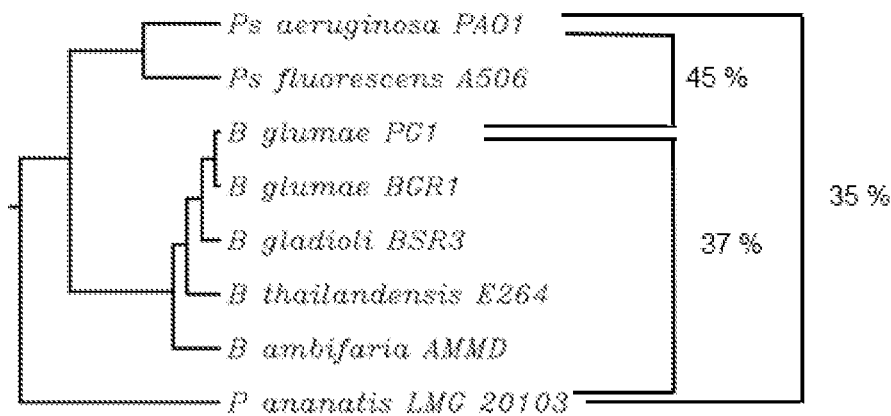
FIG. 11: Phyllogenetic tree based on amino acid sequences of RhlA. RhlA of *P. ananatis* shows 35%, that of *B. glumae* 45% identical positions compared to the protein of *P. aeruginosa*. RhlA of *B. glumae* PG1 and *P. ananatis* share 37% identical positions.

In this study the rhlA genes from three different species have been cloned and expressed recombinantly to pursue two goals. In the first place it was our intention to produce HAAs in high titers. Secondly to expand the spectrum of available HAAs with different chain lengths or other compositions of that from *P. aeruginosa* we produced and investigated HAA formation with recombinant rhlA from *P. ananatis* LMG20103 and *B. glumae* PG1. *P. ananatis* was chosen as its RhlA is most distantly related to that of *P. aeruginosa* when compared to all so far known RhlA sequences (35% identical positions, FIG. 11). Sequencing rhlA from *P. ananatis* LMG20103 showed that the published sequence contains mistakes. For comparisons to other RhlAs the correct sequence determined by our group was used. *B. glumae* as a representative of the *Burkholderia* group is supposed to produce rhamnolipids with C14-C14 chain lengths in the HAA residue (45% identical positions).

(A) $C_{10}$-HAA formation in *E. coli* C43 (DE3) pPA2

Figure 12A:
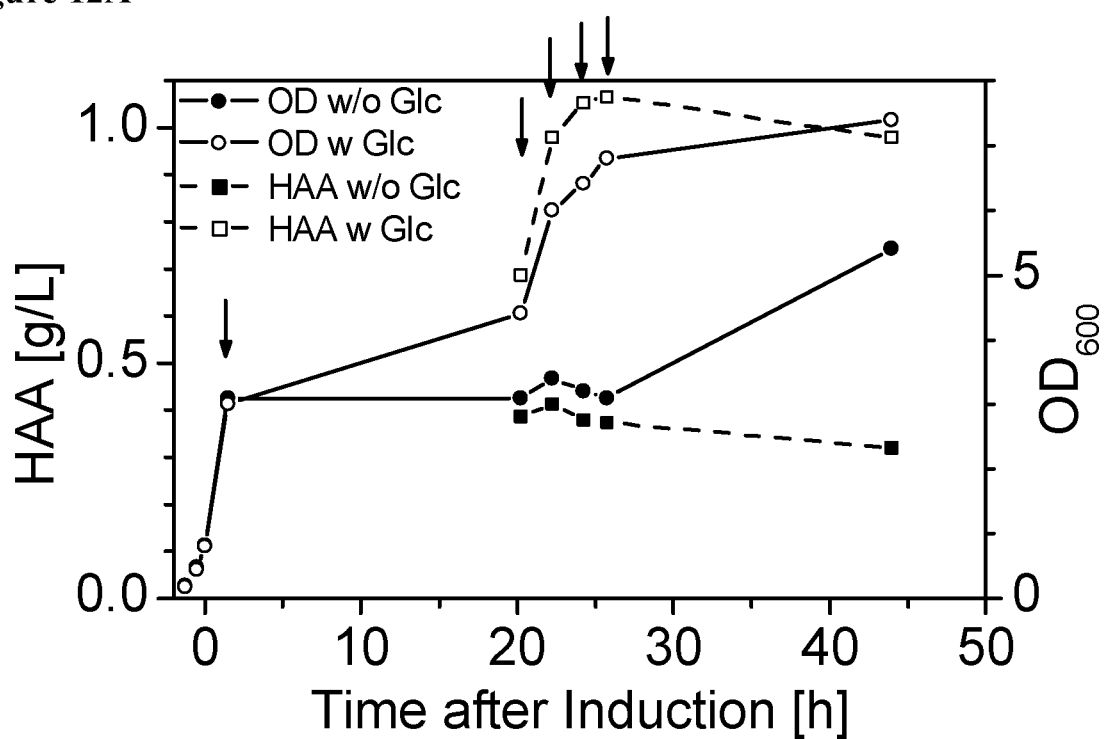
FIG. 12: (A) HAA formation with *E. coli* C43(DE3) pPA2. Arrows indicate glucose pulses. Filled symbols represent a culture co-fed without glucose, empty symbols show growth and HAA formation with glucose pulses. Co-feeding results in HAA titers of more than 1 g/l. (B) HAA formation with plasmid pANA2-1. Arrows indicate glucose pulses. The dotted line and major squares show HAA formation, minor symbols and the solid line show bacterial growth. (C) HAA formation with *E. coli* C43 pBUG2. Arrows indicate glucose pulses. The dotted line and major squares show HAA formation, minor symbols and the solid line show bacterial growth.
Figure 16A:
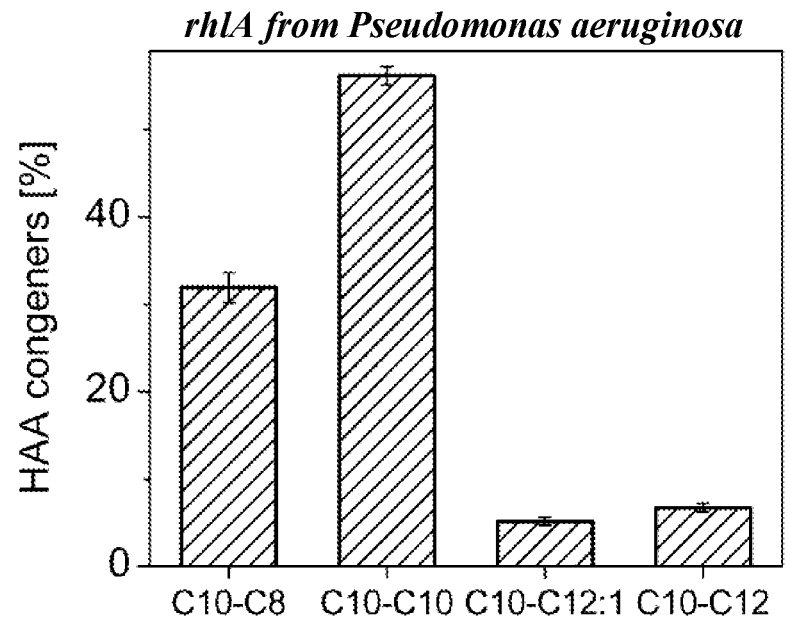
FIG. 16A: *E. coli* transformed with rhlA from *P. aeruginosa* PAO1.

As *E. coli* was chosen as expression host for the RhlAs with different specificities at first an experiment with the *P. aeruginosa* rhlA was carried out to assess the general suitability of the host organism. *E. coli* C43(DE3) was transformed with pPA2. Subsequently, growing cultures of *E. coli* C43(DE3) pPA2 were supplemented with 2 g/l glucose 2 hours after IPTG induction. Repeated feeding resulted in raised HAA titers of more than 1 g/l within 26 hours after induction and increased cell densities. When the strain was not co-fed with glucose, only about 400 mg/l HAAs could be detected (FIG. 12A). The distribution of HAA congeners is shown in FIG. 16A.

Further experiments showed that only 2 glucose pulses (2 and 20 hours after induction) are sufficient for increased HAA titers (data not shown).

(B) HAA Formation with RhlA from *Pantoea ananatis*

Figure 12B:
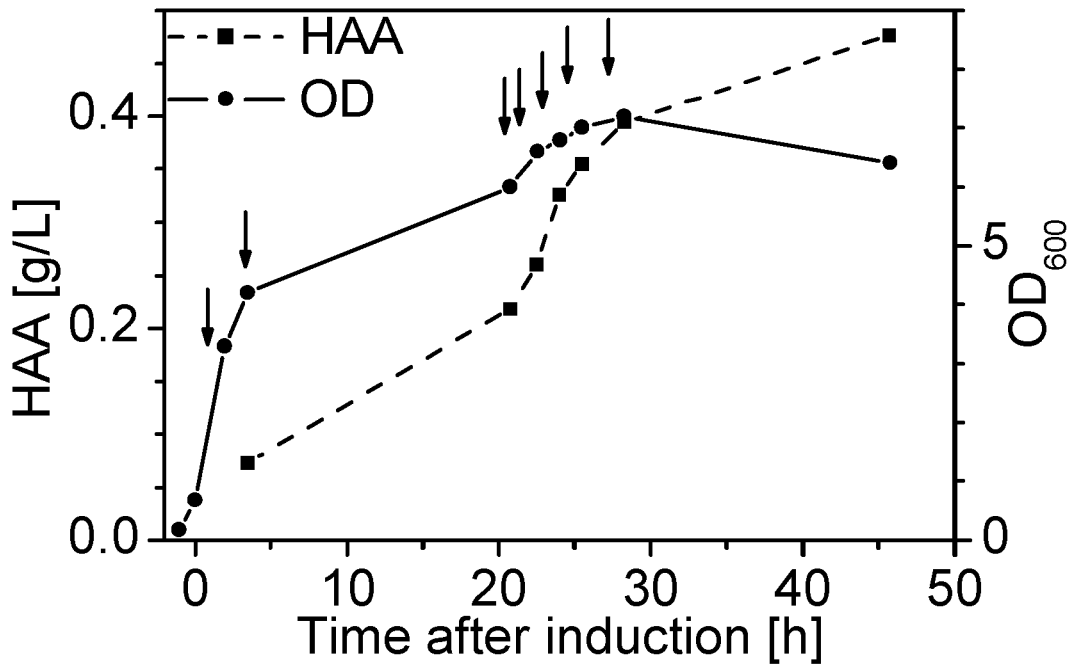

According to the data acquired with pPA2 also with *E. coli* C43 (DE3) pANA2-1 HAA titers could be raised by the addition of defined glucose pulses. This expression system also caused the strain to produce HAAs consisting mainly of the C10-C10 and C10-C8 congeners (FIG. 12B).

(C) HAA Formation with RhlA from *Burkholderia glumae*

Figure 12C:
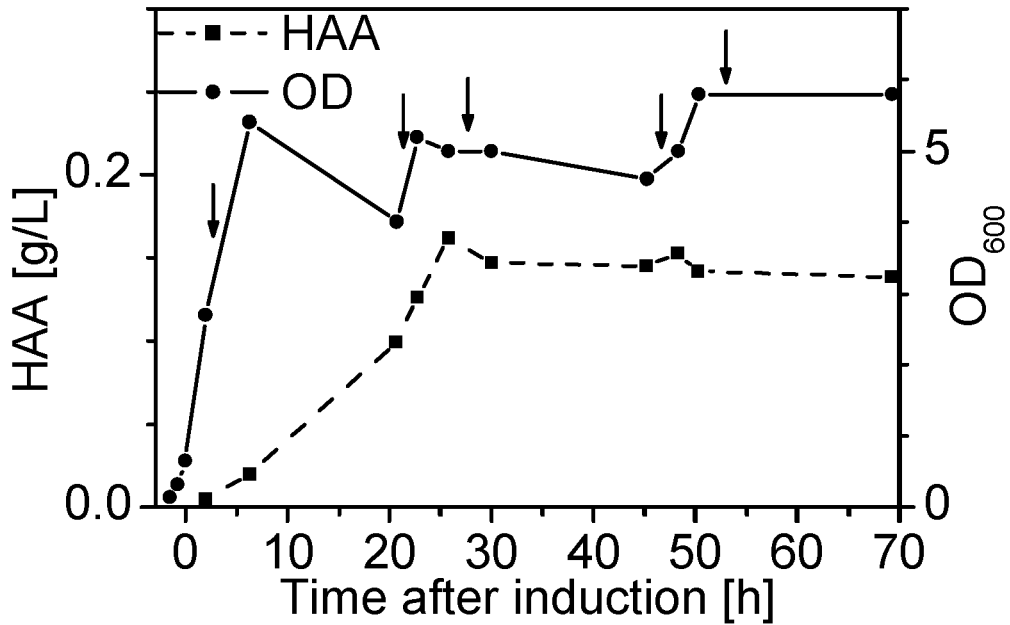
Figure 16B:
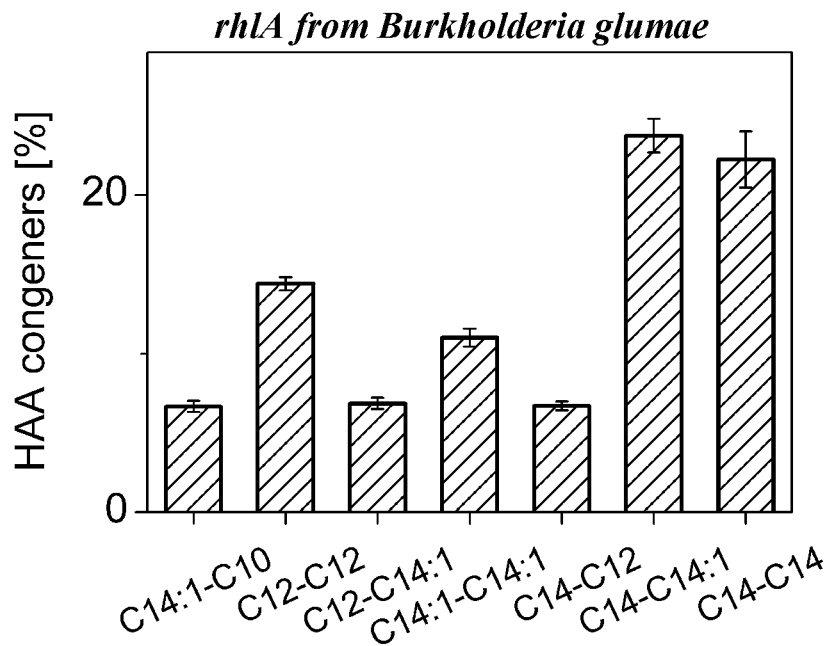
FIG. 16B: *E. coli* transformed with rhlA from *Burkholderia glumae*.
Figure 17:
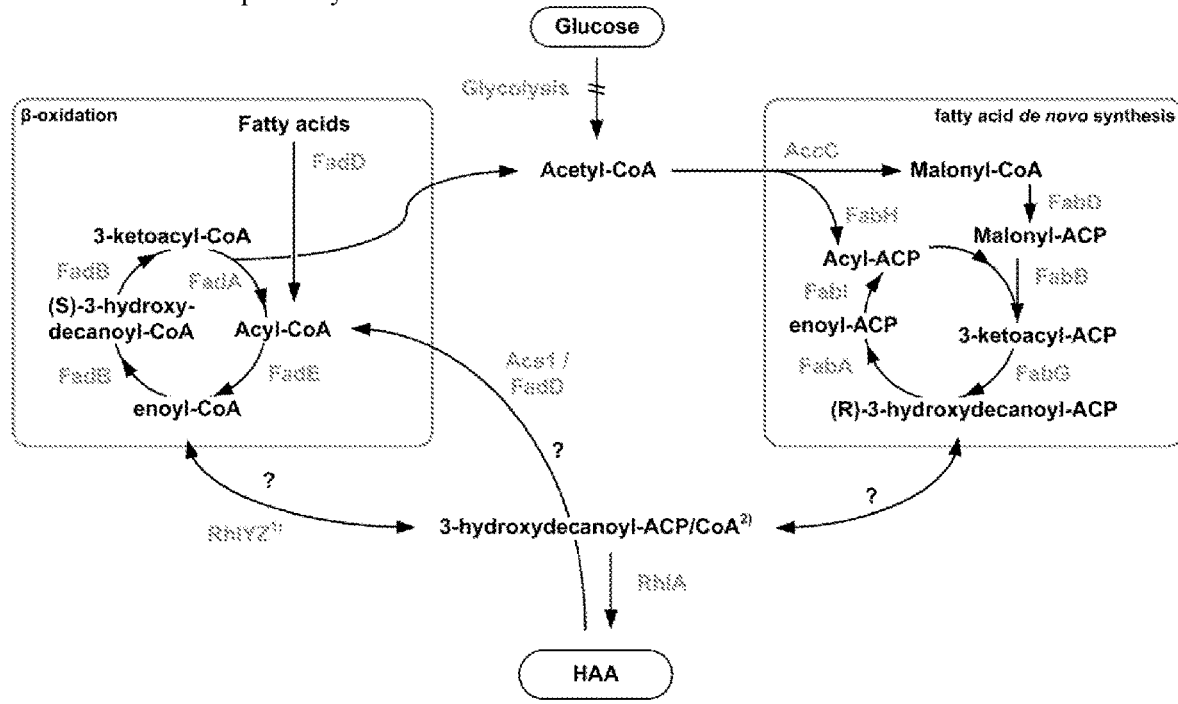
FIG. 17: Schematic representation of HAA metabolization pathway. FabH stands for β-ketoacyl-acyl carrier protein synthase III, ACP stands for acyl carrier protein, AccC stands for acetyl-CoA carboxylase, FabD stands for malonyl-CoA-ACP transacylase, FabB stands for β-ketoacyl-ACP synthase, FabG stands for β-ketoacyl ACP reductase, FabA stands for β-hydroxyacyl-ACP dehydratase, FabI stands for Enoyl-ACP-reductase, FadD stands for acyl-CoA synthetase, FadE stands for acyl-CoA dehydrogenase, FadB stands for trans-enoyl-CoA hydratase and S-3-hydroxyacyl-CoA dehydrogenase, FadA stands for 3-ketoacyl-CoA thiolase. Reactions annotated with "?" are hypothetical pathways. RhlYZ1) stands for RhlY or RhlZ that are described as R-specific enoyl-CoA hydratase by Abdel-Mawgoud et al. 2014. 3-hydroxydecanoyl-ACP/CoA$^2$: although it is currently assumed that RhlA catalyzes the reaction of ACP activated substrates, it is also possible that RhlA catalyzes the reaction of CoA-activated substrates in addition or instead. It is further assumed that Acs 1 as described by Escapa et al. 2012 or FadD is involved in HAA metabolism (assumingly together with other enzymes) and it is further assumed that HAA is metabolized by β-oxidation.

With *E. coli* C43 pBUG2 HAA titers of 160 g/l were obtained. This microbial cell factory mainly produced chain lengths of $C_{14}$-$C_{14}$ verified by HPLC-MS. The typical congeners ($C_{10}$-$C_{10}$) as produced with pPA2 and pANA2-1 could not be found (FIG. 12C). The distribution of HAA congeners is shown in FIG. 16B.

As can be seen from the distribution of HAA congeners shown in FIGS. 16A and B, the distribution of HAA congeners strongly depends on the rhlA gene. If taken together with FIG. 5, one may conclude that the distribution of HAA congeners mainly depends on the employed rhlA gene rather than on the species of the host cell.

Example 10: RNA Isolation and qRT-PCR

To determine the transcription level of the gene expression, mRNA was isolated from cell cultures after 24 hours of growth utilizing peqGOLD Bacterial RNA Kit by PEQLAB Biotechnologie GmbH (Erlangen, Germany). A maximum of $1\times10^9$ cells was utilized to isolate mRNA for quantitative PCT (qRT-PCR).

Example 11: HAA Formation in *Burkholderia plantarii* 9509

*Burkholderia plantarii* 9505 was transformed with plasmid pSB01 carrying the rhlA gene under the control of a strong synthetic promoter.

HAA expression in *B. plantarii* was performed in LB medium containing 50 mg/l kanamycin and 10 g/l glucose. Cultivation took place in system Duetz microtiter plates with 1.5 ml liquid volume. These MTP had 24 deepwell square wells and could be filled with up to 2 ml of medium. They were shaken at 30° C. and 250 rpm with a throw of 50 mm. Four different transformants with pSB01 were investigated.

Figure 18:
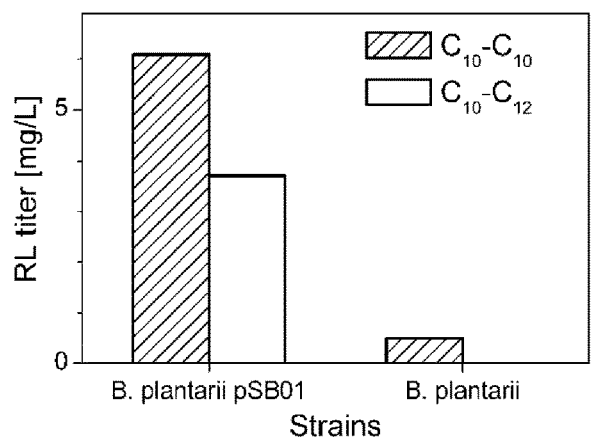
FIG. 18: HPLC analysis of culture supernatants of *B. plantarii* 9509 strains. On the right the wild type strain can be seen while *B. plantarii* 9509 pSB01 is depicted on the left. The titer for the C10-C12 di-rhamnolipid is presented with striped columns

It was found that all strains equipped with pSB01 produced di-rhamnolipids of the $C_{10}$-$C_{10}$ and $C_{10}$-$C_{12}$ congener. Concentrations detected were 10 mg/l for strains supplied with plasmid pSB01 (FIG. 18). This might be explained as the host carries rhlABC on the chromosome. We assume that HAA was formed due to plasmid encoded rhlA and converted to di-rhamnolipids by chromosomally encoded rhlBC. This theory is strengthened by the finding, that in the wildtype control without plasmid no di-Rhamnolipids were observed. Also, *Burkholderia* strains usually produce rhamnolipids with mainly the $C_{14}$-$C_{14}$ congener. We thus conclude that the overexpression of rhlA in *B. plantarii* led to the synthesis of *P. aeruginosa* type HAAs that are afterwards converted to di-rhamnolipids.

Example 12 Fermentative Production of HAAs Based on Plant Oil

Cultivation was carried out using a lab fermenter by Eppendorf. The filling volume was 1 L. The fermenter was aerated with pressurized air while the dissolved oxygen content was controlled via the stirring speed between 300 and 1,200 rpm. The pH was controlled by pumping NaOH.

*Pseudomonas taiwanensis* VLB120 was used in the here described experiment. The strain was transformed with plasmid pSB01 carrying the rhlA gene under the control of a strong synthetic promoter.

Figure 19:
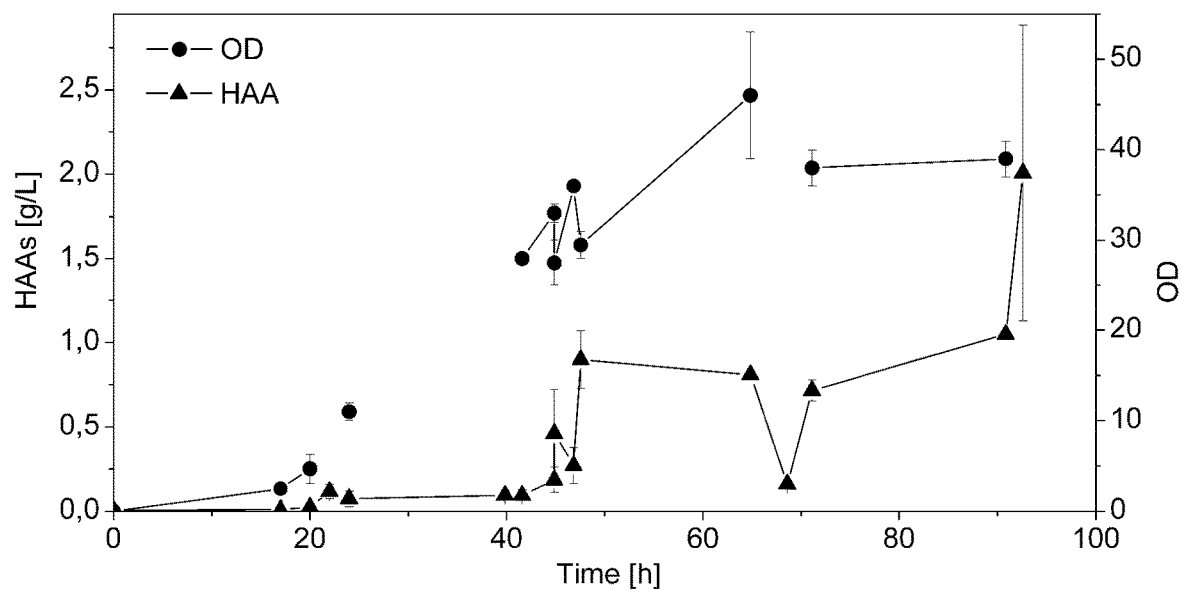
FIG. 19: Fermentation of *P. taiwanensis* VLB120 pSB01. The course of the optical density is depicted with circles while HAA titers are presented with triangles.

Cultivated in a fermenter on minimal medium with 100 g/L of sunflower oil (SO) as sole carbon source, *P. taiwanensis* VLB120 pSB01 was shown to produce more than 2 g/L of HAAs within 93 h (FIG. 19). The overall yield of the process was thus 0.01 $Cmol_{HAA}/Cmol_{SO}$ while the production rate amounted to 0.17 $mCmol_{HAA}/(L\ h)$. Both are in the same range as cultivations with glucose but nevertheless significantly lower.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims.

Several documents are cited throughout the text of this specification. Each of the documents cited herein (including all patents, patent applications, scientific publications, manufacturer's specifications, instructions, etc.), are hereby incorporated by reference in their entirety. The listing or discussion of a previously published document in this specification should not necessarily be taken as an acknowledgement that the document is part of the state of the art or is common general knowledge.

The disclosure illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible. Thus, it should be understood that although the present disclosure has been specifically disclosed by exemplary embodiments and optional features, modification and variation of the disclosures embodied therein herein disclosed may be resorted to by those skilled in the art, and that such modifications and variations are considered to be within the scope of this disclosure.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

NON-PATENT REFERENCES CITED IN THE APPLICATION

Abdel-Mawgoud et al., Appl. Microbiol. Biotechnol (2010) 86, 1323-1336

Abdel-Mawgoud et al., Chemistry & Biology. (2014) 21(1): 156-164

Altschul, et al., Nucleic Acids Res. (1997) 25:3389-3402

Altschul, et al., J. Mol. Biol. (1990) 215:403-410

Andra et al., Biol. Chem. (2006) 387, 301-310

Cabrera-Valladares et al., Appl Microbiol Biotechnol (2006) 73:187-194

Choi et al., J Biotechnol (2011) 151:30-42

Christova et al., Zeitschrift für Naturforschung (2004) 59c, 70-74

Daniels, FEMS Microbiology Reviews (2004) 28, 261-289

Dekhtyar et al., Biotechnol Lett (2010) 32, 243-248 de Lorenzo et al., Gene (1993) 123, 17-24.

de Maayer et al., J Bacteriol (2010) 192, 2936-2937

Déziel et al., Microbiology (2003) 149:2005-2013

Dubeau et al., BMC Microbiology (2009) 9:263

Elander et al., Cellulose (2009) 16:649-659

Escapa et al., Environ Microbiol 14:1049-1063

Eskin et al., Pacific Symposium on Biocomputing (2003) 8, 29-40

Heyd et al., (2008), Anal Bioanal Chem 391:1579-1590

Hörmann et al., Eur. J. Lipid Sci. Technol. (2010) 112, 674-680

Kim and Holtzapple. Bioresour Technol (2005) 96(18): 1994-2006

Kim and Lee. Bioresour Technol (2005) 96(18):2007-2013

Koch et al., J. Bacteriol (1991) 173(13):4214-4219

Köhler et al. Environ Microbiol. (2014) 17(1):156-70

Köhler et al., J Biotechnol (2013) 168, 729-730.

Lépine et al., J Mass Spectrom (2002) 37:41-46

Liu and Wyman Bioresour Technol (2005) 96(18):1978-1985

Lloyd and Wyman Bioresour Technol (2005) 96(18):1967-1977

Miroux & Walker. J Mol Biol (1996) 260, 289-298.

Mosier et al., (2005) Bioresour Technol 96(6):673-686

Nelson et al., Environ Microbiol (2002) 4, 799-808.

Ochsner et al., J Biol. Chem. (1994) 269(31):19787-19795.

Panke et al Appl Environ Microbiol (1998) 64, 2032-2043.

Rühl, J. (2012). Characterization and engineering of *Pseudomonas putida* for aerobic n-butanol production. In Laboratory of Chemical Biotechnology. Dortmund: TU Dortmund University.

Silva-Rocha et al., Nucleic Acids Res (2013) 41, D666-D675.

Smith, et al., (1981) J. Mol. Biol. 147:195-197

Stephanopoulos, Aristidou and Nielsen. Metabolic engineering: principles and methodologies San Diego: Acad. Press, 1998

Teymouri et al., (2005) Bioresour Technol 96(18):2014-2018

Wagner et al., Proc Natl Acad Sci USA (2008) 105, 14371-14376.

Williamson, N. R., et al., Environmental Microbiology (2008) 10, 5, 1202-1217

Wittgens, A. (2013).Konstruktion neuer Produktionsstämme für die heterologe Rhamnolipidsynthese in dem nichtpathogenen Wirt *Pseudomonas putida* KT2440 Ulm: Ulm University.

Zhu and Rock. J Bacteriol (2008) 190(9) 3147-3154

The invention claimed is:

1. A host cell comprising an rhlA gene or an ortholog thereof, being under the control of a heterologous promoter; wherein said host cell is *Pseudomonas* sp., is capable of producing hydroxyalkanoyloxy alkanoic acid (HAA) and achieving an HAA concentration of more than 1.4 g L$^{-1}$ when cultured, is capable of achieving a carbon yield (Cmol$_{HAA}$/Cmol$_{substrate}$) of 0.25 or more, and is capable of achieving 41% or more of the theoretical maximum of the carbon yield.

2. The host cell of claim 1, wherein the promoter is as strong or stronger than the promotor having the sequence as set forth in SEQ ID NO: 01 (SynPro8).

3. The host cell of claim 1, wherein that is *Pseudomonas taiwanensis*.

4. The host cell of claim 1, wherein the host cell is *Pseudomonas putida*.

5. The host cell of claim 1, wherein the host cell is non-pathogenic for a human subject.

6. The host cell of claim 1 not comprising an rhlB gene or an ortholog thereof, being under the control of a heterologous promoter.

7. The host cell of claim 1 not comprising an rhlC gene or an ortholog thereof, being under the control of a heterologous promoter.

8. The host cell of claim 1 having a knock-out mutation in one or more endogenous sequences encoding for a gene involved in β-oxidation of fatty acids.

9. The host cell of claim 1, wherein the cell is capable of secreting HAA.

10. A method of producing an HAA, the method comprising a steps of Culturing the host cell according to claim 1 under conditions allowing HAA production.

11. The method of claim 10 further comprising the step of recovering said HAA.

12. A method of producing a host cell according to claim 1, wherein the host cell is capable of producing HAA comprising a desired HAA comprising a fatty acid moiety with a number of carbon atoms that is an integer in the range of 6-16, wherein the desired HAA is present in an amount of 30% (w/w) or greater of a total amount of HAA produced by the host cell, the method comprising
   a) selecting an rhlA gene or ortholog thereof that encodes for a protein that catalyzes the formation of said HAA as a preferred product; and
   b) introducing said rhlA gene or ortholog thereof under the control of a heterologous promotor into the cell.

13. A host cell obtainable by the method of claim 12.

14. The method of claim 10, comprising a step of isolating HAA to provide a HAA preparation.

15. The method of claim 10 further comprising the step c) converting the HAA to give a fatty acid composition.

16. The method of claim 15, comprising a step of isolating fatty acid to provide a fatty acid composition.

17. The method of claim 10 further comprising the step c) converting the HAA to give a fatty alcohol composition.

18. The method of claim 17, comprising a step of isolating fatty alcohol to provide a fatty alcohol composition.

19. The method of claim 10 further comprising the step c) converting the HAA to give a hydrocarbon composition.

20. The method of claim 19, comprising a step of isolating hydrocarbon to provide a hydrocarbon composition.

* * * * *